United States Patent
Tainsky et al.

(10) Patent No.: US 8,614,169 B2
(45) Date of Patent: *Dec. 24, 2013

(54) NEOEPITOPE DETECTION OF DISEASE USING PROTEIN ARRAYS

(75) Inventors: Michael Tainsky, Southfield, MI (US); Sorin Draghici, Plymouth, MI (US); Madhumita Chatterjee, Lake Orion, MI (US)

(73) Assignee: Wayne State University, Detroit, MI (US)

( * ) Notice: Subject to any disclaimer, the term of this patent is extended or adjusted under 35 U.S.C. 154(b) by 240 days.

This patent is subject to a terminal disclaimer.

(21) Appl. No.: 11/816,471

(22) PCT Filed: Feb. 17, 2006

(86) PCT No.: PCT/US2006/005830
§ 371 (c)(1),
(2), (4) Date: Aug. 16, 2007

(87) PCT Pub. No.: WO2006/089219
PCT Pub. Date: Aug. 24, 2006

(65) Prior Publication Data
US 2008/0300141 A1    Dec. 4, 2008

Related U.S. Application Data

(63) Continuation of application No. 11/060,867, filed on Feb. 17, 2005, now Pat. No. 7,964,536, which is a continuation-in-part of application No. 10/004,587, filed on Dec. 4, 2001, now Pat. No. 7,863,004.

(51) Int. Cl.
*C40B 30/04* (2006.01)

(52) U.S. Cl.
USPC .......................................................... 506/9

(58) Field of Classification Search
None
See application file for complete search history.

(56) References Cited

U.S. PATENT DOCUMENTS

2001/0051344 A1* 12/2001 Shalon et al. ...................... 435/6
2004/0023415 A1*  2/2004 Sokolov et al. ............... 436/518

OTHER PUBLICATIONS

Alizadeh (Feb. 3, 2000) Nature vol. 403 pp. 503 to 511.*
Ladugger (2000) Circulation vol. 102 pp. 1221 to 1226.*
Lowe (2000) Thrombosis and Haemostasis vol. 84 pp. 553 to 558.*
Miklos (May 2004) Nature Biotechnology vol. 22 pp. 615 to 621.*
Metcalfe (Jun. 15, 2004) Journal of Clinical Oncology vol. 22 pp. 2328 to 2235.*
Lucentini (Dec. 20, 2004) The Scientist vol. 18 pp. 20 to 23.*
Kroese (Dec. 2004) Genetics in Medicine vol. 6 pp. 475 to 480.*

(Continued)

*Primary Examiner* — Ardin Marschel
*Assistant Examiner* — Christian Boesen
(74) *Attorney, Agent, or Firm* — Kohn & Associates, PLLC

(57) ABSTRACT

A biosensor for use in detecting the presence of diseases, the biosensor comprising a detector for detecting a presence of at least one marker indicative of a specific disease. A method of determining efficacy of a pharmaceutical for treating a disease or staging disease by administering a pharmaceutical to a sample containing markers for a disease, detecting the amount of at least one marker of the disease in the sample, and analyzing the amount of the marker in the sample, whereby the amount of marker correlates to pharmaceutical efficacy or disease stage. Markers for gynecological disease selected from the list in Table 8. An immuno-imaging agent comprising labeled antibodies, whereby the labeled antibodies are isolated and reactive to proteins overexpressed in vivo. Informatics software for analyzing the arrays of claim 17, the software including analyzing means for analyzing the arrays.

1 Claim, 11 Drawing Sheets

(56) References Cited

OTHER PUBLICATIONS

Zimmern (May 24, 2007) Journal of Public Health vol. 1 pp. 1 to 5.*
Tainsky (Jul. 10, 2007) Biomarker Insights pp. 261 to 267.*
Valid Concerns Editorial (Jan. 27, 2010) Nature vol. 463 pp. 401 to 402.*
Alizadeh A.A., et al; Distinct Types of Diffuse Large B-Cell Lymphomas Identified by Gene Expression Profiling. Nature 403:503-511 (2000).
An, A., et al; A Learning System for More Accurate Classifications; Lecture Notes in Artificial Intelligence. Vancouver 1418:426-441 (1998).
Aunoble, B., et al; Major Oncogenes and Tumor Suppressor Genes involved in Epithelial Ovarian Cancer. International Journal of Oncology 16:567-76 (2000).
Baron, A.T, et al; Serum sErbB1 and Epidermal Growth Factor Levels as Tumor Biomarkers in Women with Stage III or IV Epithelial Ovarian Cancer Epidemiology. Biomarkers & Prevention 8:129-137 (1999).
Bauer, R., et al; Cloning and Characterization of the Drosophila Homologue of the AP-2 Transcription Factor. Oncogene 17:1911-1922 (1998).
Bast, R.C., et al; Reactivity of a Monoclonal Antibody with Human Ovarian Carcinoma. J Clin Invest. 68:1331-1337 (1981).
Bast, R.C., et al; A Radioimmunoassay Using a Monoclonal Antibody to Monitor the Course of Epithelial Ovarian Cancer. N Engl J Med 309:883-887 (1983).
Berek, J.S., et al; Serum Interleukins-6 Levels Correlate with Disease Status in Patients with Epithelial Ovarian Cancer. Am J Obstet Gynecol 164:1038-1043 (1991).
Bittner, M., et al; Molecular Classification of Cutaneous Malignant Melanoma by Gene Expression Profiling. Nature 406:536-540 (2000).
Buettner, R., et al; An Alternatively Spliced Form of AP-2 Encodes a Negative Regulator of Transcriptional Activation by AP-2; Mol. Cell Biol 13:4174-4185 (1993).
Chiao, P.J., et al; Elevated Expression of the Human Ribosomal S2 Gene in Human Tumors; Molecular Carcinogenesis 5:219-231 (1992).
Clark, P., et al; The CN2 Induction Algorithm. Machine Learning 3:261-283 (1989).
Deyo, J., et al; A Novel Protein Expressed at High Cell Density But Not During Growth Arrest. DNA and Cell Biol 17:437-447 (1998).
Draghici, S., The Constraint Based Decomposition (CBD) Training Architecture. Neural Networks 14:527-550 (2001).
Einhorn, N., et al; Prospective Evaluation of Serum CA 125 Levels for Early Detection of Ovarian Cancer. Obstet Gynecol 80:14-18 (1992).
Gotlieb, W.H., et al; Presence of Interleukins in the Ascites of Patients with Ovarian and Other Intra-Abdominal Cancers. Cytokine 4:385-390 (1992).
Greenlee, R.T., et al; Cancer Statistics. CA Cancer J Clin 50:70-33 (2000).

Heath, S., et al; Induction of Oblique Decision Tree. In IJCAI-93, Washington D.C. (1993).
Hogdall, E.V., et al; Predictive Values of Serum Tumour Markers Tetranectin, OVX1, CASA and CA125 in Patients with a Pelvic mass. Int J Cancer 89:519-523 (2000).
Holschneider, C.H., et al; Ovarian Cancer: Epidemiology, Biology, and Prognostic Factors. Semin Surg Oncol 1:3-10 (2000).
Jacobs, I.J.; et al; Potential Screening Tests for Ovarian Cancer. London, Chapman and Hall medical, 197-205 (1997).
Jacobs, I., et al; Multimodal Approach to Screening for Ovarian Cancer. Lancet I 268-271 (1988).
Jacobs, I., et al; The CA 125 Tumor-Associated Antigen: A Review of the Literature. Hum Reprod 4:1-12 (1989).
Kacinski, B.M., et al; Macrophage Colony-Stimulating Factor is Produced by Human Ovarian and Endometrial Adenocarinoma-Derived Celle Lines and is Present at Abnormally High Levels in the Plasma of Ovarian Carcinoma Patients with Active Disease. Cancer Cells 7:333-337 (1989).
Kerr, M., et al; Analysis of Variance for Gene Expression Microarray Data. Journal of Computational Biology (2000).
Kim, S.Y., et al; Coordinate Control of Growth and Cytokeratin 13 Expression by Retinoic Acid. Molecular Carcinogenesis 16:6-11 (1996).
Kohonen, T.; Learning Vector Quantization. Neural Networks, 1 (suppl. 1): 303 (1988).
Peng, Y.S., et al; ARHIS is the Center of Allelic Deletion on Chromosome Ip31 in Ovarian and Breast Cancers. Int J Cancer 86:690-694 (2000).
Precup, D., et al; Classification Using-Maching and Constructive unction Approximation. In Proc. 15th International Conf. on Machine Learning, 439-444. Morgan Kauffman, San Francisco, CA (1998).
Poggio, T., et al; Networks for Approximation and Learning. Proceedings of IEEE 78(9): 1481-149 (1990).
Rumelhart, D.E., et al; Learning Internal Representations by Error Propagation. Parallel Distributed Processing: Explorations in the Microstructures of Cognition, MIT Press/Bradford Books (1987).
Schwartz, P.E., et al; Circulating Tumor Markers in the Monitoring of Gynecologic Malignancies. Cancer 60:353-361 (1987).
Schmittgen, T.D., et al; Quantitative Revers Transcription-Polymerase Chain Reaction to Study mRNA decay: Comparison of Endpoint and Real-Time Methods. Analytical Biochem, 285:194-204 (2000).
Sonoda, K. et al; A Novel Tumor-Associated Antigen Expressed in Human Uterine and Ovarian Carcinomas. Cancer 77:1501-9 (1996).
Nakashima, M., et al; Inhibition of Cell Growth and Induction of Apoptotic Cell Death by the Human Tumor-Associated Antigen RCAS1. nat Med. 5:938-42 (1999).
Musavi, M., et al; On the Training of Radial Basis Functions Classifiers. Neural Networks 5:595-603 (1992).
Houts, T.M.; Improved 2-Color Normalization for Microarray Analyses Employing Cyanine Dyes, CAMDA (2000).
Conrad, et al., From Animal Models to Human Genetics: Research on the Induction and Pathogenicity of Autoantibodies, Pabst Science Publishers, Lengerich, 2004, pp. 463-466.

* cited by examiner

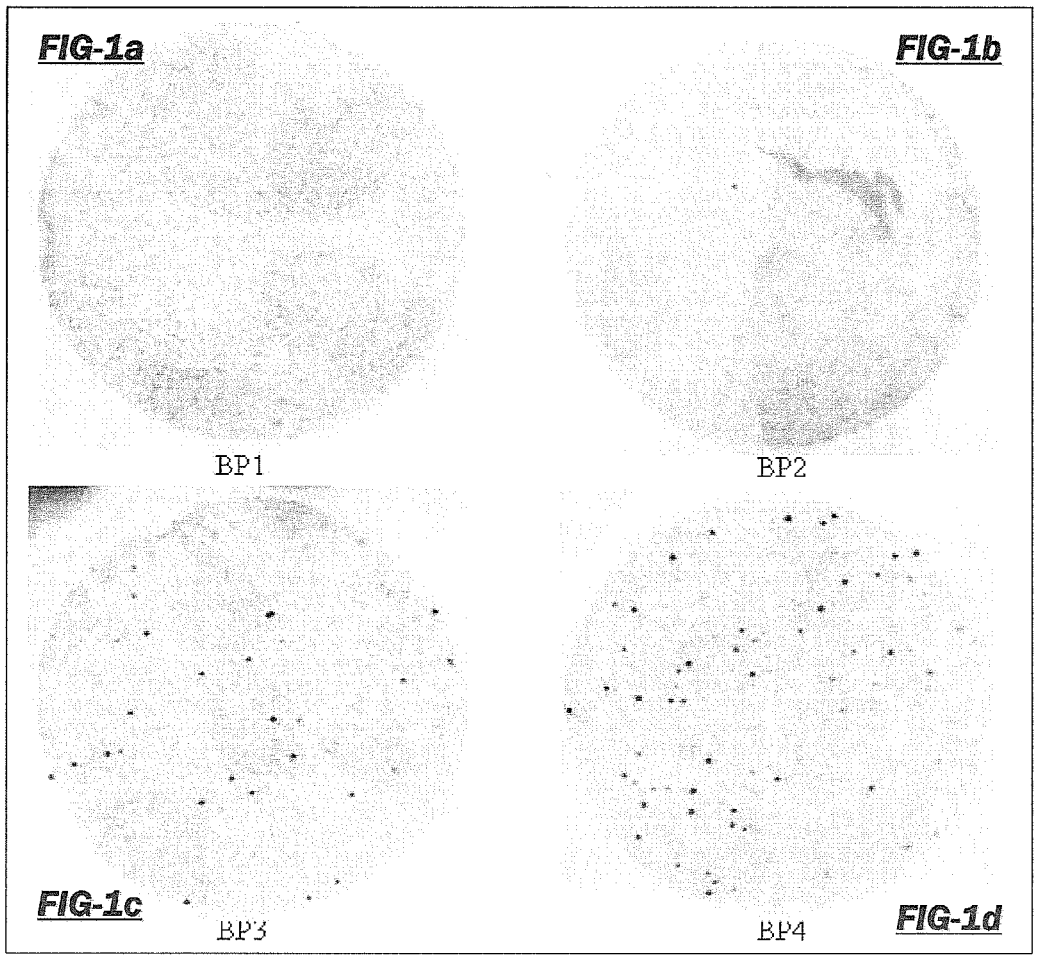
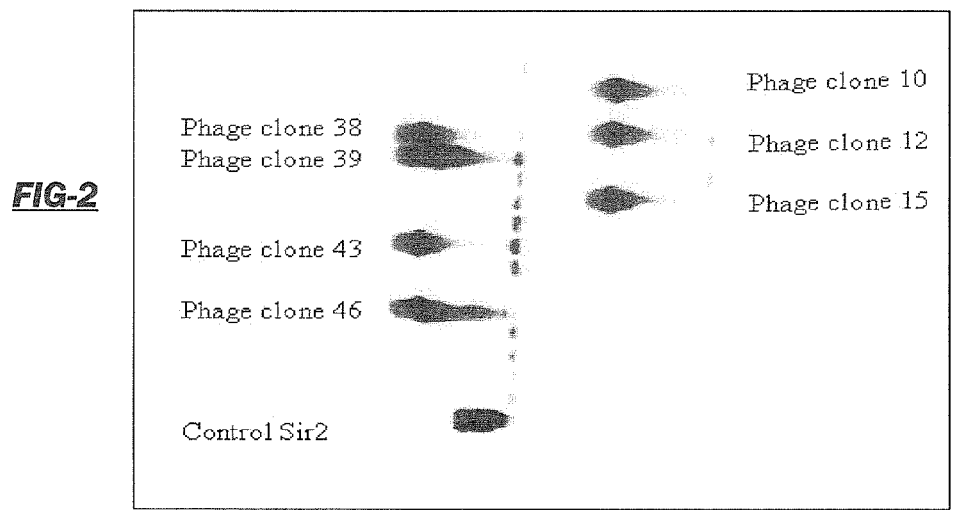

Library

BioPan I

BioPan II

BioPan III

BioPan IV

| Clones from patient | Source of sera | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 1 | 1 | | | | | | | | | | | |
| 2 | | 1 | | | | | | | | | | |
| 3 | | | 1 | | | | | | | | | |
| 4 | | | | 1 | | | | | | | | |
| 5 | | | | | 1 | | | | | | | |
| 6 | | | | | | 1 | | | | | | |
| 7 | | | | | | | 1 | | | | | |
| 8 | | | | | | | | 1 | | | | |
| 9 | | | | | | | | | 1 | | | |
| 10 | | | | | | | | | | 1 | | |
| 11 | | | | | | | | | | | ? | |
| 12 | | | | | | | | | | | | ? |

FIG - 10

| Clones from patient | Source of sera | | | | | | | | | |
|---|---|---|---|---|---|---|---|---|---|---|
| | 1 | 2 | 3 | 4 | 5 | 6 | 7 | 8 | 9 | 10 |
| 2 | | 1 | | 1 | | | | 1 | | |
| 3 | | | 1 | | | 1 | | | | 1 |
| 5 | | | | | 1 | | | 1 | 1 | |
| 7 | | | | | | | 1 | | | 1 |
| 8 | | | | | | | | 1 | | |
| 9 | | | | | | | | | 1 | |
| 10 | | | | | | | | | | 1 |
| 1 | 1 | | | | | | | | | |
| 4 | | | | 1 | | | | | | |
| 6 | | | | | | 1 | | | | |

FIG - 11

Late Stage OVC015

Late Stage Mec23

Stage I 4679

Stage I 4387

Con OV019-c

Con 2 R2

NEOEPITOPE DETECTION OF DISEASE USING PROTEIN ARRAYS

CROSS-REFERENCE TO RELATED APPLICATIONS

This is a National Phase Filing Under 35 U.S.C. 371, of International Application No. PCT/US06/05830, filed Feb. 17, 2006, which claims priority to U.S. patent application Ser. No. 11/060,867 filed Feb. 17, 2005, which is a Continuation-In-Part of U.S. patent application Ser. No. 10/004,587 filed Dec. 4, 2001, all of which are incorporated herein by reference.

BACKGROUND OF THE INVENTION

1. Technical Field

The present invention relates to an assay and method for diagnosing disease. More specifically, the present invention relates to an immunoassay for use in diagnosing cancer.

2. Background Art

It is commonly known in the art that genetic mutations can be used for detecting cancer. For example, the tumorigenic process leading to colorectal carcinoma formation involves multiple genetic alterations (Fearon et al (1990) Cell 61, 759-767). Tumor suppressor genes such as p53, DCC and APC are frequently inactivated in colorectal carcinomas, typically by a combination of genetic deletion of one allele and point mutation of the second allele (Baker et al (1989) Science 244, 217-221; Fearon et al (1990) Science 247, 49-56; Nishisho et al (1991) Science 253, 665-669; and Groden et al (1991) Cell 66, 589-600). Mutation of two mismatch repair genes that regulate genetic stability was associated with a form of familial colon cancer (Fishel et al (1993) Cell 75, 1027-1038; Leach et al (1993) Cell 75, 1215-1225; Papadopoulos et al (1994) Science 263, 1625-1629; and Bronner et al (1994) Nature 368, 258-261). Proto-oncogenes such as myc and ras are altered in colorectal carcinomas, with c-myc RNA being overexpressed in as many as 65% of carcinomas (Erisman et al (1985) Mol. Cell. Biol. 5, 1969-1976), and ras activation by point mutation occurring in as many as 50% of carcinomas (Bos et al (1987) Nature 327, 293-297; and Forrester et al (1987) Nature 327, 298-303). Other proto-oncogenes, such as myb and neu are activated with a much lower frequency (Alitalo et al (1984) Proc. Natl. Acad. Sci. USA 81, 4534-4538; and D'Emilia et al (1989) Oncogene 4, 1233-1239). No common series of genetic alterations is found in all colorectal tumors, suggesting that a variety of such combinations can be able to generate these tumors.

Increased tyrosine phosphorylation is a common element in signaling pathways that control cell proliferation. The deregulation of protein tyrosine kinases (PTKS) through overexpression or mutation has been recognized as an important step in cell transformation and tumorigenesis, and many oncogenes encode PTKs (Hunter (1989) in oncogenes and the Molecular Origins of Cancer, ed. Weinberg (Cold Spring Harbor Laboratory Press, Cold Spring Harbor, N.Y.), pp. 147-173). Numerous studies have addressed the involvement of PTKs in human tumorigenesis. Activated PTKs associated with colorectal carcinoma include c-neu (amplification), trk (rearrangement), and c-src and c-yes (mechanism unknown) (D'Emilia et al (1989), ibid; Martin-Zanca et al (1986) Nature 3, 743-748; Bolen et al (1987) Proc. Natl. Acad. Sci. USA 84, 2251-2255; Cartwright et al (1989) J. Clin. Invest. 83, 2025-2033; Cartwright et al (1990) Proc. Natl. Acad. Sci. USA 87, 558-562; Talamonti et al (1993) J. Clin. Invest. 91, 53-60; and Park et al (1993) Oncogene 8, 2627-2635).

Mutations, such as those disclosed above can be useful in detecting cancer. However, there have been few advancements which can repeatably be used in diagnosing cancer prior to the existence of a tumor. For example, breast cancer, which is by far the most common form of cancer in women, is the second leading cause of cancer death in humans. Despite many recent advances in diagnosing and treating breast cancer, the prevalence of this disease has been steadily rising at a rate of about 1% per year since 1940. Today, the likelihood that a women living in North America can develop breast cancer during her lifetime is one in eight.

The current widespread use of mammography has resulted in improved detection of breast cancer. Nonetheless, the death rate due to breast cancer has remained unchanged at about 27 deaths per 100,000 women. All too often, breast cancer is discovered at a stage that is too far advanced, when therapeutic options and survival rates are severely limited. Accordingly, more sensitive and reliable methods are needed to detect small (less than 2 cm diameter), early stage, in situ carcinomas of the breast. Such methods should significantly improve breast cancer survival, as suggested by the successful employment of Papinicolou smears for early detection and treatment of cervical cancer.

In addition to the problem of early detection there remain serious problems in distinguishing between malignant and benign breast disease, in staging known breast cancers, and in differentiating between different types of breast cancers (eg. estrogen dependent versus non-estrogen dependent tumors). Recent efforts to develop improved methods for breast cancer detection, staging and classification have focused on a promising array of so-called cancer "markers." Cancer markers are typically proteins that are uniquely expressed (e.g. as a cell surface or secreted protein) by cancerous cells, or are expressed at measurably increased or decreased levels by cancerous cells compared to normal cells. Other cancer markers can include specific DNA or RNA sequences marking deleterious genetic changes or alterations in the patterns or levels of gene expression associated with particular forms of cancer.

The utility of specific breast cancer markers for screening and diagnosis, staging and classification, monitoring and/or therapy purposes depends on the nature and activity of the marker in question. For general reviews of breast cancer markers, see Porter-Jordan et al., Hematol. Oncol. Clin. North Amer. 8: 73-100, 1994; and Greiner, Pharmaceutical Tech., May, 1993, pp. 28-44. As reflected in these reviews, a primary focus for developing breast cancer markers has centered on the overlapping areas of tumorigenesis, tumor growth and cancer invasion. Tumorigenesis and tumor growth can be assessed using a variety of cell proliferation markers (for example Ki67, cyclin D1 and proliferating cell nuclear antigen (PCNA)), some of which can be important oncogenes as well. Tumor growth can also be evaluated using a variety of growth factor and hormone markers (for example estrogen, epidermal growth factor (EGF), erbB-2, transforming growth factor (TGF)a), which can be overexpressed, underexpressed or exhibit altered activity in cancer cells. By the same token, receptors of autocrine or exocrine growth factors and hormones (for example insulin growth factor (IGF) receptors, and EGF receptor) can also exhibit changes in expression or activity associated with tumor growth. Lastly, tumor growth is supported by angiogenesis involving the elaboration and growth of new blood vessels and the concomitant expression of angiogenic factors that can serve as markers for tumorigenesis and tumor growth.

In addition to tumorigenic, proliferation and growth markers, a number of markers have been identified that can serve as indicators of invasiveness and/or metastatic potential in a population of cancer cells. These markers generally reflect altered interactions between cancer cells and their surrounding microenvironment. For example, when cancer cells invade or metastasize, detectable changes can occur in the expression or activity of cell adhesion or motility factors, examples of which include the cancer markers Cathepsin D, plasminogen activators, collagenases and other factors. In addition, decreased expression or overexpression of several putative tumor "suppressor" genes (for example nm23, p53 and rb) has been directly associated with increased metastatic potential or deregulation of growth predictive of poor disease outcome.

Additionally, ovarian cancer has the highest mortality rate of all gynecological cancers and yet there is still no reliable and easy to administer screening test. Using the multimodality approach to treatment, including aggressive cytoreductive surgery in combination with chemotherapy, five-year survival rates diminish with increasing stage: Stage I (93%), Stage II (70%), Stage III (37%), and Stage IV (25%). Despite advances in molecular biology, surgical oncology, and chemotherapy, the overall prognosis for ovarian cancer patients diagnosed at Stages II-IV remains poor. The excellent survival rates for Stage I disease provide the rationale for efforts to detect early-stage ovarian cancer as a screening test. The first priority of any screening procedure for ovarian cancer is high specificity in order to minimize the number of false positive results and thereby ensuring an acceptable positive predictive value (PPV). There have been no effective and reliable tests developed to date.

Screening for ovarian cancer has been based on strategies using serum tumor markers or ultrasound imaging of the ovaries. The most extensively investigated biomarker is CA-125, whose serum levels are elevated in 50% of Stage I and 90% of Stage II ovarian cancer patients. However, elevated CA-125 levels have also been observed in healthy women during menstruation, in patients with other gynecological diseases, and other malignancies, which suggests that the false-positive rate of CA-125 can be high.

In contrast to detection of serum antigens, the detection of serum antibody responses to tumor antigens may provide a more reliable serum marker for cancer diagnosis because serum antibodies are more stable than serum antigens. Furthermore, antibodies may be more abundant than antigens, especially at low tumor burdens characteristic of early stages. Thirty percent of patients with ductal carcinoma in situ (DCIS) in which the protooncogene HER2/neu was overexpressed had serum antibodies specific to this protein. In addition, antibodies to p53 have been reported in patients with early-stage ovarian, and colorectal cancers. Antibodies against heat shock protein 90 (HSP90) were also found to be associated with patients' survival and tumor metastasis. Antibodies against ribosomal proteins may constitute a novel serological marker. The presence of antibodies to ubiquitin C-terminal hydrolase L3 in colon cancer has also been reported. Changes in the level of gene expression in cancer and aberrant expression of tissue-restricted gene products in cancer are factors in the development of a humoral immune response in cancer patients. In this respect, serological analysis of recombinant cDNA expression libraries (SEREX) of human tumors with autologous serum has identified some relevant tumor antigens. Among the gene products shown to be immunogenic are MAGE, SSX2, and NY-ESO-1, which are expressed in various tumor types, but not in normal tissues except testis.

Studies on new technology based on proteomic patterns in serum to screen for early stage ovarian cancer have been reported by Petricoin et al. (2002). The procedure involved generating proteomic spectra of serum proteins using Matrix-assisted laser desorption and ionization time-of-flight (MALDI-TOF) and surface-enhanced laser desorption and ionization time-of-flight (SELDI-TOF) mass spectroscopy. In independent validation to detect early stage invasive epithelial ovarian cancer from healthy controls, the sensitivity of a multivariate model combining the three biomarkers and CA125 [74% (95% CI, 52-90%)] was higher than that of CA125 alone [65% (95% CI, 4-84%)] at a matched specificity of 97% (95% CI, 89-100%). When compared at a fixed sensitivity of 83% (95% CI, 61-95%), the specificity of the model [94% (95% CI, 85-98%)] was significantly better than that of CA125 alone [52% (95% CI, 39-65%)]. Due to the low prevalence of ovarian cancer in the general population, this level of specificity is unacceptable for a realistic ovarian cancer diagnostic test. Assuming that in a clinical setting with low-risk patients, ovarian cancer is present in approximately one per 2500 patients, the (MALDI/SELDI) approach would produce 125 false positives for every true cancer patient. Furthermore, some issues have arisen regarding the mass spectroscopy technology of protein profiling. It has been reported that the data obtained by this technology are difficult to reproduce and that they may be biased by artifacts in sample preparation, storage and processing, and patient selection.

In summary, the evaluation of proliferation markers, oncogenes, growth factors and growth factor receptors, angiogenic factors, proteases, adhesion factors and tumor suppressor genes, among other cancer markers, can provide important information concerning the risk, presence, status or future behavior of cancer in a patient. Determining the presence or level of expression or activity of one or more of these cancer markers can aid in the differential diagnosis of patients with uncertain clinical abnormalities, for example by distinguishing malignant from benign abnormalities. Furthermore, in patients presenting with established malignancy, cancer markers can be useful to predict the risk of future relapse, or the likelihood of response in a particular patient to a selected therapeutic course. Even more specific information can be obtained by analyzing highly specific cancer markers, or combinations of markers, which can predict responsiveness of a patient to specific drugs or treatment options.

Methods for detecting and measuring cancer markers have been recently revolutionized by the development of immunological assays, particularly by assays that utilize monoclonal antibody technology. Previously, many cancer markers could only be detected or measured using conventional biochemical assay methods, which generally require large test samples and are therefore unsuitable in most clinical applications. In contrast, modern immunoassay techniques can detect and measure cancer markers in relatively much smaller samples, particularly when monoclonal antibodies that specifically recognize a targeted marker protein are used. Accordingly, it is now routine to assay for the presence or absence, level, or activity of selected cancer markers by immunohistochemically staining tissue specimens obtained via conventional biopsy methods. Because of the highly sensitive nature of immunohistochemical staining, these methods have also been successfully employed to detect and measure cancer markers in smaller, needle biopsy specimens which require less invasive sample gathering procedures compared to conventional biopsy specimens. In addition, other immunological methods have been developed and are now well known in the art that allow for detection and measurement of cancer markers in non-cellular samples such as serum and other biological fluids from patients. The use of these alternative sample sources substantially reduces the morbidity and costs of assays compared to procedures employing conventional biopsy samples, which allows for application of cancer marker assays in early screening and low risk monitoring programs where invasive biopsy procedures are not indicated.

For the purpose of cancer evaluation, the use of conventional or needle biopsy samples for cancer marker assays is often undesirable, because a primary goal of such assays is to detect the cancer before it progresses to a palpable or detectable tumor stage. Prior to this stage, biopsies are generally contraindicated, making early screening and low risk monitoring procedures employing such samples untenable. Therefore, there is general need in the art to obtain samples for cancer marker assays by less invasive means than biopsy, for example by serum withdrawal.

Efforts to utilize serum samples for cancer marker assays have met with limited success, largely because the targeted markers are either not detectable in serum, or because telltale changes in the levels or activity of the markers cannot be monitored in serum. In addition, the presence of cancer markers in serum probably occurs at the time of micro-metastasis, making serum assays less useful for detecting pre-metastatic disease.

Previous attempts to develop non-invasive breast cancer marker assays utilizing mammary fluid samples have included studies of mammary fluid obtained from patients presenting with spontaneous nipple discharge. In one of these studies, conducted by Inaji et al., Cancer 60: 3008-3013, 1987, levels of the breast cancer marker carcinoembryonic antigen (CEA) were measured using conventional, enzyme linked immunoassay (ELISA) and sandwich-type, monoclonal immunoassay methods. These methods successfully and reproducibly demonstrated that CEA levels in spontaneously discharged mammary fluid provide a sensitive indicator of nonpalpable breast cancer. In a subsequent study, also by Inaji et al., Jpn. J. Clin. Oncol. 19: 373-379, 1989, these results were expanded using a more sensitive, dry chemistry, dot-immunobinding assay for CEA determination. This latter study reported that elevated CEA levels occurred in 43% of patients tested with palpable breast tumors, and in 73% of patients tested with nonpalpable breast tumors. CEA levels in the discharged mammary fluid were highly correlated with intratumoral CEA levels, indicating that the level of CEA expression by breast cancer cells is closely reflected in the mammary fluid CEA content. Based on these results, the authors concluded that immunoassays for CEA in spontaneously discharged mammary fluid are useful for screening nonpalpable breast cancer.

Although the evaluation of mammary fluid has been shown to be a useful method for screening nonpalpable breast cancer in women who experience spontaneous nipple discharge, the rarity of this condition renders the methods of Inaji et al, inapplicable to the majority of women who are candidates for early breast cancer screening. In addition, the first Inaji report cited above determined that certain patients suffering spontaneous nipple discharge secrete less than 10 µl of mammary fluid, which is a critically low level for the ELISA and sandwich immunoassays employed in that study. It is likely that other antibodies used to assay other cancer markers can exhibit even lower sensitivity than the anti-CEA antibodies used by Inaji and coworkers, and can therefore not be adaptable or sensitive enough to be employed even in dry chemical immunoassays of small samples of spontaneously discharged mammary fluid.

In view of the above, an important need exists in the art for more widely applicable, non-invasive methods and materials to obtain biological samples for use in evaluating, diagnosing and managing breast and other diseases including cancer, particularly for screening early stage, nonpalpable tumors. A related need exists for methods and materials that utilize such readily obtained biological samples to evaluate, diagnose and manage disease, particularly by detecting or measuring selected cancer markers, or panels of cancer markers, to provide highly specific, cancer prognostic and/or treatment-related information, and to diagnose and manage pre-cancerous conditions, cancer susceptibility, bacterial and other infections, and other diseases.

With specific regard to such assays, specific antibodies can only be measured by detecting binding to their antigen or a mimic thereof. Although certain classes of immunoglobulins containing the antibodies of interest can, in some cases, be separated from the sample prior to the assay (Decker, et al., EP 0,168,689 A2), in all assays, at least some portion of the sample immunoglobulins are contacted with antigen. For example, in assays for specific IgM, a portion of the total IgM can be adsorbed to a surface and the sample removed prior to detection of the specific IgM by contacting with antigen. Binding is then measured by detection of the bound antibody, detection of the bound antigen or detection of the free antigen.

For detection of bound antibody, a labeled anti-human immunoglobulin or labeled antigen is normally allowed to bind antibodies that have been specifically adsorbed from the sample onto a surface coated with the antigen, Bolz, et al., U.S. Pat. No. 4,020,151. Excess reagent is washed away and the label that remains bound to the surface is detected. This is the procedure in the most frequently used assays, or example, for hepatitis and human immunodeficiency virus and for numerous immunohistochemical tests, Nakamura, et al., Arch Pathol Lab Med 112:869-877 (1988). Although this method is relatively sensitive, it is subject to interference from non-specific binding to the surface by non-specific immunoglobulins that can not be differentiated from the specific immunoglobulins.

Another method of detecting bound antibodies involves combining the sample and a competing labeled antibody, with a support-bound antigen, Schuurs, et al., U.S. Pat. No. 3,654,090. This method has its limitations because antibodies in sera bind numerous epitopes, making competition inefficient.

For detection of bound antigen, the antigen can be used in excess of the maximum amount of antibody that is present in the sample or in an amount that is less than the amount of antibody. For example, radioimmunoprecipitation ("RIP") assays for GAD autoantibodies have been developed and are currently in use, Atkinson, et al., Lancet 335:1357-1360 (1990). However, attempts to convert this assay to an enzyme linked immunosorbent assay ("ELISA") format have not been successful. The RIP assay is based on precipitation of immunoglobulins in human sera, and led to the development of a radioimmunoassay ("RIA") for GAD autoantibodies. In both the RIP and the RIA, the antigen is added in excess and the bound antigen:antibody complex is precipitated with protein A-Sepharose®. The complex is then washed or further separated by electrophoresis and the antigen in the complex is detected.

Other precipitating agents can be used such as rheumatoid factor or C1q, Masson, et al., U.S. Pat. No. 4,062,935; polyethylene glycol, Soeldner, et al., U.S. Pat. No. 4,855,242; and protein A, Ito, et al., EP 0,410,893 A2. The precipitated antigen can be measured to indicate the amount of antibody in the sample; the amount of antigen remaining in solution can be measured; or both the precipitated antigen and the soluble antigen can be measured to correct for any labeled antigen that is non-specifically precipitated. These methods, while quite sensitive, are all difficult to carry out because of the need for rigorous separation of the free antigen from the bound complex, which requires at a minimum filtration or centrifugation and multiple washing of the precipitate.

Alternatively, detection of the bound antigen can be employed when the amount of antigen is less than the maximum amount of antibody. Normally, that is carried out using particles such as latex particles or erythrocytes that are coated with the antigen, Cambiaso, et al., U.S. Pat. No. 4,184,849 and Uchida, et al., EP 0,070,527 A1. Antibodies can specifically agglutinate these particles and can then be detected by light scattering or other methods. It is necessary in these assay to use a precise amount of antigen as too little antigen provides an assay response that is biphasic and high antibody titers can be read as negative, while too much antigen adversely affects the sensitivity. It is therefore necessary to carry out sequential dilutions of the sample to assure that positive samples are not missed. Further, these assays tend to detect only antibodies with relatively high affinities and the sensitivity of the method is compromised by the tendency for all of the binding sites of each antibody to bind to the antigen on the particle to which it first binds, leaving no sites for binding to the other particle.

For assays in which the free antigen is detected, the antigen can also be added in excess or in a limited amount although only the former has been reported. Assays of this type have been described where an excess of antigen is added to the sample, the immunoglobulins are precipitated, and the antigen remaining in the solution is measured, Masson, et al., supra and Soeldner, et al., supra. These assays are relatively insensitive because only a small percentage change in the amount of free antigen occurs with low amounts of antibody, and this small percentage is difficult to measure accurately.

Practical assays in which the free antigen is detected and the antigen is not present in excess of the maximum amount of antibody expected in a sample have not been described. However, in van Erp, et al., Journal of Immunoassay 12(3):425-443 (1991), a fixed concentration of monoclonal antibody was incubated with a concentration dilution series of antigen, and free antigen was then measured using a gold sol particle agglutination immunoassay to determine antibody affinity constants.

There has been much research in the area of evaluating useful markers for determining the risk factor for patients developing IDDM. These include insulin autoantibodies, Soeldner, et al., supra and circulating autoantibodies to glutamic acid decarboxylase ("GAD"), Atkinson, et al., PCT/US89/05570 and Tobin, et al., PCT/US91/06872. In addition, Rabin, et al., U.S. Pat. No. 5,200,318 describes numerous assay formats for the detection of GAD and pancreatic islet cell antigen autoantibodies. GAD autoantibodies are of particular diagnostic importance because they occur in preclinical stages of the disease, which can make therapeutic intervention possible. However, the use of GAD autoantibodies as a diagnostic marker has been impeded by the lack of a convenient, nonisotopic assay.

One assay method involves incubating a support-bound antigen with the sample, then adding a labeled anti-human immunoglobulin. This is the basis for numerous commercially available assay kits for antibodies such as the Syn ELISA kit which assays for autoantibodies to GAD65, and is described in product literature entitled "Syn $^{ELISA}$ GAD II-Antibodies" (Elias USA, Inc.). Substantial dilution of the sample is required because the method is subject to high background signals from adsorption of non-specific human immunoglobulins to the support.

Many of the assays described above involve detection of antibody that becomes bound to an immobilized antigen. This can have an adverse affect on the sensitivity of the assay due to difficulty in distinguishing between specific immunoglobulins and other immunoglobulins in the sample, which bind non-specifically to the immobilized antigen. There is not only a need to develop an assay that avoids non-specific detection of immunoglobulins, but there is also the need for an improved method of detecting antibodies that combines the sensitivity advantage of immunoprecipitation assays with a simplified protocol. Finally, assays that can help evaluate the risk of developing diseases are medically and economically very important. The present invention addresses these needs.

SUMMARY OF THE INVENTION

According to the present invention, there is provided a biosensor for use in detecting the presence of diseases, the biosensor comprising a detector for detecting a presence of at least one marker indicative of a specific disease. Also provided is a method of determining efficacy of a pharmaceutical for treating a disease or staging disease by administering a pharmaceutical to a sample containing markers for a disease, detecting the amount of at least one marker of the disease in the sample, and analyzing the amount of the marker in the sample, whereby the amount of marker correlates to pharmaceutical efficacy or disease stage. Markers for gynecological disease selected from the list in Table 8 are provided. An immuno-imaging agent comprising labeled antibodies, whereby the labeled antibodies are isolated and reactive to proteins overexpressed in vivo are provided. Informatics software for analyzing the arrays discussed above is provided, wherein the software includes analyzing means for analyzing the arrays.

DESCRIPTION OF THE DRAWINGS

Other advantages of the present invention are readily appreciated as the same becomes better understood by reference to the following detailed description when considered in connection with the accompanying drawings wherein:

FIGS. 1A-D are photographs showing the identification of a phage displaying peptide sequence of Sirt2 by plaque lift;

FIG. 2 is a photograph showing the analysis of the PCR product of the plaques by Southern Blot hybridization;

FIGS. 6 A-C are as follows.

FIG. 10 shows the matrix of reactivity between sets of clones coming from patients 1-12 (in rows) and sera from same patients (in columns), at this point (step 2 of Procedure 2), the matrix contains the results of the self-reactions: patients 1-10 have a specific self-reaction whereas patients 11 and 12 do not, Patients 11 and 12 are eliminated from the clone selection procedure;

FIG. 11 shows a matrix of reactivity between sources of clones and different sera ordered by reactivity; the clones from patient 2 react with sera from self (column 2) and patients 4 and 8; the clones from patient 3 react with sera from self (column 3) and patients 6 and 10, etc, note that the union of the set of clones coming from patients 2, 3, 5, 7 and 1 ensures that the chip made with these clones reacts with all patients;

DETAILED DESCRIPTION OF THE INVENTION

Figure 3:
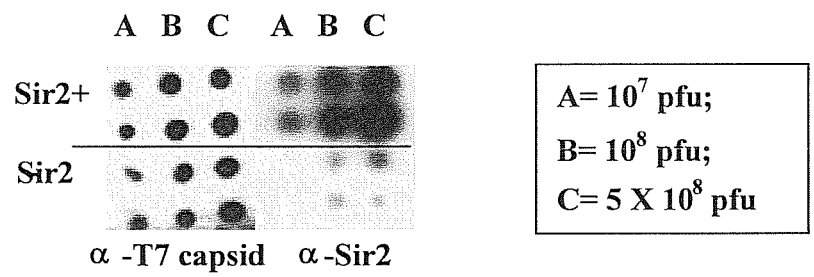
FIG. 3 is a photograph showing the Dot Blot analysis of Sirt2 positive plaques.
Figure 4:
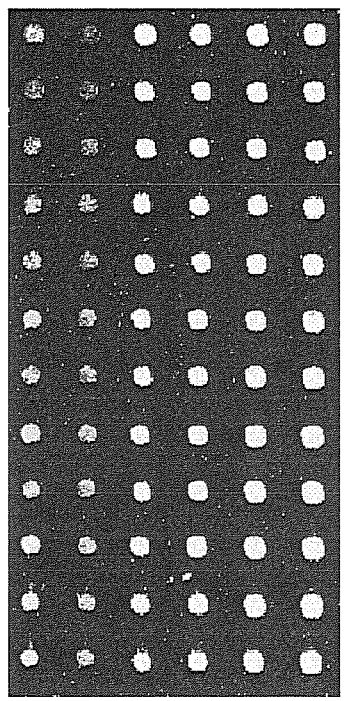
FIG. 4 is a photograph showing green and red labeled detection of serum antibodies indicative of the antibody reaction to the protein.
Figure 5A:
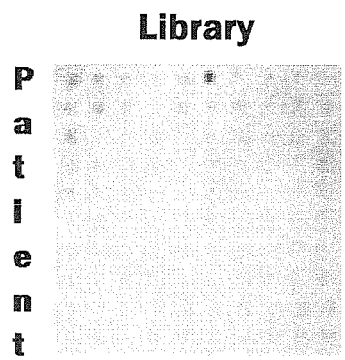
FIGS. 5 A-E are photographs showing the ECL detection of phagotopes selected with a breast cancer patient's serum.
Figure 5B:
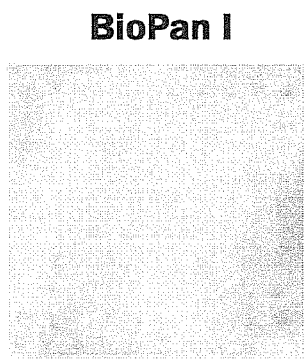
Figure 5C:
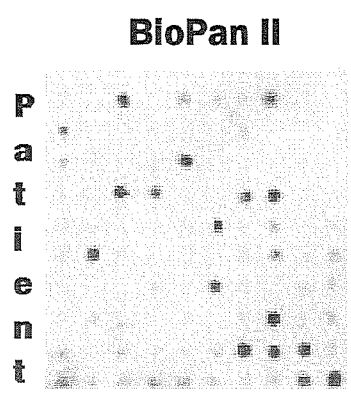
Figure 5D:
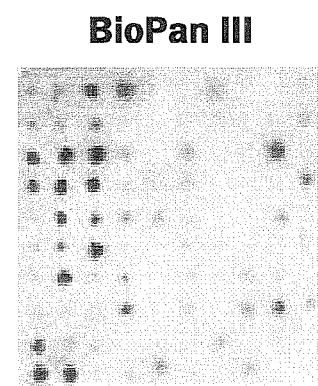
Figure 5E:
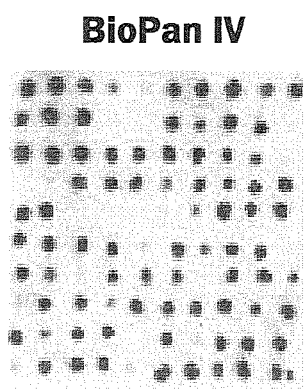

Generally, the present invention provides a method and markers for use in detecting disease and stages of disease. In other words, the markers can be used to determine the presence of disease without requiring the presence of symptoms.

The method and markers of the present invention can be used to diagnose the presence of a disease or a disease stage in a patient. The method of the present invention utilizes a detector device for detecting the presence of at least one marker in the serum of the patient. The benefit of such an analytical device is that the marker that is detected is one of a panel of markers. The panel of markers can include markers that are known to those of skill in the art and markers determined utilizing the methodology disclosed herein. The markers of the present invention can be used to detect diseases. Examples of diseases include, but are not limited to, gynecological sickness, such as endometriosis, ovarian cancer, breast cancer, cervical cancer, and primary peritoneal carcinoma. The method can also be used to identify overexpressed or mutated proteins in tumor cells. That such proteins are mutated or overexpressed presumably is the basis for the immune reaction to these proteins. Therefore markers identified using these methods could provide markers for molecular pathology as diagnostic or prognostic markers.

The method can also be used for immunotherapy targeted to a person's immunoprofile based on the arrays. For personalized immunotherapy, the reactivity to particular epitope clones can be correlated using sera from patients having cancer. Using a comprehensive panel of epitope markers that can accurately detect early stage ovarian cancer one can utilize these antigen as immuno-therapeutic agents personalized to the immuno-profile of each patient. When T-cells from the patient recognize antigen biomarkers, they get stimulated, activated and therefore produce an immune-response. Such reactivity demonstrates the potential of each antigen as a component of a vaccine to induce a T cell-mediated immune response essential for generation of cancer vaccines. Individuals scoring positive in the presymptomatic testing for OVCA can then be offered an anti-tumor vaccine tailored to their immunoprofile against a panel of tumor antigens.

The detector includes, but is not limited to an assay, a slide, a filter, a microarray, macroarray, computer software implementing the data analysis methods, and any combinations thereof. The detector can also include a two-color detection system or other detector system known to those of skill in the art.

By "bodily fluid" as used herein it is meant any bodily fluid known to those of skill in the art to contain antibodies therein. Examples include, but are not limited to, blood, saliva, tears, spinal fluid, serum, and other fluids known to those of skill in the art to contain antibodies.

By "biopanning", it is meant a selection process for use in screening a library (Parmley and Smith, Gene, 73:308 (1988); Noren, C. J., NEB Transcript, 8(1); 1 (1996)). Biopanning is carried out by incubating phages encoding the peptides with a plate coated with the proteins, washing away the unbound phage, eluting, and amplifying the specifically bound phage. Those skilled in the art readily recognize other immobilization schemes that can provide equivalent technology, such as but not limited to binding the proteins or other targets to beads.

By staging the disease, as for example in cancer, it is intended to include determining the extent of a cancer, especially whether the disease has spread from the original site to other parts of the body. The stages can range from 0 to 5 with 0 being the presence of cancerous cells and 5 being the spread of the cancer cells to other parts of the body including the lymph nodes. Further, the staging can indicate the stage of a borderline histology. A borderline histology is a less malignant form of disease. Additionally, staging can indicate a relapse of disease, in other words the reoccurrence of disease.

The term "marker" as used herein is intended to include, but is not limited to, a gene or a piece of a gene which codes for a protein, a protein such as a fusion protein, open reading frames such as ESTs, epitopes, mimotopes, antigens, and any other indicator of immune response. The marker can also be used as a predictor of disease or the recurrence of disease.

The present invention further includes a random peptide epitope (mimotope) that mimics a natural antigenic epitope during epitope presentation. Such mimotopes are useful in the applications and methods discussed above. Also included in the present invention is a method of identifying a random peptide epitope. In the method, a library of random peptide epitopes is generated or selected. The library is contacted with an anti-antibody. Mimotopes are identified that are specifically immunoreactive with the antibody. Sera (containing anti antibodies) or antibodies generated by the methods of the present invention can be used. Random peptide libraries can, for example, be displayed on phage (phagotopes) or generated as combinatorial libraries.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the various immunoglobulin diversity/joining/variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill can appreciate that such fragments can be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to polypeptides of this invention. Also, transgenic mice, or other organisms such as other mammals, can be used to express humanized antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay wherein an antibody specifically binds to an antigen. The immunoassay is characterized by the use of specific binding properties of a particular antibody to isolate, target, and/or quantify the antigen. In addition, an antigen can be used to capture or specifically bind an antibody.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions can require an antibody that is selected for its specificity for a particular protein. For example, polyclonal antibodies raised to modified β-tubulin from specific species such as rat, mouse, or human can be selected to obtain only those polyclonal antibodies that are specifically immunoreactive, e.g., with β-tubulin modified at cysteine 239 and not with other proteins. This selection can be achieved by subtracting out antibodies that cross-react with other molecules. Monoclonal antibodies raised against modified β-tubulin can also be used. A variety of immunoassay formats can be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction can be at least twice background signal or noise and more typically more than 10 to 100 times background.

A "label" or a "detectable moiety" is a composition detectable by spectroscopic, photochemical, biochemical, immunochemical, or chemical means. For example, useful labels include $^{32}$P, fluorescent dyes, iodine, electron-dense reagents, enzymes (e.g., as commonly used in an ELISA), biotin, digoxigenin, or haptens and proteins for which antisera or monoclonal antibodies are available, e.g., by incorporating a radiolabel into the peptide, or any other label known to those of skill in the art.

A "labeled antibody or probe" is one that is bound, either covalently, through a linker or a chemical bond, or noncovalently, through ionic, van der Waals, electrostatic, or hydrogen bonds to a label such that the presence of the antibody or probe can be detected by detecting the presence of the label bound to the antibody or probe.

The terms "isolated" "purified" or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "support or surface" as used herein, the term is intended to include, but is not limited to a solid phase which is typically a support or surface, which is a porous or non-porous water insoluble material that can have any one of a number of shapes, such as strip, rod, particle, including beads and the like. Suitable materials are well known in the art and are described in, for example, Ullman, et al. U.S. Pat. No. 5,185,243, columns 10-11, Kurn, et al., U.S. Pat. No. 4,868,104, column 6, lines 21-42 and Milburn, et al., U.S. Pat. No. 4,959,303, column 6, lines 14-31, which are incorporated herein by reference. Binding of ligands and receptors to the support or surface can be accomplished by well-known techniques, readily available in the literature. See, for example, "Immobilized Enzymes," Ichiro Chibata, Halsted Press, New York (1978) and Cuatrecasas, J. Biol. Chem. 245:3059 (1970). Whatever type of solid support is used, it must be treated so as to have bound to its surface either a receptor or ligand that directly or indirectly binds the antigen. Typical receptors include antibodies, intrinsic factor, specifically reactive chemical agents such as sulfhydryl groups that can react with a group on the antigen, and the like. For example, avidin or streptavidin can be covalently bound to spherical glass beads of 0.5-1.5 mm and used to capture a biotinylated antigen.

Signal producing system ("sps") includes one or more components, at least one component being a label, which generate a detectable signal that relates to the amount of bound and/or unbound label, i.e. the amount of label bound or not bound to the compound being detected. The label is any molecule that produces or can be induced to produce a signal, such as a fluorescer, enzyme, chemiluminescer, or photosensitizer. Thus, the signal is detected and/or measured by detecting enzyme activity, luminescence, or light absorbance.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as Q-beta replicase; promoters; dyes; fluorescers such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; photosensitizers; particles such as latex or carbon particles; suspendable particles; metal sol; crystallite; liposomes; cells, etc., which can be further labeled with a dye, catalyst, or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference. Preferably, at least one sps member is selected from the group consisting of fluorescers, enzymes, chemiluminescers, photosensitizers, and suspendable particles.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the sps can then include all the components required to produce a measurable signal, which can include substrates, coenzymes, enhancers, additional enzymes, substances that react with enzymatic products, catalysts, activators, cofactors, inhibitors, scavengers, metal ions, specific binding substance required for binding of signal generating substances, and the like. A detailed discussion of suitable signal producing systems can be found in Ullman, et al. U.S. Pat. No. 5,185,243, columns 11-13, which is incorporated herein by reference.

The label is bound to a specific binding pair (hereinafter "sbp") member which is the antigen, or is capable of directly or indirectly binding the antigen, or is a receptor for the antigen, and includes, without limitation, the antigen; a ligand for a receptor bound to the antigen; a receptor for a ligand bound to the antigen; an antibody that binds the antigen; a receptor for an antibody that binds the antigen; a receptor for a molecule conjugated to an antibody to the antigen; an antigen surrogate capable of binding a receptor for the antigen; a ligand that binds the antigen, etc. Binding of the label to the sbp member can be accomplished by means of non-covalent bonding as for example by formation of a complex of the label with an antibody to the label or by means of covalent bonding as for example by chemical reactions which result in replacing a hydrogen atom of the label with a bond to the sbp member or can include a linking group between the label and the sbp member. Such methods of conjugation are well known in the art. See for example, Rubenstein, et al., U.S. Pat. No. 3,817,837, which is incorporated herein by reference. Other sps members can also be bound covalently to sbp members. For example, in Ullman, et al., U.S. Pat. No. 3,996,345, two sps members such as a fluorescer and quencher can be bound respectively to two sbp members that both bind the analyte, thus forming a fluorescer-$sbp_1$:analyte:$sbp_2$-quencher complex. Formation of the complex brings the fluorescer and quencher in close proximity, thus permitting the quencher to interact with the fluorescer to produce a signal. This is a fluorescent excitation transfer immunoassay. Another concept is described in Ullman, et al., EP 0,515,194 A2, which uses a chemiluminescent compound and a photosensitizer as the sps members. This is referred to as a luminescent Oxygen channeling immunoassay. Both the aforementioned references are incorporated herein by reference.

The analysis of mRNA expression in tumors does not necessarily reveal the status of protein levels in the cancer cells. Other factors such as protein half-life and mutation can be altered without an effect on mRNA levels thus masking significant molecular changes at the protein level. Serum antibody reactivity to cellular proteins occurs in cancer patients due to presentation of mutated forms of proteins from the tumor cells or overexpression of proteins in the tumor cells. The host immune system can direct individuals to molecular events critical to the genesis of the disease. Using a candidate gene approach, experience has shown that the frequency of serum positively to any single protein is low. Therefore, to increase the identification of such autoantigens, a more global approach is employed to exploit immunoreactivity to identify large numbers of cDNAs coding for proteins that are mutated or upregulated in cancer cells.

In order to develop an effective screening test for early detection of ovarian cancer, cDNA phage display libraries are used to isolate cDNAs coding for epitopes reacting with antibodies present specifically in the sera of patients with ovarian cancer. The methods of the present invention detect various antibodies that are produced by patients in reaction to proteins overexpressed in their ovarian tumors. This is achievable by differential biopanning technology using human sera collected both from normal individuals and patients having ovarian cancer and phage display libraries expressing cDNAs of genes expressed in ovarian epithelial tumors and cell lines. Serum reactivity toward a cellular protein can occur because of the presentation to the immune system of a mutated form of the protein from the tumor cells or overexpression of the protein in the tumor cells. The strategy provides for the identification of epitope-bearing phage clones (phagotopes) displaying reactivity with antibodies present in sera of patients having ovarian cancer but not in control sera from unaffected women. This strategy leads to the identification of novel disease-related epitopes for diseases including, but not limited to ovarian cancer, that have prognostic/diagnostic value with additional potential for therapeutic vaccines and medical imaging reagents. This also creates a database that can be used to determine both the presence of disease and the stage of the disease.

The series of experiments disclosed herein provide direct evidence that biopanning a T7 coat protein fusion library can isolate epitopes for antibodies present in polyclonal sera. This also showed that the technology can be applied to direct microarray screening of large numbers of selected phage against numerous patient and control sera. This approach provides a large number of biomarkers for early detection of disease.

More specifically, the methods of the present invention provide four to five cycles of affinity selection and biopanning which are carried out with biological amplification of the phage after each biopanning, meaning growth of the biological vector of the cDNA expression clone in a biological host. Examples of biological amplification include but are not limited to growth of a lytic or lysogenic bacteriophage in host bacteria or transformation of bacterial host with selected DNA of the cDNA expression vector. The number of biopanning cycles generally determines the extent of the enrichment for phage that binds to the sera of patient with ovarian cancer. This strategy allows for one cycle of biopanning to be performed in a single day. Someone skilled in the art can establish different schedules of biopanning that provide the same essential features of the procedure described above.

Two biopanning experiments are performed with each library differentially selecting clones between control and disease patient sera. The first selection is to isolate phagotope clones that do not bind to control sera pooled from control women but do bind to a pool of disease patient serum. This set of phagotope clones represent epitopes that are indicative of the presence of disease as recognized by the host immune system. The second type of screening is performed to isolate phagotope clones that did not bind to a pool of control sera but do bind to an individual patient's serum. Those sets of phagotope clones represent epitopes that are indicative of the presence of disease.

Subsequent to the biopanning, the clones so isolated can be used to contact antibodies in sera by spotting the clones or peptide sequences of amino acids containing those encoded by the clones. After spotting on a solid support, the arrays are rinsed briefly in a 1% BSA/PBS to remove unbound phage, then transferred immediately to a 1% BSA/PBS blocking solution and allowed to sit for 1 hour at room temperature. The excess BSA is rinsed off from the slides using PBS. This step insures that the elution step of antibodies is more effective. The use of PBS elutes all of the antibodies without harming the binding of the antibody. Antibody detection of reaction with the clones or peptides on the array is carried out by labeling of the serum antibodies or through the use of a labeled secondary antibody that reacts with the patient's antibodies. A second control reaction to every spot allows for greater accuracy of the quantitation of reactivity and increases sensitivity of detection.

The slides are subsequently processed to quantify the reaction of each phagotopes. Such processing is specific to the label used. For instance, if fluorophore cy3-cy5 labels are used, this processing is done in a laser scanner that captures an image of the slide for each fluorophore used. Subsequent image processing familiar to those skilled in the art can provide intensity values for each phagotope.

The data analysis can be divided into the following steps:
1. Pre-processing and normalization.
2. Identifying the most informative markers
3. Building a predictor for molecular diagnosis of ovarian cancer and validating the results.

The purpose of the first step is to cleanse the data from artifacts and prepare it for the subsequent steps. Such artifacts are usually introduced in the laboratory and include: slide contamination, differential dye-incorporation, scanning and image processing problems (e.g. different average intensities from one slide to another), imperfect spots due to imperfect arraying, washing, drying, etc. The purpose of the second step is to select the most informative phages that can be used for diagnostic purposes. The purpose of the third step is to develop a software classifier able to diagnose cancer based on the antibody reactivity values of the selected phages. The last step also includes the validation of this classifier and the assessment of its performance using various measures such as specificity, sensitivity, positive predictive value and negative predictive value. The computation of such measures can be done on cases not used during the design of the chip in order to assess the real-world performance of the diagnosis tool obtained.

The pre-processing and normalization step is used for arrays using two channels such as Cy5 for the human IgG and Cy3 for the T7 control, the spots are segmented and the mean intensity is calculated for each spot. A mean intensity value is calculated for the background, as well. A background corrected value is calculated by subtracting the background from the signal. If necessary, non-linear dye effects can be eliminated by performing an exponential normalization (Houts, 2000) and/or LOESS normalization of the data and/or a piecewise linear normalization (see FIGS. 7 A-D). The values coming from each channel are subsequently divided by their mean of the intensities over the whole array. Subsequently, the ratio between the IgG and the T7 channels was calculated. The values coming from replicate spots (spots printed in quadruplicates) are combined by calculating mean and standard deviation. Outliers (outside +/−two standard deviations) are flagged for manual inspection). Single channel arrays are pre-processed in a similar way but without taking the ratios. This preprocessing sequence was shown to provide good results for all preliminary data analyzed.

The step of selecting the most informative markers is used to identify the most informative phages out of the large set of phages started with. The better the selection, the better is the expected accuracy of the diagnosis tool.

A first test is necessary to determine whether a specific epitope is suitable for inclusion in the final set to be spotted. The selection methods to be applied follow the principles of the methods successfully applied in (Golub et al., 1999; Alizadeh et al., 2000) and can be briefly described in the following.

Procedure 1

Figure 8A:
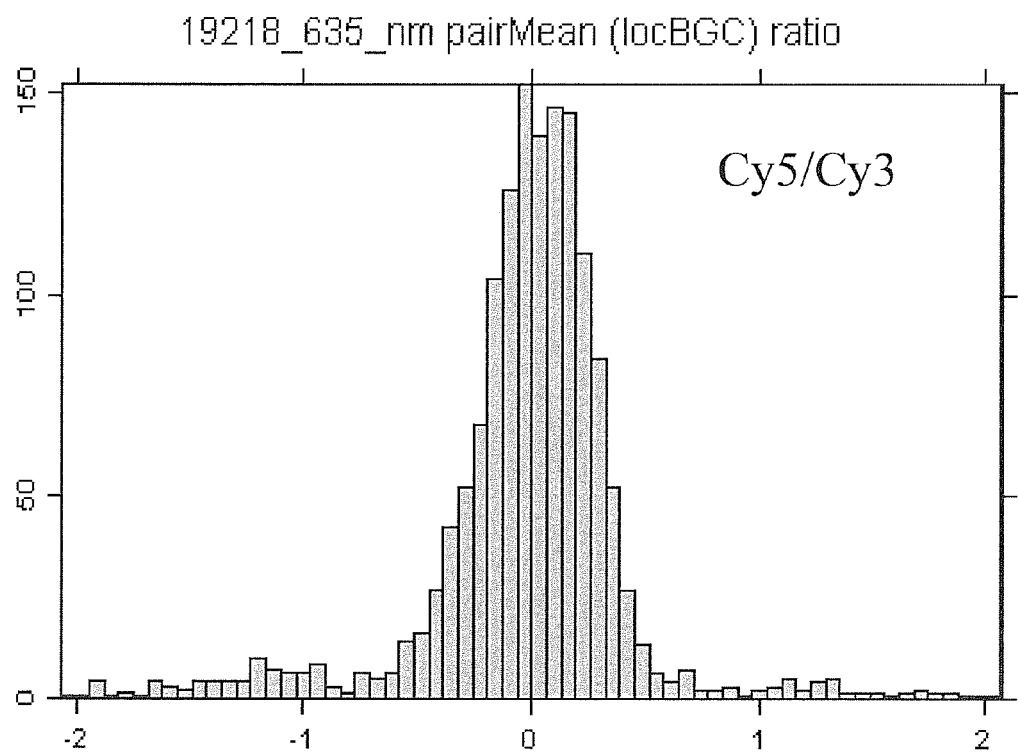
FIG. 8 shows an example comparison between the histogram of a control subject (19218) with a high but non-specific reaction to the left, and the histogram of a patient (19223), to the right; the histograms are calculated on the ratios of the background corrected mean intensity of the human IgG labeled with Cy5 vs. the background corrected mean intensity of the T7 labeled with Cy3.
Figure 8B:
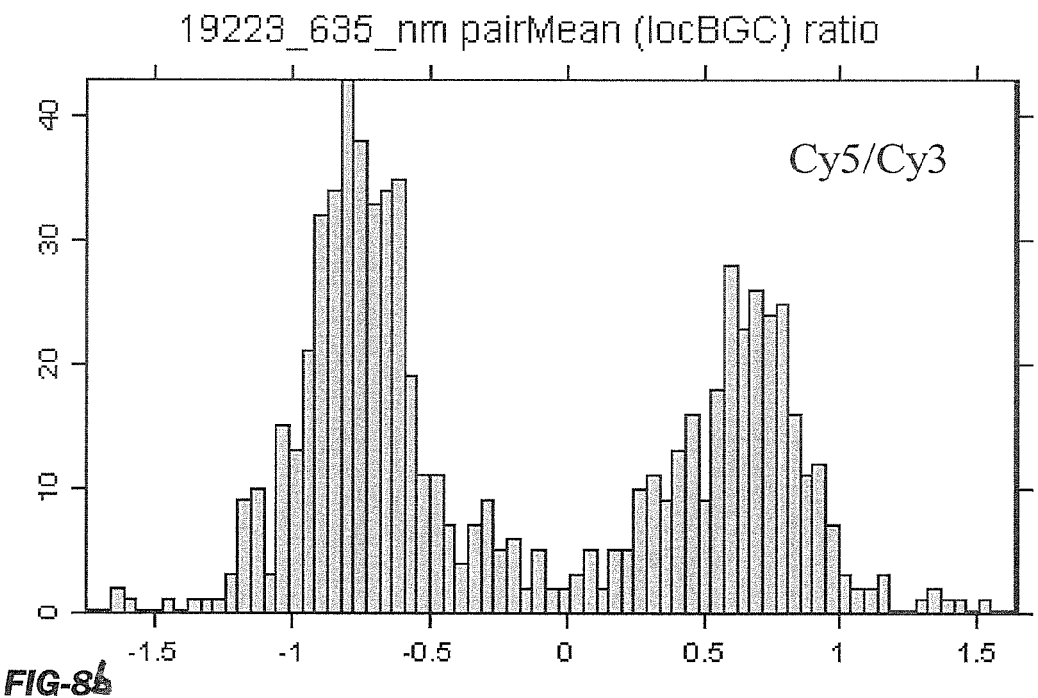
Figure 9A:
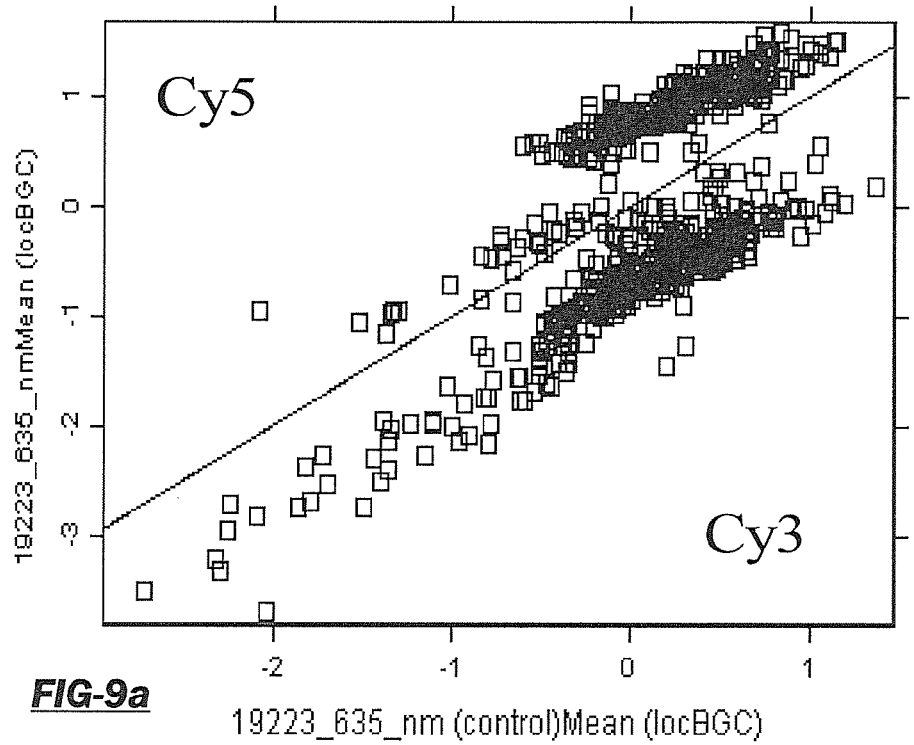
FIG. 9 shows a comparison between the scatterplot of a control subject (19218) with a strong but non-specific reaction and the scatterplot of a patient MEC1 (19223), the scattergrams plot the background corrected mean intensity of the human IgG labeled with Cy5 vs. the background corrected mean intensity of the T7 labeled with Cy3.
Figure 9B:
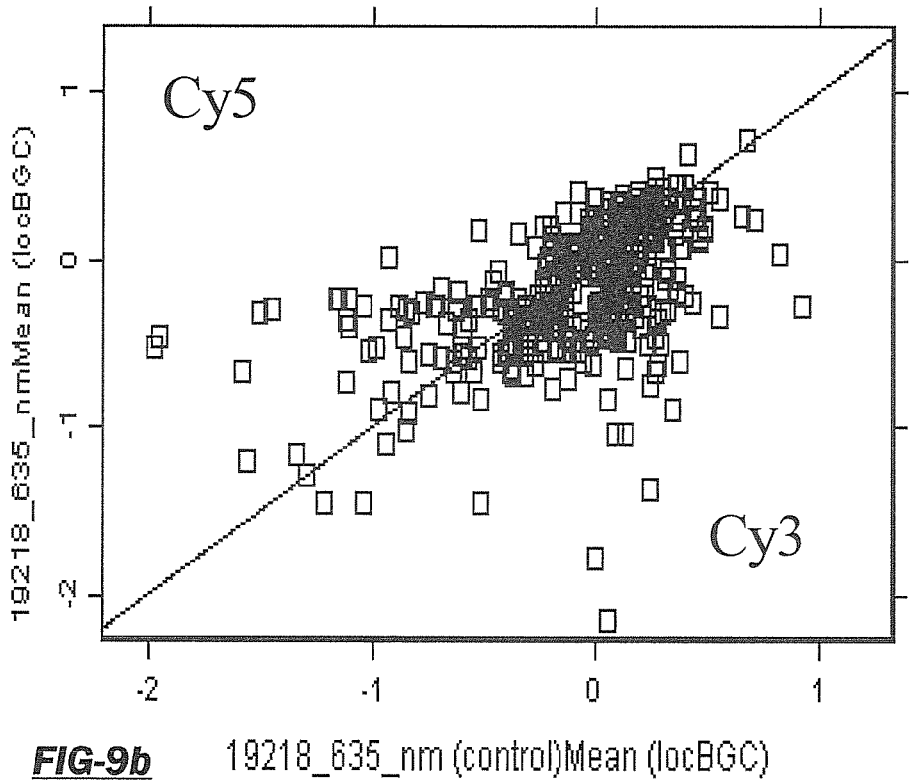

The procedure is initiated defining a template for the cancer case (FIG. 8). Unlike gene expression experiments where the expression level of a gene can be either up or down in cancer vs. healthy subjects, here one is testing for the presence of antibodies specific to cancer were tested for. Therefore, epitopes with high reactivity in controls and low reactivity in patients are not expected and the profile to the left in FIG. 8 is sufficient. Each epitope can have a profile across the given set of patients (FIGS. 9 A and B). The profile of each epitope is compared with the templates using a correlation-based distance. Those skilled in the art can recognize that the other distances may be used without essentially changing the procedure.

Figure 7A:
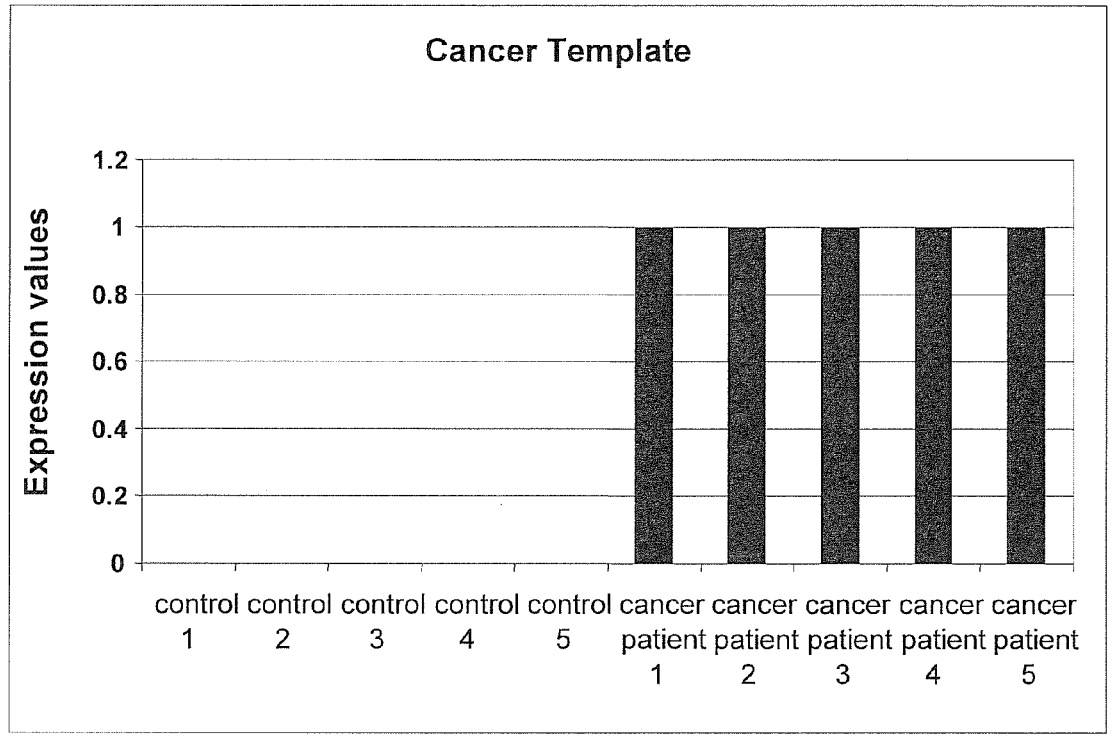
FIG. 7 shows the method of finding informative epitopes: The spot intensities are plotted on the vertical axis for 12 subjects (controls to the left and patients to the right) the template defined on the left (shown in blue) was used with a correlation distance, a correlation threshold of 0.8 selected the 46 epitopes shown here in red (out of the total of 4×96=384 shown here in yellow)
Figure 7B:
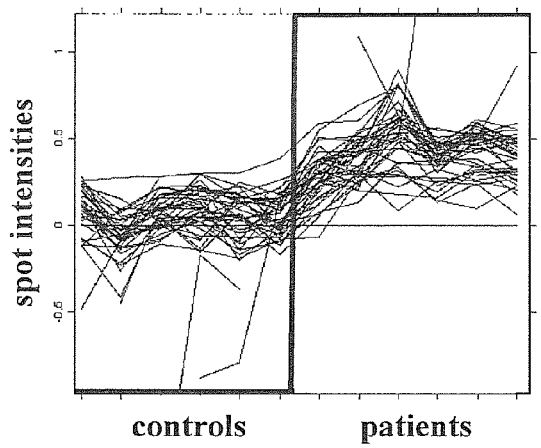

The epitopes are then ordered based on the similarity between the reference profile (FIG. 8) and their actual profile. FIG. 7 shows 46 epitopes found informative for a correlation threshold of 0.8. The final cutoff threshold is calculated by doing 1000 random permutations once the whole data set become available. Each such permutation moves randomly the subjects between the 'patient' and 'control' categories. Calculating the score of each epitope profile for such permutations allows us to establish a suitable threshold for the similarity (Golub et. al. 1999).

The technique follows closely the one used in (Golub, 1999). However, the technique can be further improved as follows. Firstly, this technique was shown to provide good results if most controls are consistent by providing the same type of reactivity. However, preliminary data showed that there are control subjects that show a non-specific reactivity with all clones (see FIG. 1b). While still clearly different from patients. FIG. 8 shows a comparison between the histogram profile of a control subject showing a non-specific reaction (19218) with and the profile of a patient (19223). FIG. 9 shows the scatterplots of the same subjects. While still clearly different from patients, such control subjects with a high non-specific reaction introduces spikes in the clone profile in the area corresponding to the control subjects (right left hanrd side of the template in FIG. 8). Such spikes decrease the score of the relevant clones making them more difficult to distinguish from the irrelevant ones. In order to reduce this effect, all control subjects with a non-specific response (i.e a unimodal distribution such as in the left panel of FIG. 7) were eliminated from the analysis leading to the epitope selection.

A second essential modification is related to the set of epitopes selected. There are rare patients who might react only to a small number of very specific epitopes. If the selection of the epitopes is done on statistical grounds alone, such very specific epitopes can be missed if the set of patients available contains only few such rare patients. In order to maximize the sensitivity of the penultimate test resulted from this work, every effort was made to include epitopes which might be the only ones reacting to rare patients. In order to do this, the information content of the set of epitopes is maximized while trying to minimize the number of epitopes used using the following procedure.

Procedure 2

Assume there are m patients and k controls. Select n random patients from the m available. For each of the n patients used for epitope selection, amplify (n×4 biopannings) and do self-reactions. Eliminate those patients/epitopes that do not react to self.

Make a chip with all available, self-reacting epitopes printed in quadruplicates. React this chip with all patients and controls (n+k antibody reactions). Eliminate controls with a non-specific reactivity. For the set of epitopes coming from a single patient, apply Procedure 1 to order the epitopes in the order of their informational content and select the ones that can be used to differentiate patients from controls.

Order the epitopes by their reactivity in decreasing order of the number of patients they react to. Scan this list from the top down, moving epitopes from this list to the final set. Every time a set of epitopes coming from a patient x is added to the final set, the patient x and all other patients that these epitopes react to are represented in the current set of epitopes. Repeat until all patients are represented in the current set of epitopes.

This procedure tries to minimize the number of epitopes used while maximizing the number of patients that react to the chip containing the selected epitopes.

The following example shows how this procedure works using a simple example. The matrix in FIG. 10 contains a row i for the clones coming from patient i and a column j for the serum coming from patient j. A serum is said to react specifically with a set of clones if the histogram of the ratios is bimodal (see subject 19218 in FIGS. 8 and 9). A serum is said to react non-specifically if the histogram of the ratio is unimodal (see subject 19223 in FIGS. 8 and 9). Furthermore, a serum might not react at all with a set of clones. If the serum from patient j reacts specifically with the clones from patient i, the matrix can contain a value of 1 at the position (i, j). The element at position (i, j) is left blank if the there is no reaction or the reaction is non-specific.

Each set of epitopes corresponding to a row of the matrix is pruned by sub-selecting epitopes according to Procedure 1. The rows are now sorted in decreasing reactivity (number of patients other than self that the clones react to). For instance, in FIG. 11, the clones from patient 2 react with sera from self (column 2) and patients 4 and 8. The clones from patient 3 react with sera from self (column 3) and patients 6 and 10, etc. The final set of clones was obtained from patients 2, 3, 5, 7 and 1 (reading top-down in column 1). Clones coming from patients 8, 9 and 10 are not included since these patients already react to clones coming from other patients. This set ensures that the chip made with these clones reacts with all patients in this example.

Procedure 3

Arrays using two channels such as Cy5 for the human IgG and Cy3 for the T7 control are processed as follows. The spots are segmented and the mean intensity is calculated for each spot. A mean intensity value is calculated for the background, as well. A background corrected value is calculated by subtracting the background from the signal. The values coming from each channel are normalized by dividing by their mean. Subsequently, the ratio between the IgG and the T7 channels are calculated and a logarithmic function is applied. The values coming from replicate spots (spots printed in quadruplicates) are combined by calculating mean and standard deviation. Outliers (outside +/−two standard deviations) are flagged for manual inspection. Someone skilled in the art can recognize that various combinations and permutations of the steps above or similar could replace the normalization procedure above without substantially changing rest of the data analysis process. Such similar steps include without limitation taking the median instead of the mean, using logarithmic functions in various bases, etc.

The histogram of the average log ratio is calculated. If the histogram is unimodal (e.g subject 19223 in FIG. 7), there is no specific response. If the histogram is clearly bimodal (e.g. subject 19218 in FIG. 7), there is a specific response. All 25 subjects analyzed so far fell in one of these two categories or had no response at all. A mixed probability model is used in less clear cases to fit two normal distributions as in (Lee, 2000). If the two distributions found under the maximum likelihood assumption are separated by a distance d of more than 2 standard deviations (corresponding to a p-value of approximately 0.05), there is a specific response. If the distance is less than 2 standard deviations, the response can be considered as not specific. The preliminary data analyzed so far showed a very good separation of the distributions for the patients.

Once the chosen clones are spotted on the final version of the array, a number of sera coming from both patients and controls can be tested. These sera come from subjects not used in any of the phases that lead to the fabrication of the array (i.e. not involved in clone selection, not used as controls, etc.). Each test was evaluated using Procedure 3 above. The performance on this validation data can be reported in terms of PPV, NPV, specificity and sensitivity. Since these performance indicators are calculated on data not previously used, they provide a good indication of the performance of the test for screening purposes for the various categories of patients envisage in the general population.

The present invention also provides a kit including all of the technology for performing the above analysis. This is included in a container of a size sufficient to hold all of the required pieces for analyzing sera, as well as a digital medium such as a floppy disk or CDROM containing the software necessary to interpret the results of the analysis. These components include the array of clones or peptides spotted onto a solid support, prewashing buffers, a detection reagent for identifying reactivity of the patients' serum antibodies to the spotted clones or peptides, post-reaction washing buffers, primary and secondary antibodies to quantify reactivity of the patients serum antibodies with the spotted array and methods to analyze the reactivity so as to establish an interpretation of the serum reactivity.

A biochip for detecting the presence of the disease state in a patient's sera is provided by the present invention. The biochip has a detector contained within the biochip for detecting antibodies in a patient's sera. This allows a patient's sera to be tested for the presence of a multitude of diseases or reaction to disease markers using a single sample and the analysis can be conducted and analyzed on a single chip. By utilizing such a chip this lowers the time required for the detection of disease while also enabling a doctor to determine the level of disease spread or infection. The chip, or other informatics system can be altered to weigh the results. In other words, the informatics can be altered to adjust the levels of sensitivity and/or specificity of the chip.

The present invention is well suited for providing useful information regarding the efficacy of pharmaceuticals at treating disease. Specifically, the present invention is well suited in measuring the effects of drugs and other medications based on the above-identified markers. The present invention determines the minimum level of a pharmaceutical needed to achieve therapeutic benefits. Thus, the present invention is useful in determining effective treatment of various diseases and illnesses. The results of the analysis can be utilized to determine if the treatment is effective or if such treatment needs to be altered.

Further, the treatment can be altered based upon the markers detected. For example, the treatment can be specifically designed based upon the markers identified. In other words, the therapy can be altered to most suitably treat the identified markers, such that the treatment is designed to most efficiently treat the identified marker. The ability to adjust the therapy enables the treatment to be tailored to the person being treated's needs. The treatments that can be used range from vaccines to chemotherapy.

The markers of the present invention can also be used for immuno-imaging. Immuno-imaging is a process in which antibodies to a specific antigen are labeled such that the label can be detected externally. Examples of externals detectors include, but are not limited to, x-rays, MRI, CT scan, and PET scans. The imaging functions because an imaging reagent containing the labeled antibody is administered to a patient.

The above discussion provides a factual basis for the use of the combination of markers and method of making the combination. The methods used with a utility of the present invention can be shown by the following non-limiting examples and accompanying figures.

EXAMPLES

Example 1

The purpose of this study is to clone epitopes that are recognized by sera from women with ovarian cancer but not recognized by normal sera from unaffected women. As these epitopes are cloned, protein array assays are developed capable of detecting ovarian cancer at an early stage by analyzing antigens recognized in the sera of at risk women. Toward this end, individual sera were screened using these protein biochips to determine the antibody reactivity to each protein epitope. Antibody reactivity is detected that does not appear in control sera. The patients and control sera obtained for this study were used to calibrate the protein biochips and identify the most informative epitope-clones. The women were monitored for the appearance or reappearance of antibody reactivity and its correlation with tumor burden. By following the serum reactivity to tumor reactive new epitopes on the arrays of the phage display cDNA clones, the analysis of sera from women after their initial diagnosis and semiannually thereafter allows the determination of the markers in predicting tumor recurrence.

Some of the markers can be predictive of recurrence, and thus can be used to correlate specific ovarian tumor types (using the World Health Organization Histological Classification of Ovarian Tumors), also the tumor grade (where appropriate, since not all tumors all graded), and the surgical stage. This can be done by review of the pathological material (glass slides, patient records, and surgical pathology reports). Certain currently accepted biomarkers of research interest such as Her-2 neu and other can also be included in the new protein biochips in order to compare the sensitivity and specificity of the new and existing immunohistochemical technologies. Testing for Her-2 neu and other biological markers is done by the immunoperoxidase method using formalin fixed, paraffin embedded tumor tissues.

For the purpose of comparison to the ovarian cancer patients, one can analyze serum markers in women in good health who do not have ovarian or any other type of cancer. These control subjects should not have a family history of ovarian cancer or breast cancer. Because some serum markers such as CA125 levels are increased in endometriosis, uterine leiomyoma, pelvic inflammatory disease, early pregnancy, and benign cysts, control subjects should be free of these conditions as well.

The series of experiments provides direct evidence that biopanning a T7 coat protein fusion library can isolate epitopes for antibodies present in polyclonal sera. This also showed that the technology can be applied to direct microarray screening of large numbers of the selected phage against numerous patient and control sera. This approach provides a large number of biomarkers for early detection of ovarian cancer. The likelihood of success of this approach is increased by the fact that the mRNA for human Sirt2 is present in cells at very low abundance in human brain RNA thus indicating that clones can be isolated for rare RNA transcripts by this approach.

To further demonstrate the feasibility of these methods for differential detection of epitopes between test and control sera, four cycles of biopanning of a commercial Novagen breast tumor cDNA library were performed using a serum sample from a breast cancer patient and a control serum sample from a woman without cancer. 100 plaques were picked from each biopanning. Analysis of 100 plaques from the initial library and each successive biopanning were amplified in microtitre plates and the lysates cleared by centrifugation. One half microliter of each sample was spotted onto nitrocellulose filters and immunodetection performed using the breast cancer patient serum at 1:20,000 dilution (FIG. 5). Clear enrichment during biopanning is seen as was observed above with the anti-Sirt2 rabbit serum. As seen in FIG. 6 (using randomly picked plaques from BP 4) the filters contacted with the control serum on the left panels demonstrate weaker spot intensity as compared to a duplicate filter of the same clones on the right that was contacted with the patient serum. Approximately 65% of the phage selected for reactivity to the patient's serum were more than 3-fold more reactive with the patient's serum than with the control serum as determined by scanning densitometry.

Figure 6A:
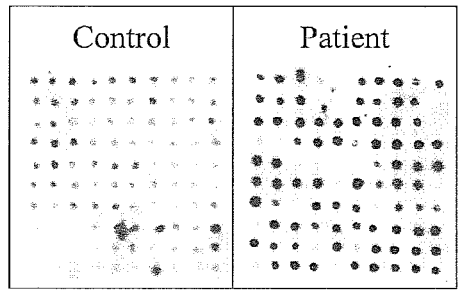
FIG. 6A is a photograph showing the comparison of serum reaction of control and breast cancer patient with phagotopes from BP4.
Figure 6B:
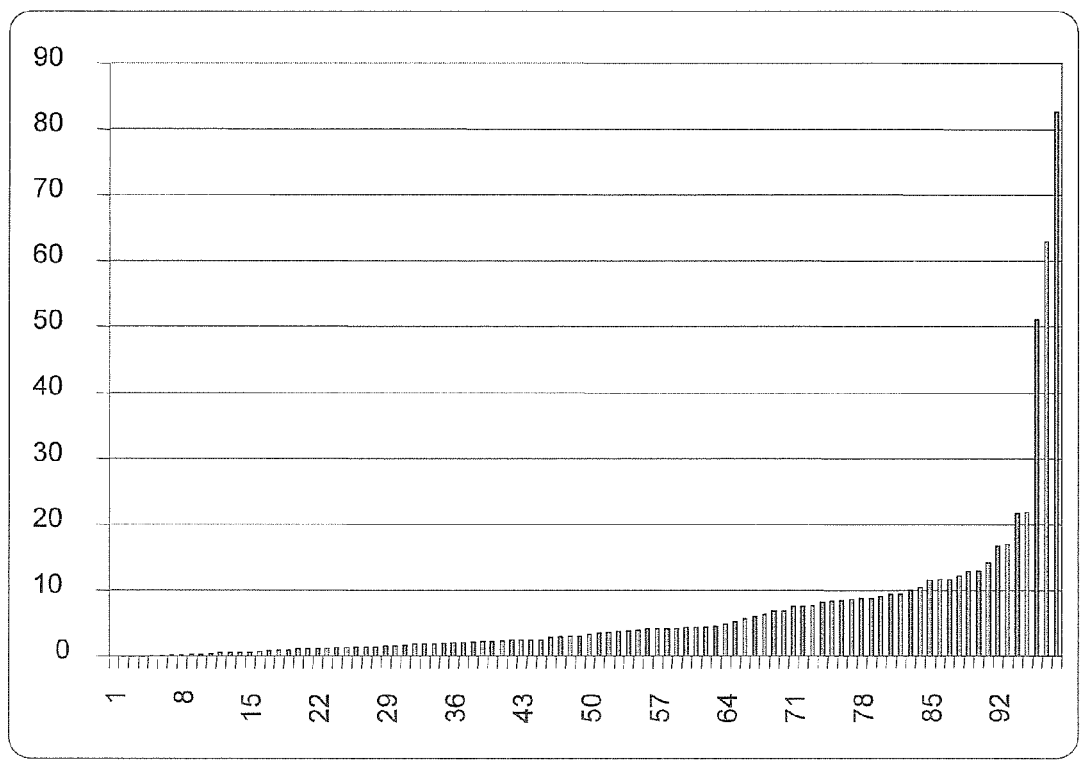
FIG. 6B is a graph of the BP4 filters which were scanned thereby showing the ratio of the pixel densities plotted in rank order.

FIG. 6A shows a comparison of serum reaction of control and breast cancer patient with phagotopes from BP4. FIG. 6B shows the BP4 filters that were scanned and the ratio of the pixel densities plotted in rank order.

This experiment demonstrates that one can differentially detect the epitopes for which the process is selecting, i.e. those bound to protein G-agarose beads in association with antibodies in the patient's serum and not the control serum. Someone skilled in the art can recognize that other solid supports for biopanning could replace the protein-G beads without substantively changing the biopanning process. These data also indicate that the selection is imperfect. Not all of the selected phagotopes are more reactive with the patient's serum that the control serum. Therefore, the identification of the most informative phagotopes requires analysis of the reactivity with multiple, individual patients' sera tested at various serum dilutions.

The immune reactivity to human tumors recognizes changes in the expression levels and mutation status of proteins in the tumor cells. These types of immunological reactivity are not observed in sera from control subjects. The antibody titer to tumor specific epitopes can be proportional to the tumor burden. The immune reactivity to human tumors can be used diagnostically and prognostically to predict the presence and behavior of human tumors such as tumor recurrence. Serum reactivity to single proteins tends to incompletely identify tumor bearing patients and therefore more robust methods are necessary to accurately identify tumor occurrence and recurrence. Whole genome-based proteomics such as the technology and data analysis methods embodied in the application can more comprehensively identify those proteins recognized by the host immune system.

Those of skill in the art are familiar with the construction of cDNA libraries and there are numerous published numerous papers on isolation of cDNAs from human cells in culture using this technology (Chiao, et al., 1992; shin et al., 1993; Buettner et al., 1993; Kim et al., 1996; Deyo et al., 1998; Bauer et al 1998). cDNA libraries can be prepared from ovarian cancer cell lines or from ovarian tumor tissue. Tumor tissue cDNA library can be prepared from a pool of mRNA preparations from each of the different stages of cancer to increase the diversity of clones in the library.

Methods mRNA from one ovarian cancer cell line, SKOV3 and ovarian tumor tissues, was copied into cDNA and libraries prepared. Tumor tissue in excess of that needed for pathological evaluation was obtained by informed consent from ovarian cancer patients.

Sera was obtained from 1) ovarian cancer patients at the time of diagnosis and at six month intervals during the follow up physician visits; 2) unaffected women for control sera.

T7 cDNA phage display expression libraries are prepared for biopanning experiments, to select phage bearing epitopes ie phagotopes that are recognized by sera from women with ovarian cancer but not recognized by normal sera from unaffected women. For the biopanning process, sera from women in the control group was pooled to avoid individual variations unrelated to the presence of ovarian cancer.

The selection of the most informative epitopes was done by comparing the immune reaction profile of each individual epitope with templates defined for each disease stage. Several distances and information entropy measures were used. Several predictors were constructed based on three selected machine learning techniques using only a part of the available data. Specificity, sensitivity, positive predicted value and negative predicted value were calculated for each such classifier. The validation of the predictors and the selection of the best predictor was done by cross-validation on cases that have not been used during the predictor construction.

For example, to develop an effective screening test for early detection of ovarian cancer, cDNA phage display libraries were used to isolate cDNAs coding for epitopes reacting with antibodies present in the sera of patients with ovarian cancer. Screening of T7 phage cDNA library with serum containing polyclonal antibodies against a known protein, leads to the enrichment of one particular phage clone (which displays the peptide sequence recognized by the antibody on its coat) after several rounds of biopanning. Serum containing polyclonal antibodies were raised against a C-terminal 12 amino acid peptide from the human homologue of the yeast SIRT2 protein and screened against a T7 phage human brain cDNA library. This library was used because the Sift2 transcript is expressed in human brain. Preimmune rabbit serum was bound to protein-G agarose beads and $6 \times 10^{10}$ phage were added to the beads. The unbound phage were then bound to protein-G agarose beads to which the Sirt2p antibody was previously bound. The nonspecifically bound phage were washed away with PBS and the specifically bound phage eluted with 1% SDS. T7 phage is stable in this solution. These phage are diluted to reduce the SDS concentration and used to infect bacteria for amplification and another cycle of biopanning. Table 1 shows the value of the titer of the T7 phage library after each cycle of biopanning. This table reveals that the titer of the eluate after each round of biopanning increased with each successive cycle of antibody selection.

*E. coli* BLT5615 infected with amplified phage library after biopanning 1-4 were plated onto LB-Agar plates and plaque lifts were performed for all the individual plates. The plaque lift filter membranes were then hybridized with a $P^{32}$-labeled Sirt2 cDNA probe. The percentage of positive plaques (number of positive plaques/total number of plaques×100) as determined for each plates labeled BP1-4, FIG. 1 increased with each successive cycle of biopanning. For BP1 and BP2 the percentage of positive plaques was negligible. For BP3 and BP4, percentage of positive plaques was 1.7% and 8.6% respectively.

In order to confirm that those positive plaques contain phage clones displaying the peptide sequence of Sirt2, 50 plaques were randomly picked up and PCR amplified each insert using T7 coat protein forward primer (5'TCTTCGC-CAGAAGCTGCAG3' (SEQ ID NO: 1)) and T7 coat protein reverse primer (5'CCTCCTTTCAGCAAAAAACCCC3' (SEQ ID NO: 2)). Filter hybridization was performed using the same Sirt2 cDNA probe as above. As shown in FIG. 2, 7 out of 50 plaques (14%) hybridized to the Sirt2 probe, a frequency similar to that observed in the plaque lifts. Plaques positively reacting with the Sirt2 probe were picked and also hybridized on Southern Blots of PCR product.

Sirt2 positive plaques (upper two rows) and Sirt2-negative plaques (lower two rows) were chosen and 1 µl (pfu indicated at left) of each amplified phage clone was spotted onto the nitrocellulose membranes which were then treated as if they were standard immunoblots using the rabbit polyclonal Sirt2 antibody (right panel) or a mouse monoclonal antibody to the T7 capsid protein (left panel). The rabbit polyclonal antibody provides a sample for testing as if it were a patient's serum using the Sirt2 protein as a model. The Sirt2 antibody in the rabbit polyclonal serum reacted specifically with the Sirt2 phage. The identity of the phage was confirmed by direct PCR sequence analysis of the cDNA inserts in two independent Sirt2 positive phage. Thus phage expressing the epitope to which the antiserum was directed were isolated and distinguished from other phage.

Microarrays were spotted using Sirt2 T7 clones and other T7 clones that do not express Sirt2. These arrays were used to analyze a mixture of Cy5-labeled (red) rabbit Sirt2-immunized serum and Cy3-labeled (green) T7 coat protein antibody (Novagen) added to the pre-immune rabbit serum. The scanned two-color image clearly shows specific detection of the Sirt2-expressing T7 clones by the anti-Sirt2 antibody. The Sirt2 expressing clones appear yellow because they bind both the red-labeled antibody to a rabbit immunoglobulin G protein and the green-labeled anti-T7 capsid 10B antibody. The non-Sirt2-expressing T7 clone are green as they only bind to the Cy3-labeled anti-T7 antibody. This development of detection of protein epitopes in bacteriophage bodes well for the applicability of phage arrays to the detection of low abundance species and weak binders. The spots in the image are approximately 100 microns in diameter.

The following is an example of the preparation of a tumor reactive cDNA expression library: Ovarian cancer cells were grown in monolayer culture. Cells or fresh tumors from patients were lysed by the addition of 3 ml of TRIZOL® reagent and the homogenized sample was incubated for five minutes at room temperature. Chloroform, 0.6 ml, was added and the mixture was shaken vigorously for 15 seconds and then incubated at room temperature for 2-3 minutes. The extract was centrifuged at 12,000×g for 30 minutes at 4° C. Following centrifugation, the mixture was separated a lower red, phenolchloroform phase, an interphase, and a colorless aqueous phase. Aqueous phase was transferred to a fresh tube and total RNA was precipitated by adding 1.5 ml of isopropanol. The mixture was incubated at room temperature for ten minutes and was centrifuged at 12,000g for 30 minutes at 4° C. The supernatant was discarded and the RNA pellets were washed by adding 3 ml of 75% ethanol. The samples were centrifuged at 14,000×g for 15 minutes. The RNA pellet was air-dried and was dissolved in RNase-free water.

mRNA was isolated from total RNA following Oligotex® mRNA spin column protocol. Total RNA, 0.5 mg, was dissolved in 500 µl of RNase-free water and 500 µl of binding buffer and 30 µl of Oligotex® suspension was added. The contents were mixed thoroughly, incubated for three minutes at 70° C. in a water-bath, and then at room temperature for 10 minutes. The Oligotex®:mRNA complex was pelleted by centrifugation for 2 minutes at 14,000×g and the supernatant was discarded. The Oligotex®:mRNA pellet was resuspended in 400 µl washing buffer by vortexing and pipetted onto a spin column placed in a 1.5 ml microcentrifuge tube. The samples were centrifuged at maximum speed for one minute and the flow-through discarded. The spin column was transferred to a new RNase-free 1.5 ml microcentrifuge tube. Elution buffer at 70° C. was then added to the column. Poly (A)$^+$mRNA was eluted, quantitated by UV spectroscopy and the process of poly A selection repeated one more time to further reduce contamination with ribosomal RNA. Twice poly A selected mRNA was stored at −70° C. for use in library preparation.

Novagen's OrientExpress cDNA Synthesis and Cloning systems were used for the construction of ovarian cancer cDNA T7 phage libraries. For first-strand cDNA synthesis, OrientExpress Random Primer System was used to ensure representation of both N-terminal and C-terminal amino acid sequences.

Ten ml of LB/carbenicilln medium were inoculated with a single colony of BLT5615 from a freshly streaked plate. The mixture was shaken at 37° C. overnight. Ten ml of the overnight culture was added to 90 ml of LB/carbenicillin medium and was allowed to grow until $OD_{600}$ reaches 0.4-0.5.IPTG (1 mM), M9 salts (1×) and glucose (0.4%) can be added and the cells were allowed to grow for 20 minutes. An appropriate volume of culture was infected with phage library at MOI of 0.001-0.01 (100-1000 cells for each pfu). The infected bacteria were incubated with shaking at 37° C. for one to two hours until lysis is observed. Glycerol (0.02%), PMSF (0.02M) was added to the cell lysate to block proteolysis of the capsid fusion proteins. The phage were centrifuged at 8000×g for 10 minutes. The supernatant was collected and was stored at 4° C. The lysate was titered by plaque assay under standard conditions. The libraries are stored after purification by polyethylene-glycol precipitation and ultracentrifugation through a stepwise CsCl gradient.

Using this approach, applicants have constructed the first library. Using twice poly A selected mRNA from SKOV3 cells a T7 select cDNA library was prepared containing 1.8× $10^7$ initial plaques after packaging. This representation is comparable to the clonal representation of the commercial libraries purchased. This library has been amplified and stored in aliquots in two −70° C. freezers.

Patients' sera were obtained from multiple institutions for this project. Three outside institutions have agreed to provide ovarian cancer patient sera and the associated medical record information in anonymized form. Dr. Steven Witkin from the Weill Medical College of Cornell University provided 46 patient serum samples and 27 controls. Dr. Karen Lu from the M.D. Anderson Cancer Center can provide 60 serum samples. Dr. David Fishman from the Northwestern University Comprehensive Cancer Center provided 35 serum samples of patients who have been followed from time of diagnosis.

The ideal sera for the clone biopanning studies come from women just before or after surgery and prior to chemotherapy. Follow up sera were obtained after chemotherapy and are important to determine whether the penultimate protein array technology can detect tumor recurrence.

In addition, a supply of tumor tissue was required for the preparation of mRNA for cDNA library production and gene expression studies using samples from patients. This tissue was harvested within 20 minutes of surgical excision from the patients. This requires the coordinated effort of the gynecologic surgeons and pathologists. Patients at the time of their original surgery or prior to chemotherapy were accrued for serum collection. If tumor tissue is available in excess of that needed for routine pathologic evaluation, that tissue was used for RNA preparation for mRNA expression studies associated with this study. Sections from tissue blocks were also acquired for the purpose of expression studies of proteins in the patients' tumors. Patients at follow up visits to the OB/GYN clinics were also subjects for serum acquisition. These latter patients can be at a time of recurrence or not. This allows the observation of the reappearance of serum markers in the event of tumor recurrence. Serum was obtained from eligible patient-subjects during scheduled clinic visits. The initial serum acquisition occurs prior to surgery, if possible, or if post surgery, prior to chemotherapy. A single red top 7 cc vial of blood was obtained during normal phlebotomy and the serum isolated after clotting. Serum continues to be collected from these patients during follow up visits for up to five years or until ovarian cancer recurrence. Tumor tissue in excess of that required for pathological analyses were acquired at the time of surgery for the preparation of tumor RNA needed for antibody screening. Unaffected volunteers (controls) were be recruited through community outreach activities.

The Biopanning Process

Steps in the Biopanning Process:

Affinity selection with sera from normal individuals: Twenty-five µl of Protein G Plus-agarose beads were taken in 0.6 µl eppendorf tube and were washed two times with 1×PBS. Washed beads were blocked with 1% BSA at 4° C. for one hour. The beads were then incubated at 4° C. for one hour with 250 µl of pooled sera at a dilution 1:20 from 20 control women. After three hours of incubation, beads were washed three times with 1×PBS and then incubated with phage library (~$10^{10}$ phage particles). After incubation, the mixture was centrifuged at 3000 rpm for two minutes to remove phage nonspecifically bound to the beads and the supernatant (phage library) was collected for immunoscreening.

Fresh protein G Plus agarose beads were placed into a 0.6 ml eppendorf tube and were washed two times with 1×PBS. Washed beads were blocked with 1% BSA at 4° C. for one hour. The beads were then incubated at 4° C. for three hours with 250 µl of sera at a dilution 1:20 from patients with ovarian cancer. After this incubation, the beads were washed three times with 1×PBS and were incubated with phage library supernatant from above (termed as Biopanning 1 (BP1)) collected for immunoscreening at 4° C. for overnight (shorter times of incubation have not proven successful using model antibody systems). After incubation, the mixture was centrifuged at 3000 rpm for two minutes and supernatant can be discarded. Beads were washed three times with 1×PBS. To elute the bound phage 1% SDS was added to the washed beads and the mixture was incubated at room temperature for ten minutes. The bound phage were removed from the beads by centrifugation at 8000 rpm for seven minutes. Eluted phage were transferred to liquid culture for amplification (100 µl elution to 20 ml culture). Four rounds of affinity selection and immunoscreening was carried out with amplified phage obtained after each biopanning. The number of biopanning cycles generally determines the extent of the enrichment for phage that binds to the sera of patient with ovarian cancer. This process allows for one cycle of biopanning to be performed in a single day.

In the past serum markers have been identified using SEREX technology that detected only a few gene products at a time. The biopanning approach developed can isolate large numbers of target epitopes. These epitopes are displayed on the surface of bacteriophage as in-frame fusion proteins with the T7 phage capsid protein and can be analyzed in large numbers by arraying the selected phage on filter paper or glass slides (protein microarrays). The method isolates large numbers of phage that react with antibodies from pooled patient sera but not with normal sera.

The titer of the T7 phage library obtained after amplification of each Biopanning (BP1-4) eluate was determined by plaque assay. *E. Coli* BLT5616 were infected with the primary unamplified phage from biopanning (BP3-4) and plagued to limiting dilution onto LB/carbenicillin plates (150 mm×15 mm petri dish) so that sufficient numbers of single plaques can be isolated to obtain 12×96 well plates for arraying. The plates were incubated at 37° C. for 3-4 hours until the plaques are visible and then picked for amplification in the 12×96 well plates. After two hours, lysis of the host bacteria occurs in the wells of the 96-well plates. One well of each plate was uninfected as a control. Five 96 well plates of 200 µl phage lysates were clarified by centrifugation of the phage. The phage were cleared by whole plate centrifugation before robotic spotting in triplicate onto filters or glass slides. Excess reactivity in the surface area of the slide not spotted with phage was blocked using BSA, 1% solution in PBS for 60 minutes, followed by washing in water three times. After blocking the arrays on glass slides or filters were blocked with 1% BSA in PBS and incubated with a various dilutions of each of the individual controls and patient's sera spotted in triplicate or more for each dilution of serum. Serum antibodies binding to recombinant proteins expressed in the surface of the T7 bacteriophage were detected by incubation a Cy5-labeled anti-human IgG goat antiserum and visualized and quantified using GenePix® and ImaGene® software in a 4000B array scanner (AXON Instrument). As positive control for each spot a Cy3-labeled antibody for the T7 capsid protein was used. The ratio of the fluorescence intensity for the human antibodies were normalized to the T7 capsid antibody reactivity. Initial testing of phage solutions were performed on a spotting robot.

The optimal number of subtractive biopannings for each serum sample is determined by picking individual phage clones, and then testing the antibody reactivity for the serum used in the biopanning against those clones, (referred to as its self reaction). Plates of 96 clones were picked for each patient's biopanning at cycles 3, 4, and 5 which were then tested for the binding of the phage clones to antibodies in that serum, in a "self-reaction". Antibody binding was detected by spotting the filters with a 96 pin head on a Biomek robot or detected on glass slides of microarrays of phagotopes. The filters were then treated like a western blot by blocking with 1% dry milk powder in PBS and adding diluted serum. After rocking for 2 hours the filter is washed and reacted with an anti-human IgG antibody link to horseradish peroxidase (HRP) and detected by ECL® (Enhanced Chemical Luminescence). From the clones isolated from one patient, (designated patient #1) a total of 480 plaques were picked from that serum at biopanning 4. Biopanning four was chosen because about 35% of the clones bound antibodies from that patient's serum. Serum reactivity of the phagotopes with the patient's serum was detected at a 1:10,000 dilution indicating a very high titer of the IgG molecules that reacted with the epitopes (self reaction with 480 clones). Reactivity to these clones is detected at similar dilutions using the clones arrayed on glass slides as an alternative solid support.

When the serum reactivity with other patients (non-self reactions) was analyzed using replicates of the robotically spotted filters, reactivity was found in some patients again at a dilution of 1:10,000 (FIG. 1*b*). Other patients required a 1:3000 dilution of the serum for detection of the reactive clones Table 1). Patients #23 reacted quite strongly while patient #16 reacted more weakly (FIG. 1*b* and Table 1). Positively was scored only when 3 out of 3 of the triplicates have similar intensity. In the subtractive biopanning scheme plaques binding to normal serum proteins nonspecifically were removed by loading protein-G beads with a pool of control sera. One can detect positive reaction on filters spotted with phage epitope clones on filter 13 of 21 other patients using 153 reactive clones of the original 480 clones. Filters were tested with control sera not used in the initial subtractive step, and 5 of the 8 controls showed no reaction to the 480 phage on the filter arrays while a non-specific and even pattern of reactivity to all clones (without the typical triplicate pattern) was observed using 3 of the 8 different control sera (Table 1).

| Patient's sera | # of phage Patient #1 BP4 clones reacted with each patient's sera at indicated dilution | |
|---|---|---|
|  | 1:10000 | 1:3000 |
| PATIENT 1 | 153 (self reaction) |  |
| PATIENT 2 | None | 142 |
| PATIENT 16 | NS |  |
| PATIENT 20 | 70 |  |
| PATIENT 23 | 137 |  |
| PATIENT 29 | NS |  |
| PATIENT 30 | NS |  |
| PATIENT 33 | NS |  |
| PATIENT 35 | NS | 72 |
| PATIENT 37 | None | 120 |
| PATIENT 01-056 | NS |  |
| PATIENT 01-060 | None | 61 |
| PATIENT 00-007 | NS |  |
| PATIENT 01-108 | NS |  |
| PATIENT 01-045 | NS |  |
| PATIENT 42501 | 40 |  |
| PATIENT 400162 | 120 |  |
| PATIENT 40036 | Mostly NS |  |
| PATIENT 42780 | 85 |  |
| PATIENT B755 | NS |  |
| PATIENT 40015 | NS |  |
| PATIENT 075 | 119 |  |
| PATIENT 015 | 155 |  |
| PATIENT 035 | NS |  |
| PATIENT 007 | 114 |  |
| PATIENT 005 | 133 |  |
| PATIENT 083 | 150 |  |
| PATIENT 054 | 92 |  |
| PATIENT 064 | NS |  |
| PATIENT 065 | NS |  |

NS indicates Non-Specific reaction only:
None indicates No reaction detected.

The filter arrays were incubated with a patient's serum (pretreated with 150 µg of bacterial extract to block nonspecific reactions with *E. coli* proteins for 2 hours at 4° C.) at various dilutions for 1 hour at room temperature. Bacterial extracts are used because some patients have antibodies to bacterial protein, and therefore pre-treatment with extracts of *E. coli* proteins blocks the nonspecific antibodies to bacterial protein present in the patient's serum. The membranes were then washed three times with TBST (0.24% Tris, 0.8% NaCl, and 1% Tween-20®) for 15 minutes each. After washing was completed, the membranes were incubated with secondary antibody, goat-anti human IgG-HRP conjugated (Pierce) at 1:5000 dilution for 1 hour at room temperature. The membranes were again washed three times with TBST 15 minutes each. Finally, membranes are developed with Supersignal® (West Pico) chemiluminescent substrate (Pierce) and the images were captured on a Kodak® film.

Phagotope Microarrays on Glass Biochips Preparation of arrays Phage lysates are prepared as above. Phage lysates (usually five 96 well plates) from BP4 are transferred to 384-well plates, each lysate spotted in quadruplicate, using 10 µl per well. A robotic microarrayer is used to spot the phage in an ordered array onto FAST™ slides (Schleicher & Schuell) at a 350 µm spacing using 4 steel Micro-Spotting Pins. The arrays are dried overnight at room temperature.

Preparation of fluorescent antibody probes T7 monoclonal antibody and goat anti-human IgG are purchased from Novagen and Pierce respectively. Monofunctional NHS-ester activated Cy3 and Cy5 dyes are purchased from Amersham (PA33001 and PA35001). The antibodies are labeled in pH 8.0 sodium carbonate buffer as per the instructions from the manufacturer. Briefly, 100 µl of the protein solution with 5 µl of coupling buffer is transferred to the vial of reactive dye and mixed thoroughly. The reaction is incubated in the dark at room temperature for 30 minutes with additional mixing approximately every 10 minutes. The reaction solutions are then loaded into the gel filtration columns to separate the labeled protein from non-conjugated dye. T7 anti-body is labeled by Cy3 and anti human IgG is labeled by Cy5, respectively. The labeled protein is eluted and stored at 4° C. for future use. Reversing the dye-labeling scheme of the antibodies does not affect the results. The advantage of this strategy is that the same reagents were used on every phagotope array and the only variable is the patient's serum and therefore variations in labeling efficiency are not a factor.

Detection of fluorescent antibody probes The arrays are rinsed briefly in a 1% BSA/PBS to remove unbound phage, transferred immediately to 1% BSA/PBS as a blocking solution, and then incubated in this blocking solution for 1 hour at room temperature. The excess BSA is rinsed off from the slides using PBS. Without allowing the array to dry, 2 ml of PBS containing human serum at a dilution of 1:10,000 is applied to the surface in a screw-top slide hybridization tube. Multiple dilutions are tested per patient to obtain optimal detection. The arrays are incubated at room temperature for 1 hour with mixing. The arrays are rinsed in PBS to remove the serum, and then washed gently three times in PBS/0.1% Tween-20 solution 10 minutes each. All washes are performed at room temperature. After removing Tween-20 using PBS, the arrays are incubated with 2 ml of PBS containing Cy3-labeled-T7 anti-capsid antibody at a dilution of 1:50,000 and anti-human IgG labeled with Cy5 at a dilution of 1:10, 000 as probes for 1 hour in the dark. The incubation solution is mixed every 20 minutes. Three washes are performed using PBS/0.1% Tween-20 solution with 10 minutes each. The array is then rinsed with filtered ddH$_2$O twice and dried using a stream of compressed air.

Analysis Phagotope Microarrays The arrays are scanned in an Axon Laboratories scanner (Axon Laboratories, Palo Alto, Calif.) using 532 nm and 635 nm lasers. The ratio of anti-T7 capsid and anti-human IgG is determined by comparing the fluorescence intensities in the Cy3- and Cy5-specific channels at each spot. The location of each spot on the array is outlined using the image processing software. The background, calculated as the median of pixel intensities from the local area around each spot, is subtracted from the average pixel intensity within each spot. This normalized reactivity is entered into a database for analysis.

The information in this database can be analyzed in order to: i) select the most informative epitopes and ii) develop into a diagnostic test for tumor occurrence in high-risk women or tumor recurrence in women previously treated for ovarian cancer. The gene products thusly identified can provide insight into molecular changes recognized by the host immune system.

Figure 6C:
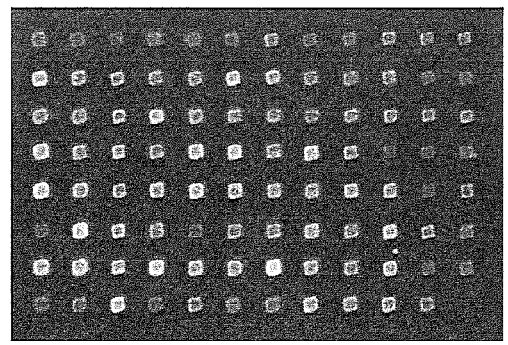
FIG. 6C is a scan of a microarray demonstrating the binding a Cy5-labeled antihuman IgG to human IgG from patient #1's serum and the control Cy3-labeled antibody to phage T7 capsid protein to phage clones microarrayed on glass.

The human antibodies reacting at each spot are detected with Cy5-labeled human serum antibodies. The normalization of the fluorescence at each spot is compared to a reaction with a Cy3-labeled antibody to the T7 phage capsid protein. Only a small fraction of the phage capsid protein is substituted with the in-frame fusion of the human cDNAs of the library. The majority of the capsid protein is produced by the host bacterium from an episomic T7-capsid gene. Therefore the majority of the each capsid protein is wild-type and can react with the anti-capsid antibody. An example of a Cy5 labeled anti-human IgG reacting with IgG in patients #1 serum bound to clones biopanned using patient #1 serum is shown in FIG. 6c.

The data analysis proceeds according to the following steps:

4. Pre-processing and normalization.
5. Identifying the most informative markers
6. Building a predictor for molecular diagnosis of ovarian cancer and validating the results.

The pre-processing and normalization step is used for arrays using two channels such as Cy5 for the human IgG and Cy3 for the T7 control. The spots are segmented and the mean intensity is calculated for each spot. A mean intensity value is calculated for the background, as well. A background corrected value is calculated by subtracting the background from the signal. If necessary, non-linear dye effects can be eliminated by performing an exponential normalization (Houts, 2000) and/or a piece-wise linear normalization of the data obtained in the first round. The exponential normalization can be done by calculating the log ratio of all spots (excluding control spots or spots flagged for bad quality) and fitting an exponential decay to the log(Cy3/Cy5) vs. log(Cy5) curve. The curve fitted is of the form:

$$y = a + b^* \exp(-cx)$$

where a, b and c are the parameters to be calculated during curve fitting. Once the curve is fitted, the values are normalized by subtracting the fitted log ratio from the observed log ratio.

This normalization has been shown to obtain good results for cDNA microarrays but it relies on the hypothesis that the dye effect can be described by an exponential curve. The piece-wise linear normalization can be done by dividing the range of measured expression values into small intervals, calculating a curve of average expression values for each such interval and correcting that curve using piece-wise linear functions.

The values coming from each channel are subsequently divided by the mean of the intensities over the whole array. Subsequently, the ratio between the IgG and the T7 channels was calculated. The values coming from replicate spots (spots printed in quadruplicates) are combined by calculating mean and standard deviation. Outliers (outside +/−two standard deviations) are flagged for manual inspection. Single channel arrays are pre-processed in a similar way but without taking the ratios. This preprocessing sequence was shown to provide good results for all preliminary data analyzed.

The step of selecting the most informative markers is used to identify the most informative phages out of the large set of phages started with. The better the selection, the better is the expected accuracy of the diagnosis tool.

A first test (Procedure 1 disclosed above) is necessary to determine whether a specific epitope is suitable for inclusion in the final set to be spotted.

Procedure 2 is used to maximize the information content of the set of epitopes while trying to minimize the number of epitopes used using the following procedure.

The arrays used in this example, (using two channels such as Cy5 for the human IgG and Cy3 for the T7 control) are processed as follows. The spots are segmented and the mean intensity is calculated for each spot. A mean intensity value is calculated for the background, as well. A background corrected value is calculated by subtracting the background from the signal. The values coming from each channel are normalized by dividing by their mean. Subsequently, the ratio between the IgG and the T7 channels are calculated and a logarithmic function is applied. The values coming from replicate spots (spots printed in quadruplicates) are combined by calculating mean and standard deviation. Outliers (outside +/−two standard deviations) are flagged for manual inspection.

The histogram of the average log ratio is calculated. If the histogram is unimodal (e.g subject 19218 in FIG. 13), there is no specific response. If the histogram is clearly bimodal (e.g. subject 19223 in FIG. 13), there is a specific response. All 25 subjects analyzed so far fell in one of these two categories or had no response at all. The preliminary data analyzed so far showed a very good separation of the distributions for the patients.

Once the chosen clones are spotted on the final version of the array, a number of sera coming from both patients and controls can be tested. These sera come from subjects not used in any of the phases that lead to the fabrication of the array (i.e. not involved in clone selection, not used as controls, etc.). Each test was evaluated using Procedure 3 above.

Building the Predictor

A number of machine learning and statistical techniques have been considered for this task. The following algorithms were tested: CN2 (Clark, 1989), C4.5 (Quinlan, 1993; Breiman et al., 1984), CLEF 1998), 4.5 using classification rules (Quinlan, 1993), incremental decision tree induction (ITI) (Utgoff, 1989; quantization (LVQ) (Kohonen, 1988; Kohonen, 1995), induction of oblique trees (OC1) (Health and Salzberg, 1993; Murthy, 1993), Nevada backpropagation (NEVP); Rumelhart et al., 1987), Constraint Based Decomposition (Draghici, 2001), k-nearest neighbors with k=5 (K5), Q* and RBF's (Musavi et al., 1992; Poggio and Girosi, 1990).

The generalization abilities and the reliability of these techniques have been tested extensively on various problems and data sets from the UCI machine learning repository (Blake et al., 1998). This repository contains a large collection of mostly real world data from a large variety of domains (including biological and medical), and constitutes a benchmark on which various algorithms and techniques can be tested.

Table 2 presents the accuracies obtained by these techniques on the selected problems. Table 3 presents the standard deviation of each such algorithm on the same problems. Based on these tests applicant decided to start the tests by using constraint based decomposition (CBD), radial basis functions (RBFs) and decision trees (C4.5) as the three main candidates. The CBD was selected because it offers a high reliability across multiple trials (lowest standard deviation) and a good accuracy (second best). Furthermore, the CBD algorithm can also produce a logical expression describing the classifier produced. Such expressions allow one to understand the relative importance of various epitopes. The decision trees have been selected mainly because they can be mapped into logical expressions that can be compared to the one produced by the CBD. RBFs construct clusters by placing high dimensionality Gaussian functions on groups of given data points (one data point can be a set of expression values corresponding to a protein chip). This technique calculates automatically the number of clusters, their orientation (the eigenvectors of the correlation matrix of the expression vectors) and their widths. RBFs were expected to perform much better than k-means clustering and the other techniques already used in this context because RBFs avoid guessing (e.g. k in k-means clustering). Furthermore, extracting a model from the trained RBF architecture is straightforward. Again, this model can be compared with the models provided by the CBD and C4.5

| DATASET | C4.5 | C4.5r | ITI | LMDT | CN2 | LVQ | OC1 | NEVP | K5 | Q* | RBF | CBD |
|---|---|---|---|---|---|---|---|---|---|---|---|---|
| GLASS | 70.23 | 67.96 | 67.49 | 60.59 | 70.23 | 60.69 | 57.72 | 44.08 | 69.09 | 74.78 | 69.54 | 68.37 |
| IONOSPHERE | 91.56 | 91.82 | 93.65 | 86.89 | 90.98 | 88.58 | 88.29 | 83.8 | 85.91 | 89.7 | 87.6 | 88.17 |
| LUNG CANCER | 40.17 | 39.84 | 38.47 | 55.49 | 37.17 | 55.71 | 54.28 | 33.12 | 68.54 | 60 | 65.7 | 60 |
| WINE | 91.09 | 91.9 | 91.09 | 95.4 | 91.09 | 68.9 | 87.31 | 95.41 | 69.49 | 74.35 | 67.87 | 94.44 |
| PIMA INDIANS | 71.02 | 71.55 | 73.16 | 73.51 | 72.19 | 71.28 | 50 | 68.52 | 71.37 | 68.5 | 70.57 | 68.72 |
| BUPA | 65.14 | 65.39 | 63 | 71.54 | 64.31 | 64.13 | 65.57 | 77.72 | 66.43 | 61.43 | 59.85 | 62.32 |
| TICTAC TOE | 83.52 | 99.17 | 92.89 | 89.61 | 98.18 | 65.61 | 78.56 | 96.91 | 84.32 | 65.7 | 72.19 | 75.1 |
| BALANCE | 64.61 | 75.01 | 76.76 | 93.27 | 80.89 | 89.54 | 92.5 | 91.04 | 83.96 | 69.21 | 89.06 | 90.08 |
| IRIS | 91.6 | 91.58 | 91.25 | 95.45 | 91.92 | 92.55 | 93.89 | 90.34 | 91.94 | 92.1 | 85.64 | 96 |
| ZOO | 90.27 | 90 | 90.93 | 96.61 | 91.91 | 91.42 | 66.68 | 92.86 | 67.64 | 74.94 | X | 94.29 |
| AVG | 75.92 | 78.42 | 77.87 | 81.84 | 78.89 | 74.84 | 73.48 | 77.38 | 75.87 | 73.07 | 74.22 | 79.75 |

Table 2 shows a comparison of several classification techniques. The table presents the accuracies obtained in various problems from the UCI machine learning respiratory. Each accuracy is the average of 10 trials.

| DATASET | C4.5 | C4.5r | ITI | LMDT | CN2 | LVQ | OC1 | NEVP | K5 | Q* | RBF | CBD |
|---|---|---|---|---|---|---|---|---|---|---|---|---|
| GLASS | 7.23 | 6.28 | 7.96 | 11.25 | 8.34 | 10.24 | 9.1 | 6.29 | 7.81 | 6.98 | 7.35 | 2.08 |
| IONOSPHERE | 2.82 | 2.58 | 2.71 | 3.51 | 3.29 | 3.36 | 2.21 | 3.81 | 4.14 | 4.7 | 6.45 | 2.56 |
| LUNG CANCER | 14.2 | 18.92 | 13.52 | 32.2 | 13.79 | 12.48 | 17.53 | 14.83 | 11.96 | 18.6 | 16.27 | 12.6 |
| WINE | 5.84 | 5.09 | 6.24 | 5.22 | 6.11 | 4.84 | 8.45 | 2.22 | 6.86 | 6.64 | 5.16 | 1.96 |
| PIMA INDIANS | 2.1 | 3.92 | 2.16 | 4.3 | 2.36 | 4.46 | 22.4 | 3.19 | 3.67 | 8.19 | 2.39 | 3.02 |
| BUPA | 5.74 | 6.05 | 4.23 | 6.63 | 7.99 | 7.14 | 8.45 | 11.97 | 7.22 | 4.25 | 7.92 | 2.05 |
| TICTAC TOE | 2.44 | 1.05 | 2.38 | 8.79 | 0.95 | 2.99 | 5.88 | 1.32 | 2.7 | 3.16 | 3.35 | 9.43 |
| BALANCE | 3.35 | 3.98 | 3 | 2.95 | 3.38 | 4.39 | 2.07 | 7.12 | 7.53 | 19.09 | 2.38 | 3.03 |
| IRIS | 5.09 | 5.09 | 4.81 | 4.71 | 5.95 | 3.73 | 4.68 | 7.45 | 4.1 | 5.28 | 27.37 | 4.35 |
| ZOO | 7.59 | 7.24 | 6.11 | 1.56 | 5.95 | 6.26 | 30.36 | 4.62 | 20.03 | 23.8 | X | 2.13 |
| AVG | 5.64 | 6.02 | 5.312 | 8.112 | 5.811 | 5.989 | 11.11 | 6.282 | 7.602 | 10.07 | 8.738 | 4.321 |

Table 3 shows a comparison of several classification techniques. The table presents the standard deviations obtained in a set of 10 trials on various problems from UCI machine learning repository.

Furthermore, one can also implement and try the predictors used in (Golub et al., 1999) and (Alizadeh et al., 2000) which were shown to work well in cancer diagnosis problems similar to applicants. The selection of the final predictor was based on the validation results obtained in the last step of the data analysis.

Validating the Predictor

In order to validate the predictors, the classical method of cross-validation was used (Breiman et al., 1984). The idea behind cross-validation is that the predictor is tested, not based on its abilities to simply memorize the data presented during the training, but based on its abilities to generalize the knowledge acquired during the training to previously unseen cases. For this reason, the predictor must be checked on data that belongs to the same distribution but was not used during the training. This can be implemented in several ways depending on the number of examples available. If only few examples (such as stage I patients, ~40 total) are available, reducing the size of the training set even further by setting patterns aside for generalization testing could jeopardize the training. In such cases, the algorithm is used with only n−1 of the n available patterns and tested on the remaining one. This is done n times, each time leaving out a different pattern. An average is calculated over the n experiments. This is known as the leave-one-out method. If more patterns are available, the pattern set can be divided into n different subsets of patterns. Then one subset can be left out of the training and used to test the generalization. Again, the value reported is an average of the n trials performed leaving out each of the n subsets. This method is known as n-fold cross validation. Finally, if the pattern set is very large (patients with stage III or IV cancer), it can simply be divided into a training set and a validation set. In this case, the generalization abilities of the technique can be characterized by its performance on the validation set.

For each predictor the specificity, sensitivity, positive predictive value and negative predicted value can be calculated using cross-validation data (i.e. values that have not been used in constructing the predictor itself. This ensures that the quality measures obtained in this study reflect the real world performance to be expected in the field.

Once informative phagotopes are found the gene encoding the phagotope was identified.

1. Identification genes encoding the phagotopes. Phage clones specifically reacting with patient sera, as determined by microarray immunoscreening, can be amplified by PCR using T7 capsid forward and reverse primers. PCR fragments were purified and 100 ng of fragment was analyzed to determine the nucleotide sequence of the cDNA insets. Sequence alignments are performed using BLAST software and GenBank databases. The sequence information can be used in several ways. Initially, the DNA sequence information provides a database of the frequency of reactivity to a particular epitope.

Diagnostic Markers Derived from the Combined Processes Including Biopanning, Assay of Patients' Sera with Epitopes on Filters and Biochips, and Identifying the Best Predictor/Marker of Disease.

DNA Sequence Analysis of Phagotope Clones

PCR amplified DNA sequences from 96 phagotopes that reacted with patient #1 and at least one other OVCA serum are shown in the table below. Some clones were isolated multiple times and one clone was represented 23 times out of the 96 clones analyzed. This was the human homologue of the oncogenic gene Bmi-1, (GenBank NM005180.1) that inhibits the expression of p14ARF and cooperates with c-myc (Lindstrom et al., 2001. The insert sizes for the Bmi-1 phage clones varied in coding capacity depending on the isolate between 67-94 amino acids in length. Eight other clones were represented twice and one was isolated three times. One of these genes isolated twice was the heat shock protein 70, which has been shown to be overexpressed and antigenic in ovarian cancer tumors and was found to have been identified in the SEREX database 5 times. The size of the open reading frame in the HSP70 clone is 109 amino acids in length. Another clone isolated two times of the 96 sequenced is a known cancer antigen called RCAS1 which is overexpressed in 58% of ovarian cancer and many others as well (Sonoda et al., 1996) RCAS1 is an estrogen regulated gene which can inhibit the immune system from killing a tumor (Nakashima et al., 1999). This information clearly indicates that this technology is capable of detecting cancer antigens that can be used for diagnostic and immunotherapy purposes. If overbiopanning occurred, only a few different clones would be found. However, as the remaining clones were isolated once each, it is therefore convincing that 4-5 biopannings is appropriate. In this first group of 480 clones there were isolated clones that reacted with approximately 60% of the OVCA patients using the macroarray filters and more efficiently using the microarray technology. Additional epitope clones provide additional sensitivity for this assay.

| Clone Name | GenBank ID |
| --- | --- |
| Clone found 23 times Bmi-1 (oncogene) | NM_005180.1 |
| Clones found 2-3 times | |
| RCAS1 (EBAG9) | BC005249.1 |
| A-kinase anchoring protein 220 | XM_038666.1 |
| G-protein gamma-12 subunit | NM_018841.1 |
| Neuronal apoptosis inhibitory protein 6 | AF242431.1 |
| hypothetical protein DC42 | XM_028240.1 |
| WD repeat domain 1 (WDR1) | XM_034454.1 |
| zinc finger protein 313 | XM_009507.1 |
| 54 other clones isolated once each. | |

Serum reactivity toward a cellular protein can occur for two possible reasons: 1) expression of a mutated form of the protein by the tumor cells and 2) overexpression of the protein in the tumor cells. Identification of proteins detected by the host immune system in this fashion therefore provides patienthanistic information about protein(s) that can be mutated or overexpressed in ovarian cancer. Such information provides insight into the molecular targets and mechanisms giving rise to ovarian cancer. Lastly, the sequences identified using the epitope-biopanning/phage microarray approach can be useful for early detection of cancer occurrence and recurrence by screening patients' sera and peritoneal fluids and providing immunogens for immunotherapy vaccines.

Example 2

A strategy was developed for serological detection of large numbers of antigens indicative of the presence of cancer, thereby using the humoral immune system as a biosensor. The high-throughput selection strategy involved biopanning of an ovarian cancer phage display library using serum immunoglobulins from an ovarian cancer patient as bait. Protein macroarrays containing 480 of these selected antigen clones revealed 44 clones that interacted with immunoglobulins in sera from all (32/32) ovarian cancer patients, but not with sera from either healthy women (0/25) or patients having other benign or malignant gynecological diseases (0/14). An informative subset of 26 antigen clones was chosen based on the criterion that the serum from each of a group of 16 patients interacted with at least one of the clones. When another, independent group of 16 serum samples was used, all 16 samples interacted with one or more of the 26 clones, and none from 12 healthy women. The process of globally profiling disease relevant epitopes is known as "epitomics".

In searching for a method for the early detection of ovarian cancer (OVCA), large numbers of potential diagnostic antibodies were identified and a high-throughput strategy was developed to clone antigen biomarkers. Because antibodies to any single antigen tend to detect only a small fraction of cancer patients, the necessity to screen a large panel of potential antigen markers was recognized. Therefore a differential biopanning technique was used to screen T7 phage display cDNA libraries to isolate cDNAs coding for epitopes binding with antibodies present specifically in the sera of patients with early or late stage ovarian cancer but not with antibodies in the sera of healthy women. Using a single OVCA patient's immunoglobulins (IgG) as bait, there were identified both established and novel antigen biomarkers. Large numbers of cancer-associated antigens can be found by this phage display technique more rapidly than using standard SEREX analysis. This is due to the power of repeated cycles of selective enrichment possible with viable phage display cDNA biopanning, especially when screening is performed with serum containing a complex mixture of low titer of IgGs, compared to the single step screening possible with SEREX, which is biased toward the identification of antigens that can be detected at a relatively high titer of IgGs.

The antigens that were identified through this process have diagnostic value with additional potential for development of therapeutic vaccines or imaging reagents. Since the host immune system can unravel molecular events (overexpression or mutation) critical to the genesis of ovarian cancer, this novel proteomics technology can identify genes with significant mechanistic involvement in the etiology of the disease. Our initial goal is to develop a serum-based test that can detect ovarian epithelial cancer at an early and curable stage.

Methods

Serum Samples. Blood samples from ovarian cancer patients (Stages I-IV) and healthy controls were obtained from the Barbara Ann Karmanos Cancer Institute. Processing of blood to extract serum was performed in the laboratory. Briefly, blood samples were centrifuged at 2500 rpm at 4° C. for 10-15 minutes and supernatant were stored at −70° C. until use.

Construction of T7 phage display cDNA library from ovarian cancer cell line, SKOV3. Isolation of mRNA from total RNA. Ovarian cancer cells were grown in monolayer culture.

Total RNA was prepared using trizol reagent according to manufacturer's instructions (Invitrogen, Carlsbad, Calif., USA). Total RNA, 0.5 mg, was used for the purification of Poly(A)+ mRNA following the method as suggested by the manufacturer (QIAGEN Inc, Valencia, Calif.). Poly(A)+ mRNA was quantitated by UV spectroscopy and the process of poly A selection was repeated once. Twice poly (A) selected mRNA was stored at −70° C. for use in library preparation.

Construction of T7 phage display cDNA library. Novagen's OrientExpress® cDNA Synthesis and Cloning systems were used in the construction of the ovarian cancer T7 phage cDNA libraries (Novagen, cDNA manual, TB247). The OrientExpress Random Primer System was used to achieve orientation-specific cloning between EcoRI and HindIII sites. First and second strand cDNA synthesis were sequentially carried out in the presence of 5-methyl dCTP. After second strand synthesis, the cDNA was treated with T4 DNA polymerase to blunt the ends. The addition of EcoRI/HindIII Directional Linker d(GCAAGMTTCAAGC) (SEQ ID NO: 3) at the d(A)n:d(T)n end created a HindIII site d(AAGCTT) (SEQ ID NO: 4) in which the two underlined bases were derived from cDNA. The two dT's were provided on the 5' end of each first strand by the HindIII random primer d(TTNNNNNN) (SEQ ID NO: 5). Excess linkers and small cDNAs (<300 bp) were removed by a gel filtration step as described in Novagen's manual TB 247. The digestion of the cDNA with both HindIII and EcoRI thus yielded cDNA molecules ready for directional insertion into EcoRI/HindIII vector T7Select 10-3 arms. After vector ligation and packaging using T7 packaging extracts, the phage were plated to determine the library titer. About 50 phage clones were randomly picked up and PCR was performed with the T7 forward primer (TCTTCGCCCAGAAGCAG) (SEQ ID NO: 6) and T7 reverse primer (CCTCCITTCAGCAAAAACCCC) (SEQ ID NO: 7), in order to determine the insert sizes. The insert size range was found to be between 300 bp-1.5 kb.

Amplification of packaged libraries by liquid culture method. 10 ml of LB/carbenicillin medium was inoculated with a single colony of *E. coli* strain BLT5615 from a freshly streaked plate. The mixture was shaken at 37° C. overnight. Five ml of the overnight culture was added to 90 ml of LB/carbenicillin medium and was allowed to grow until the $OD_{600}$ reached 0.4-0.5. After obtaining the appropriate OD, 1 mM Isopropyl-β-D-thiogalacto-pyranoside (IPTG), (1×) M-9 Minimal salts and 0.4% glucose were added and the cells were allowed to grow for 20 minutes. An appropriate volume of culture was infected with phage library at multiplicity of infection (MOI) of 0.001-0.01 (100-1000 cells for each pfu). The infected bacterial culture was incubated with shaking at 37° C. for 1-2 hours until lysis was observed. After lysis, 0.02% glycerol and 0.02M phenyl-methyl sulphonyl fluoride (PMSF) and protease inhibitor cocktail (PIC) were added to the cell lysate to block proteolysis of the capsid fusion proteins. The phage lysate was centrifuged at 8000×g for 10 minutes. The supernatant was collected and stored at 4° C. The lysate was titered by plaque assay under standard conditions. The libraries were stored at −80° C. after purification by polyethylene-glycol precipitation and ultracentrifugation through a cesium chloride step gradient.

Selection of T7 Phage Displayed cDNA Libraries with Human Sera.

Affinity selection with sera from normal individuals. Twenty-five µl of Protein G Plus-agarose beads were placed into a 0.6 ml microcentrifuge tube and washed twice with 1× phosphate buffered saline (PBS). The washed beads were blocked with 1% bovine serum albumin (BSA) at 4° C. for 1 hour and then incubated at 4° C. for 1 hour with 250 µl of pooled sera from 20 healthy women at a 1:20 dilution. After 3 hours of incubation, beads were washed three times with 1×PBS and then incubated with phage library (~$10^{10}$ phage particles) made from an ovarian cancer cell line, SKOV3. The mixture was centrifuged at 3000 rpm for 2 minutes to remove phage nonspecifically bound to the beads and the supernatant (phage library) was collected for immunoselection.

Immunoselection of the phage mixture with serum from an ovarian cancer patient. Protein G Plus agarose beads were placed into a 0.6 ml microcentrifuge tube and washed two times with 1×PBS. The washed beads were blocked with 1% BSA at 4° C. for 1 hour and then incubated at 4° C. with 250 µl of a 1:20 dilution of serum from the ovarian cancer patient, MEC1. After 3 hours, the beads were washed three times with 1×PBS and incubated for immunoselection overnight at 4° C. with the phage library supernatant. After this incubation, the mixture was centrifuged at 3000 rpm for 2 minutes and the supernatant was discarded. The beads were washed three times with 1×PBS and the phage was eluted from the washed beads as per the manufacturers instructions. The bound phage was removed from the beads by centrifugation at 8000 rpm for 8 minutes. Eluted phage (200 µl) were transferred to liquid culture for amplification (100 µl elution to 20 ml culture). Four rounds of affinity selection were carried out on the amplified phage obtained for each series of biopannings. The number of biopanning cycles generally determines the extent of the enrichment for phage that binds to the sera of patient with ovarian cancer. Four other serum samples from ovarian cancer patients were also used for immunoselection of clones. MEC1 gave the strongest binding with its clones and therefore those clones were selected for the remainder of this study.

Figure 12A:
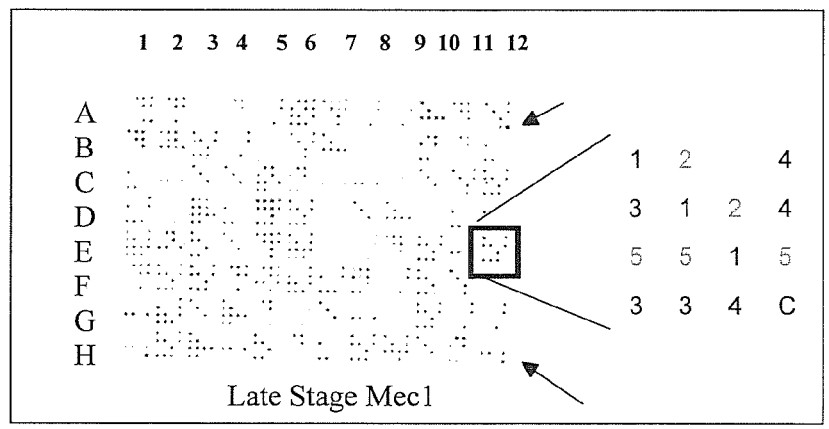
FIGS. 12A-G are filter microarrays showing antigen binding with IgGs in the serum of Stage I ovarian cancer patients.
Figure 12B:
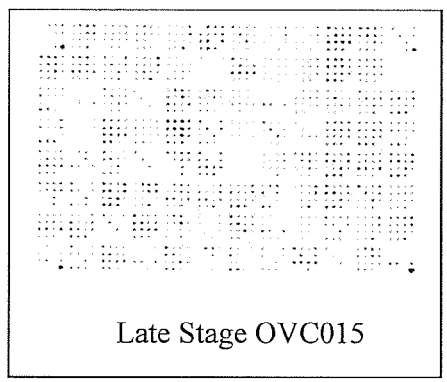
Figure 12C:
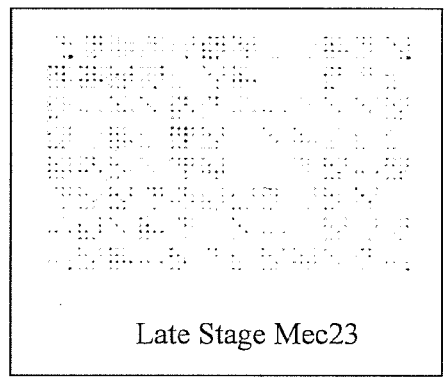
Figure 12D:
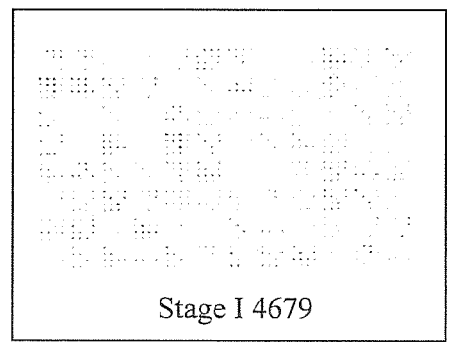
Figure 12E:
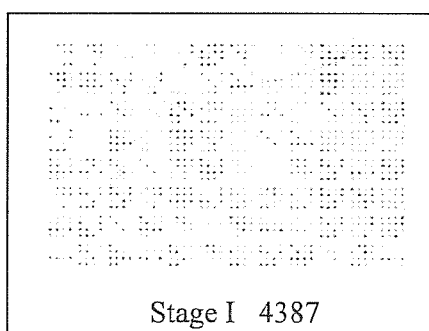
Figure 12F:
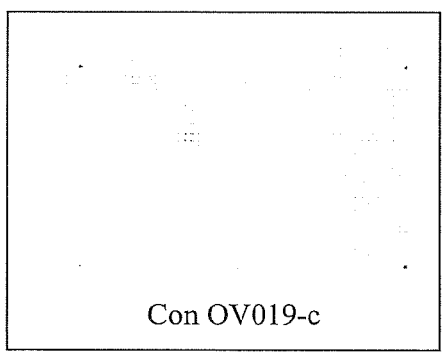
Figure 12G:
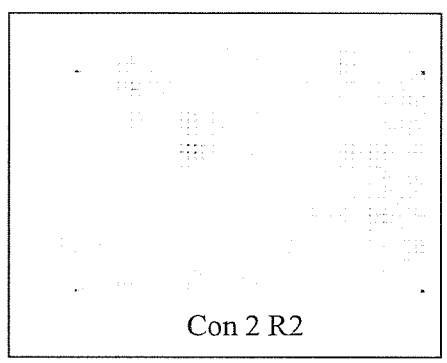
Figure 13A:
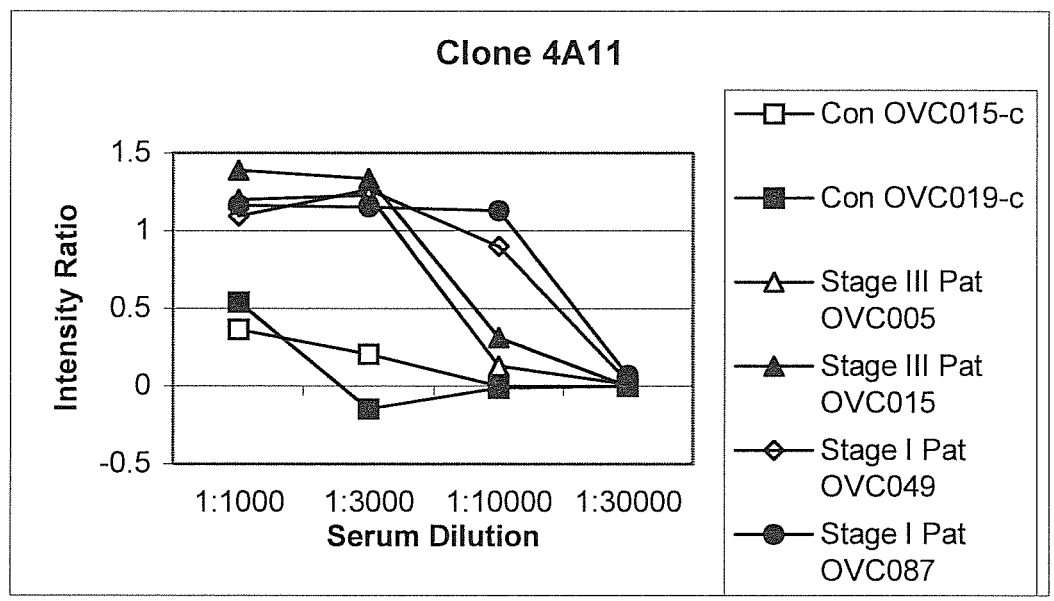
FIGS. 13A-D are graphs showing the determination of a titerable antigen-antibody binding in ELISA macroarray analysis.
Figure 13B:
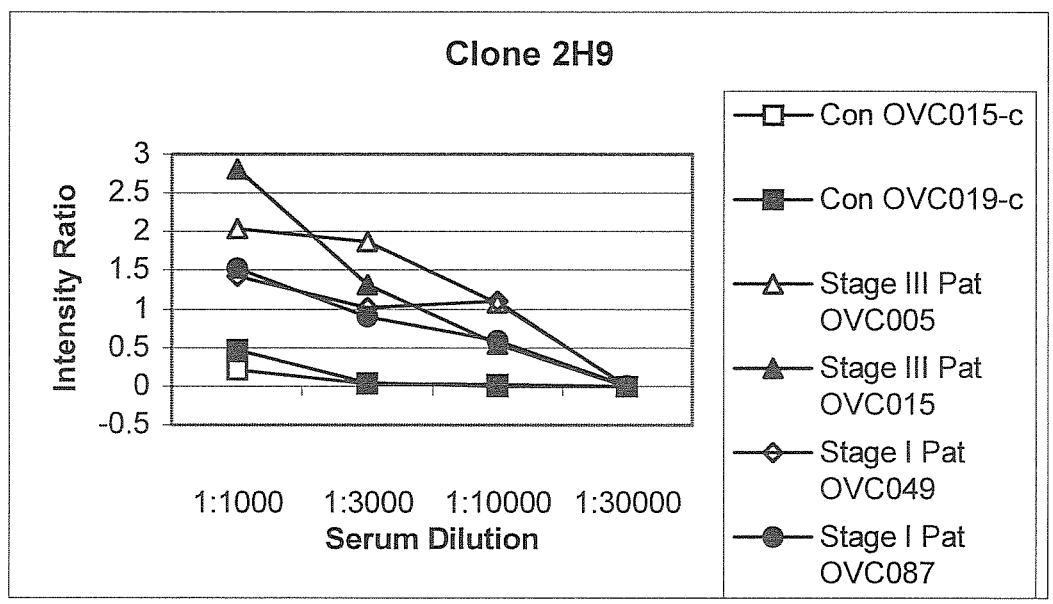
Figure 13C:
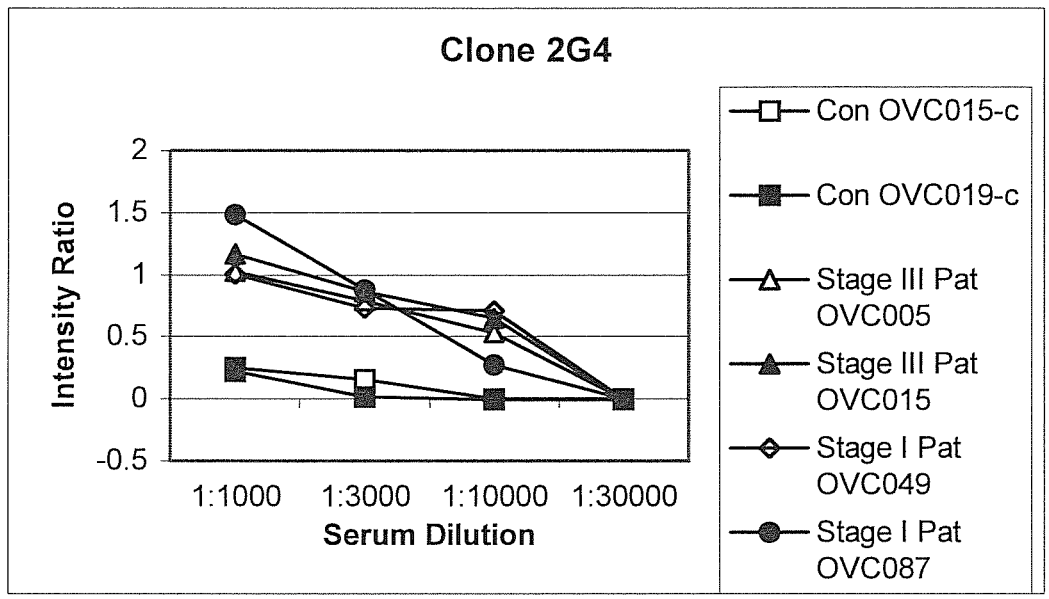
Figure 13D:
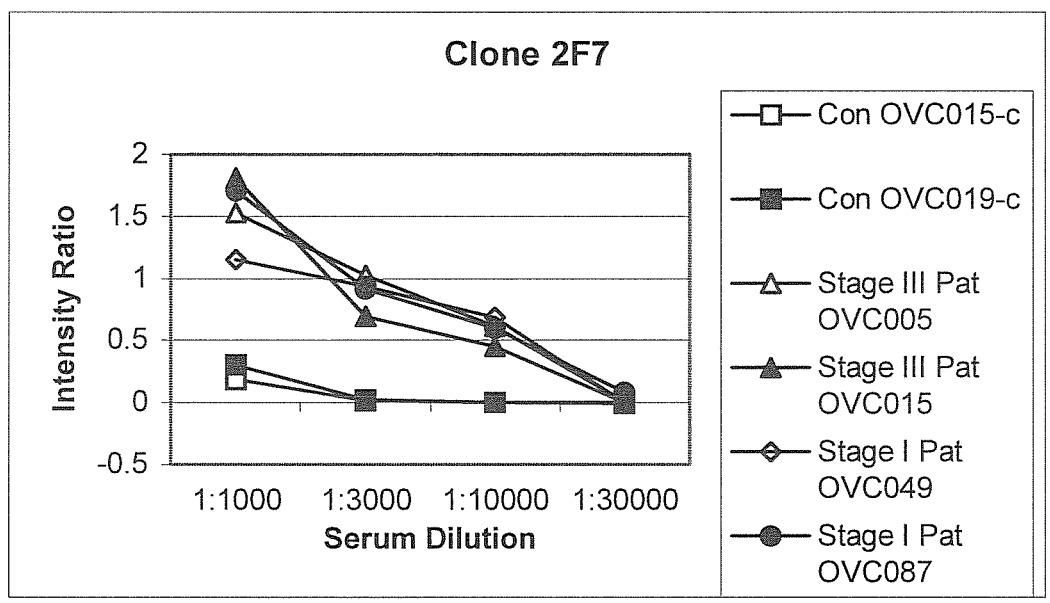

Macroarray immunoscreening. The titer of the T7 phage library obtained after amplification of each Biopanning (BP1-BP4) eluate was determined by plaque assay. *E. coli* BLT5615 was infected with the primary unamplified phage from biopanning (BP1-BP4) and plagued to limiting dilution onto LB/carbenicillin plates (150 mm×15 mm petri dish) so that sufficient numbers of single plaques could be isolated to obtain 12×96 well plates for arraying. The plates were incubated at 37° C. for 3-4 hours until the plaques were visible and then picked for amplification in the 96-well plates. Lysis of the host bacteria generally occurred after 2 hours. After bacterial lysis, the plates were centrifuged at 3000 rpm for 20 minutes. The samples from the 96-well plates were arrayed onto a nitrocellulose membrane (Osmonics) using the Beckman Biomek 2000 liquid handling robot. This robot, equipped with a 96-pin printing head spotted the samples contained in 96 well plates onto nitrocellulose membranes. The patterns were printed in a 4×4 configuration. Position A1 contained 16 spots, each representing a phage sample (FIG. 12A). Triplicates were printed from well A1 of each of five different 96 well plates (15 spots) and the $16^{th}$ spot contained a positive control of diluted human serum used in the 4 corners of the plate only as shown by black arrows (FIG. 12A). After each round of spotting, the pins were washed in 0.1% SDS, sterile water, and then ethanol. After the spotting was completed, nitrocellulose membranes were blocked with 5% non-fat dry milk for 1 hour at room temperature. The membranes were then incubated with a patient's serum (pre-treated with 150 µg of bacterial extracts for 2 hours at 4° C.) at a dilution of 1:10000 or 1:3000 for 1 hour at room temperature. Bacterial extract was used because some patients and controls had antibody binding to bacterial protein(s). The membranes were then washed three times with 0.24% Tris, 0.8% NaCl, 1% Tween-20(TBST) for 15 minutes each and then incubated with secondary antibody, goat-anti human IgG-HRP conjugated (Pierce, Rockford, II, USA) at 1:5000 dilution for 1 hour at room temperature. The membranes were again washed three times with TBST for 15 minutes each, developed with Supersignal® (West Pico) chemiluminescent substrate (Pierce, Rockford, II, USA) and the images captured on X-ray film.

Stability of Serum Specimens. One source of error in the immunodetection on macroarrays could be variability in serum sample preparations or storage. Therefore, a test was performed to determine whether some common handling conditions adversely affect the usefulness of the sera for the assays. For this test, several aliquots of the same serum sample from one ovarian cancer patient were subjected to various treatments; repeated freeze-thaw cycles (10 times), incubation of the blood sample at 37° C. for 72 hours before processing the serum, extended storage at 4° C., treatment at room temperature overnight, and heat treatment at 65° C. for 10 minutes. Freshly thawed serum, processed normally, served as a control. Robotically printed nitrocellulose membranes containing the set of 480 clones were later processed with each of those treated and untreated serum samples.

ELISA Macroarray analysis. Forty-four Stage I-IV clones, in triplicate, were arrayed onto a nitrocellulose membrane (Osmonics) using the Beckman Biomek 2000 liquid handling robot. Nitrocellulose membranes were blocked with 5% non-fat dry milk for 1 hour at room temperature and then incubated with patient or control serum (pretreated with 150 µg of bacterial extract for 2 hours at 4° C.) at dilutions of 1:1000, 1:3000, 1:10000 and 1:30000 for 1 hour at room temperature. Immunoreactivity was performed with serum from patients or healthy controls. For one set, the immunoreactivity was also performed with a monoclonal antibody to the N-terminus of the T7 gene 10 protein at dilution 1:10000. This was performed as described in the macroarray immunoscreening. The intensity of each spot was measured using ImaGene software from BioDiscovery Inc, with background subtraction and calculated using the following equation:

Intensity Ratio=(Mean of Clone)/(Mean of T7 for 12 replicates of that Clone)−(Mean of Blank Phage)/(Mean of T7 for 12 replicates of that Blank Phage).

The Intensity Ratio vs Serum concentration was plotted for each antigen clone.

Sequencing of phage cDNA clones. Individual phage clones were PCR amplified using forward PCR primer 5' GTTCTATCCGCAACGTTATGG 3' (SEQ ID NO: 8) and reverse PCR primer 5' GGAGGAAAGTCGTTTTTTGGGG 3' (SEQ ID NO: 9). PCR products were purified on 1% agarose gels. The bands were excised from gels under UV light and DNA was extracted/purified using a Qiagen gel extraction kit (Qiagen Inc, Valencia, Calif., USA). Fifty ng of each purified PCR product was analyzed using forward Sequencing primer 5' TGCTAAGGACAACGTTATCG 3' (SEQ ID NO: 10) by Wayne State University DNA Sequencing Core Facility.

Results

Differential Biopanning of T7 Phage cDNA Expression Libraries Employing Sera Obtained from Women with Ovarian Cancer and Healthy Controls A method of differential biopanning to screen a T7 phage cDNA library prepared from an ovarian cancer cell line, SKOV3, was developed using a late stage ovarian cancer patient's serum (MEC1) as the bait to isolate tumor-specific antigens. First the library was pre-adsorbed with sera pooled from 20 healthy controls so as to remove the antigen clones binding with common antibodies unrelated to cancer. The resulting phage were then bound to antibodies present in the serum of a cancer patient and the unbound phage removed. This selection procedure was repeated four times, amplifying the phage between cycles of biopanning. Groups of 96 clones were picked from the patient's biopanning at cycles 1, 2, 3 and 4. Amplified phage clones were spotted on nitrocellulose membranes, and useful phage clones were identified by their binding with patient IgG antibodies at a dilution of 1:10000. There was a significant enrichment for phage-bearing epitopes that bound serum IgGs after the fourth round of biopanning. Because about 35% of the selected phage clones interacted with MEC1 serum IgGs after the fourth round of biopanning, further biopanning was not performed to avoid reducing the diversity of phage clones.

Serological Detection of Antigens Using Macroarrays

The utility of such phage display antigen clone sets for the serological detection of cancer is best demonstrated by their interaction with sera from patients other than those used in the selection step. A set of 480 clones from the fourth round of biopanning was robotically spotted on nitrocellulose membranes. The binding of the cloned antigens with the IgGs in patients' sera was analyzed at a dilution of 1:10000. The strong positive interactions observed with the MEC1 serum indicated a relatively high titer of the IgG molecules that bound with the MEC1 clones (FIG. 12A). Several dilutions of the MEC1 serum were previously used for antigen detection and a dilution of 1:10000 produced the cleanest pattern of strong binding. Although 480 clones were identified from the biopanning with MEC1 serum as the bait, not all 480 clones interacted with the MEC1 serum (FIG. 12A). This can be explained by a non-specific interaction between phage clones and the Protein-G+ beads bearing the serum antibodies. When serum IgG-binding with sera from other patients (non-self reaction) was analyzed using replicates of these robotically spotted macroarrays, cross-reactivity was observed in most patients at a dilution of 1:10000 (FIG. 12B-E). Sera from other patients required either a 1:3000 or 1:30000 dilution to detect positive clones. Binding was scored positive only when 3 of the triplicates had similar intensity and when the intensity was significantly higher than the background intensity of other spots within the same patch. Sera from 71 individuals were tested; 10 were from women with early stage OVCA (Stage I and Stage I borderline), 22 from women with late stage OVCA, 14 from women with benign or other gynecological diseases, and 25 from healthy controls. Tumor histology and stage of all the patients' used for the study are listed in Table 4. Late stage patients OVC015 and MEC23 bound more intensely than the Stage I patients 4679 and 4387 (FIG. 12B-E). In the subtractive biopanning scheme, phage epitope clones binding IgGs were isolated in control sera even though these control sera were not used in the initial subtractive biopanning steps. As expected, a fraction of the 480 phage clones on the macroarrays interacted with approximately 10% of the controls. All clones that interacted with the control sera were eliminated from further consideration. One hundred and forty-nine clones interacted with sera from Stage I-IV ovarian cancer patients but with none of the 25 control sera. Forty-four out of 149 clones interacted specifically with these Stage I-IV sera. The remaining 105 clones interacted with sera from women who had benign tumors, endometrial cancers or other gynecological diseases and may represent biomarkers of gynecological sickness. These clones were excluded because these conditions are a common source of false positive results in CA-125 clinical testing. A matrix summarizing the binding of the 44 Stage I-IV selected antigen clones to sera from patients and controls is shown in Table 5A. The derivation of this matrix was based on an agreement between two observers who analyzed the data independently, with 87% concordance.

Only 2/44 selected clones, 2G4 and 3B12, bound with MEC1 serum IgGs despite the fact that T7 cDNA library was biopanned with MEC1 serum as the bait. A large number of clones interacting with the MEC1 serum were eliminated because they bound with either healthy control or with patients having benign or other gynecological diseases. The best markers are those interacting with the most patients; these include such clones as 2H9 (13/32), 2G2 (13/32), 2B4

(12/32), and 2G4 (12/32) that had the highest frequency of IgG binding with sera from ovarian cancer patients. Three antigens, 2F7/2B4, 5C3/2G4, 2E1/4A3 were found in multiple clones resulting in a panel of 41 markers binding with IgGs in Stage I-IV ovarian cancer sera (Table 5A).

Although 41 antigens interacted with sera from all 32 patients, the number of clones in the set needed to detect all 32 ovarian cancer patients were reduced. The serum set from 32 patients was randomly divided into two groups. The first group (Group 1) consisted of 16 patients and 25 healthy women; and the second group (Group 2) consisted of the other 16 patients and 12 different healthy women. Group 1 was used to select the minimum number of clones necessary to detect all patients. The strategy of clone selection involved ranking of clones in order of decreasing binding with sera from ovarian cancer patients (Table 7A). Next, a combination of clones was selected for binding with IgGs in sera from all of the ovarian cancer patients in the set. Twenty-six clones of Group 1 detected all of the ovarian cancer patients (16/16) (Table 7A); all but one patient's serum bound with more than one of the selected clones. These 26 clones were then tested on sera from Group 2 (16 patients and 12 healthy controls), for antibody binding (Table 7B). Sera from all of the patients in Group 2, (16/16), bound with at least one of these clones and none of the sera from the healthy women (0/12) bound to these clones.

A second group of 21 clones was found to interact with (18/22) late Stage patients' sera but not with sera from early stage patients, with sera from 25 healthy women or with sera from 14 patients with either benign tumors, endometrial cancers or other gynecological diseases (Table 5B). Although 4 late stage patients were not detected by these 21 clones (Table 5B), they were detected by 44 Stage I-IV clones (Table 5A). Among these 21 clones, antigen 2B3 interacted with the greatest number of patients sera (10/22), clone 5A2 with 8/22, clones 2D7 and 2E7 with 5/22 sera. Although these clones did not detect women with early stage ovarian cancer, further analysis may show them to be useful as markers of recurrence.

Stability of Serum Specimen.

An important feature of a test for widespread clinical use is the stability of the analyte in the test sample. To identify any inaccuracy in detecting IgG molecules in this multianalyte assay due to serum sample preparation problems or serum storage, a test of the durability of the serum samples was carried out. Repeated freeze-thaw cycles (10 times), heated to 65° C. for 10 minutes, or left the unprocessed blood at 37° C. for 72 hours were performed. Only heat treatments of the serum affected the positive signals on the macroarrays, because heat treatment is sufficient to denature immunoglobulins (IgG). Therefore, the complex set of IgG molecules in serum samples are very stable and provide a reliable analyte for clinical studies of diagnostic arrays of cloned antigens.

ELISA Macroarray Analysis.

The set of 44 (Stage I-IV) phage display cDNA clones listed in Table 5A, were printed robotically on nitrocellulose membrane and an enzyme-linked immunosorbent assay (ELISA)-like experiment was performed. For clones 4A11, 2H9, 2G4 and 2F7, the binding of antigens decreased with increasing dilution of serum (FIG. 13A-D). Although clones bound nonspecifically with control sera at high serum concentrations, their binding decreased to zero as the sera were diluted, whereas the interaction of the same clones with IgGs in patients' sera persisted at even 1:10000 serum dilution. This demonstrated that the interaction of antigen clones with patients' sera was indicative of a typical, titerable antigen-antibody interaction.

Phage-Coded Antigen Sequence Analysis

To identify the selected gene products, phage DNAs were amplified by PCR and the cDNA products sequenced. The DNA sequences were checked for homology to the GenBank databases using BLAST. The predicted amino acids in-frame with the T7 gene 10 capsid protein were determined. Eleven sequences were homologous to known gene products while other clones had no homology to any annotated sequences in the public databases (Table 6A). Among the gene products, 11 represented known gene products in the correct orientation and in the correct reading frame with the T7 gene 10 capsid protein indicating that the serum IgG binding region was localized to a portion of the natural open reading frame of the protein. Of the remaining 33 clones, 13 clones contained an open reading frame with the T7 10B gene with a frameshift within the natural reading frame of the gene; 7 clones contained portions of either 5' or 3' untranslated regions of known genes; 13 clones contained segments of genomic sequences. This in turn resulted in the formation of recombinant fusion proteins in which the predicted amino acid of the in-frame fusion with the T7 10B protein was not similar to the original protein coded by the gene. The size of the additional peptide sequences ranged from 5-48 amino acids. This result indicated that the recombinant gene products of these clones must be coding for proteins that mimic some other natural antigens, and hence can be termed mimotopes (Table 6A). BLASTp search of the SWISSPROT database for homology to each in-frame mimotope confirmed this observation. For example, clone 2H5 contained a nucleotide sequence homologous to the ATP synthase, H+ transporter. Using BLASTp, there was observed a sequence homology of (8/10) amino acids with the leukocyte common antigen precursor. Each mimotope had significant homology to a natural open reading frame (Table 6A).

Discussion

The early detection of cancer is a significant challenge in clinical oncology. Once accurate methods become available, early detection can result in a significant reduction in morbidity and mortality of these diseases. The detection of ovarian cancer at Stage I could result in a cure rate of 90%. To this end there has been devised an approach of high-throughput selection of antigen biomarkers using phage display libraries and marker selection using a highly parallel analysis on macroarrays. The process began with a representative sample of 480 cloned markers from biopanning an ovarian cancer T7 phage display cDNA library with one patient's serum. There was first demonstrated that these clones bound to IgG molecules found in the sera of patients other than the one used for antigen selection. One hundred and forty nine markers that bound to IgGs in sera from OVCA patients showed no interaction with sera from cancer-free women. Forty-one of these antigen biomarkers had positive interactions with early (including cancers with borderline histology) and late stage ovarian cancer patients and there were no false positive interactions with IgGs in sera from either women having benign gynecological syndromes such as ovarian cysts and endometrial fibroids or sera from women with endometrial cancer. Because Stage I and Stage I borderline tumors can elicit a detectable immune response in this assay, this technology is sensitive to very small tumor burdens as (Table 5A). Sera from women with other cancers can be used to distinguish markers that are specific to ovarian cancer from those that bind to antibodies in sera from individuals with other cancers. Based on this representative sample of 480 clones from a single selection experiment, discovery of these markers to larger numbers of epitope clones were scaled up, cloning from additional libraries using sera from these and other women with ovarian cancer. Although the epitope markers were cloned using serum from a patient having the most common histologic type of ovarian cancer, serous adenocarcinoma, there has been shown that these markers are capable of detecting other histologic types of ovarian cancer, including endometrioid and clear cell tumors as well (Table 5A, Table 4). When the top ranking 26 (Table 7A) were applied, to the dataset comprised of 16 patients and 12 healthy women, these clones bound to IgGs in the sera from 16 out of 16 patients (Table 7B). As none of these 26 clones showed binding to IgGs in sera from 25 healthy women in Group 1 or 12 healthy women in Group 2, it is likely they represent a promising discriminator between the healthy and cancer sera. Larger studies with additional antigen biomarkers in other populations can be used to verify that the rate of diagnostic misclassification with this approach is small enough to justify its use in a clinical setting as screening test for ovarian cancer.

Knowledge regarding the immunogenicity and expression pattern of serologically-defined tumor antigens is critical in assessing the therapeutic and diagnostic potential of those antigens. The present study demonstrates that the use of T7 phage display selected clones is an effective technique for molecular profiling of the humoral immune response in ovarian cancer. Within this initial panel of 41 biomarkers, 8/9 contained large portions of open reading frames of the parental proteins; 1F6 is the receptor-binding cancer antigen expressed on SiSo cells (Human uterine adenocarcinoma cell line) (RCAS1); 3A9 is the signal recognition protein (SRP-19); 5C11 is the AHNAK-related sequence; 2B4, nuclear autoantogenic sperm protein (NASP); 3C11 is the Ribosomal protein L4 (RPL4); 4H3 is the Nijmegen breakage syndrome 1 (nibrin) (NBS1); 2G4 is the eukaryotic initiation factor 5A (elF-5A); and 5F8 is the *Homo sapiens* KIAA0419 gene product. With the exception of clone 4A11 that is the *Homo sapiens* chromodomain helicase DNA binding protein 1, CHD1, all of the aforementioned gene products have a known or suspected etiological association with cancer. One of these markers, RCAS1, is overexpressed in many cancers such as uterine, breast and pancreatic cancer. As indicated by the broad overexpression of RCAS1 in human cancers, some of the antigens identified may not be specific to ovarian cancer. However, this does demonstrate that the epitomics profiling of the humoral immune response in cancer patients can identify serum antibody markers that are relevant to the etiology of their cancer (e.g. overexpressed or mutated) with diagnostic and therapeutic value. Interestingly, these 9 antigens with parental open reading frames are predicted to be intracellular products. This finding is in agreement with reports using the SEREX procedure, whereby the majority of those antigens are also intracellular, and their probable release by necrosis or cell lysis at the tumor site is an initiating factor in eliciting an immune response.

The remaining 32 clones are mimotopes, defined as peptides capable of binding to the paratope of an antibody, but are unrelated in sequence to the natural protein that the antibody actually recognizes. Such peptides are usually identified by testing combinatorial peptide libraries obtained by chemical synthesis or phage display for their ability to bind monoclonal antibodies specific for discontinuous epitopes. This is analogous to the previous studies that have selected randomized peptide libraries on serum from Hepatitis B patients. Peptide mimotopes can potentially be used as a novel form of immunotherapy to induce a beneficial antitumor response. A mimotope derived from a phage display library can induce specific inhibition of the binding between tumor-inhibitory antibody and the Erb-2 receptor. Such mimotopes may represent a superior form of immunotherapy that may not elicit side effects due to autoimmunity to a natural protein.

In conclusion, using a combination of high throughput selection and array-based serological profiling that are called Epitomics®, there was isolated a panel of 41 antigens, including 8 antigens previously associated with cancer. Further work with larger panels of antigens analyzed on macroarrays or microarrays provide a comprehensive set of markers that can be evaluated using sera from other cancers for the specificity of an ovarian cancer test. This epitomics approach to antigenic profiling has applications to cancer, autoimmune diseases, and infectious diseases for diagnostic, therapeutic, and epidemiologic studies.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

TABLE 4

Tumor Histology and Stage of Patients' sera used for screening of ovarian cancer

| Blood Specimen ID # | Histology | Stage |
|---|---|---|
| MEC1* | serous adenocarcinoma | Unknown |
| MEC2 | serous adenocarcinoma | IIA |
| MEC16 | serous adenocarcinoma | IV |
| MEC20 | serous adenocarcinoma | Unknown |
| MEC23 | serous adenocarcinoma | IIIC |
| MEC35 | serous adenocarcinoma | IIIC |
| MEC37 | serous adenocarcinoma | IIIC |
| TB01-060 | serous adenocarcinoma | IIIC |
| TB01-108 | serous adenocarcinoma | IIIC |
| 42501 | adenocarcinoma NOS | late |
| 400162 | adenocarcinoma NOS | late |
| 40036 | adenocarcinoma NOS | late |
| 42780 | adenocarcinoma NOS | late |
| B755 | adenocarcinoma NOS | late |
| 40015 | adenocarcinoma NOS | late |
| OVC075 | serous adenocarcinoma | IIC |
| OVC015 | serous adenocarcinoma | IIIC |
| OVC035 | serous adenocarcinoma | IIIC |
| OVC007 | mixed epithelial | IIIC |
| OVC005 | Malignant Mized Mesodermal Tumor | IIIC |
| OVC063 | serous adenocarcinoma | III |
| OVC045 | serous adenocarcinoma | IIIC |
| NW0629 (4387) | endometrioid adenocarcinoma | IC |
| NW0453 (4679) | adenocarcinoma NOS | IC |
| NW0046 (4555) | borderline serous cystadenofibroma | IA |
| NW1181 (4283) | endometrioid adenocarcinoma | IA |
| OVC019 | mixed epithelial | IC |
| OVC087 | clear cell | IA |
| OVC078 | endometriod | IC |
| OVC070 | borderline serous | IC |
| OVC049 | mixed epithelial | IA |
| OVC079 | borderline serous | I |
| 33-38 | benign ovarian cyst | N/A |
| 92-96 | uterine myoma | N/A |
| 80-82 | endometrial adenocarcinoma | IIIA |
| 79-62 | endometrial adenocarcinoma | IIIA |
| 35-27 | benign ovarian cyst | N/A |
| 30-141 | benign ovarian cyst | N/A |
| 70-153 | endometrial adenocarcinoma | IB |
| 81-80 | endometrial adenocarcinoma | IA |
| 31-55 | benign ovarian cyst | N/A |
| 39-55 | benign ovarian cyst | N/A |
| 36-11 | endometrial polyp | N/A |
| 32-43 | Benign, thickening of endometrium | N/A |
| OVC068-1B | papillary serous adenoma (benign) & endometriosis | N/A |
| OVC054 | benign serous cystadenoma | N/A |

*Serum used for biopanning

TABLE 5A

Binding of 44 Clones with Late Stage and Stage I Ovarian Cancer Patient Sera

The binding of a panel of 44 clones with 22 Late Stage, 10 Stage I ovarian cancer patients was determined. These 44 antigens listed below bound exclusively with serum IgGs derived from both late stage and stage I ovarian cancer patients (including borderline histology) but not with serum IgG from normal control or patients with other gynecological diseases. The grey colored boxes represent positive binding of phage clones with patient's sera. TP: Total number of patients whose serum IgGs bound to each phage clone.
●: Serum Dilution 1:3000; •: Serum Dilution 1:30000; for others 1:10000 serum dilution was used.

TABLE 5A-continued

Binding of 44 Clones with Late Stage and Stage I Ovarian Cancer Patient Sera

The binding of a panel of 44 clones with 22 Late Stage, 10 Stage I ovarian cancer patients was determined. These 44 antigens listed below bound exclusively with serum IgGs derived from both late stage and stage I ovarian cancer patients (including borderline histology) but not with serum IgG from normal control or patients with other gynecological diseases. The grey colored boxes represent positive binding of phage clones with patient's sera. TP: Total number of patients whose serum IgGs bound to each phage clone.
•: Serum Dilution 1:3000; *: Serum Dilution 1:30000; for others 1:10000 serum dilution was used.

| | OVC045 | 4387 | 4679 | 4555 | 4283 | OVC019 | OVC087 | OVC078 | OVC070 | OVC049 | OVC079 | TP |
|---|---|---|---|---|---|---|---|---|---|---|---|---|
| 1B5 (SEQ ID NO: 44) | | | | | | | | | | | | 1 |
| 1F6 (SEQ ID NO: 11) | | | | | | | | | | | | 1 |
| 1H1 (SEQ ID NO: 48) | | | | | | | | | | | | 2 |
| 2A3 (SEQ ID NO: 27) | | | | | | | | | | | | 8 |
| 2B4 (SEQ ID NO: 12) | | | | | | | | | | | | 12 |
| 2C1 (SEQ ID NO: 40) | | | | | | | | | | | | 5 |
| 2C7 (SEQ ID NO: 33) | | | | | | | | | | | | 7 |
| 2D1 (SEQ ID NO: 38) | | | | | | | | | | | | 2 |
| 2E1 (SEQ ID NO: 34) | | | | | | | | | | | | 8 |
| 2E10 (SEQ ID NO: 37) | | | | | | | | | | | | 6 |
| 2E11 (SEQ ID NO: 30) | | | | | | | | | | | | 6 |
| 2E12 (SEQ ID NO: 43) | | | | | | | | | | | | 11 |
| 2F7 (SEQ ID NO: 13) | | | | | | | | | | | | 3 |
| 2F10 (SEQ ID NO: 49) | | | | | | | | | | | | 7 |
| 2F12 (SEQ ID NO: 52) | | | | | | | | | | | | 13 |
| 2G2 (SEQ ID NO: 41) | | | | | | | | | | | | 12 |
| 2G4 (SEQ ID NO: 14) | | | | | | | | | | | | 8 |
| 2H5 (SEQ ID NO: 51) | | | | | | | | | | | | 13 |
| 2H9 (SEQ ID NO: 22) | | | | | | | | | | | | 3 |
| 3A9 (SEQ ID NO: 15) | | | | | | | | | | | | 3 |
| 3B12 (SEQ ID NO: 23) | | | | | | | | | | | | 9 |
| 3C8 (SEQ ID NO: 47) | | | | | | | | | | | | 3 |
| 3C11 (SEQ ID NO: 16) | | | | | | | | | | | | 5 |
| 4A3 (SEQ ID NO: 35) | | | | | | | | | | | | 9 |
| 4A4 (SEQ ID NO: 25) | | | | | | | | | | | | 4 |
| 4A11 (SEQ ID NO: 17) | | | | | | | | | | | | 5 |
| 4B2 (SEQ ID NO: 45) | | | | | | | | | | | | 4 |
| 4C10 (SEQ ID NO: 28) | | | | | | | | | | | | 2 |
| 4D9 (SEQ ID NO: 29) | | | | | | | | | | | | 1 |
| 4G8 (SEQ ID NO: 36) | | | | | | | | | | | | 1 |
| 4G9 (SEQ ID NO: 42) | | | | | | | | | | | | 6 |
| 4H3 (SEQ ID NO: 18) | | | | | | | | | | | | 2 |
| 4H4 (SEQ ID NO: 32) | | | | | | | | | | | | 8 |
| 5A3 (SEQ ID NO: 26) | | | | | | | | | | | | 8 |
| 5C3 (SEQ ID NO: 19) | | | | | | | | | | | | 3 |
| 5C6 (SEQ ID NO: 46) | | | | | | | | | | | | 3 |
| 5C9 (SEQ ID NO: 53) | | | | | | | | | | | | 2 |
| 5C11 (SEQ ID NO: 20) | | | | | | | | | | | | 4 |
| 5C12 (SEQ ID NO: 50) | | | | | | | | | | | | 1 |
| 5D8 (SEQ ID NO: 24) | | | | | | | | | | | | 3 |
| 5F8 (SEQ ID NO: 21) | | | | | | | | | | | | 3 |
| 5F9 (SEQ ID NO: 54) | | | | | | | | | | | | 4 |
| 5G9 (SEQ ID NO: 31) | | | | | | | | | | | | 3 |
| 5H6 (SEQ ID NO: 39) | | | | | | | | | | | | 2 |

TABLE 5B

Binding of 21 Clones with Late Stage Ovarian Cancer Patient Sera

The binding of a panel of 21 clones with 22 Late Stage was determined on macroarrays. These 21 antigens listed below bound exclusively with serum IgGs derived from late stage ovarian cancer patients but not with serum IgG from normal control of patients with other gyenecological diseases.
•: Serum Dilution 1:3000; •: Serum Dilution 1:30000;
all others were analyzed at a serum dilution of 1:10000;
TP: Total number of patients whose serum IgGs bound to each phage clone.

| | Mec1 | Mec2 | Mec16 | Mec20 | Mec23 | Mec35Δ | Mec37Δ | TB01-060Δ | TCB01-108Δ | 42501 | 40162 | 40036 | 42780 | B755▲ | 40015 | OVC075 | OVC015 | OVC035 | OVC007 | OVC005 | OVC063 | OVC045 | TP |
|---|---|---|---|---|---|---|---|---|---|---|---|---|---|---|---|---|---|---|---|---|---|---|---|
| 2B3 (SEQ ID NO: 56) | | | | | | | | | | | | | | | | | | | | | | | 10 |
| 2B9 (SEQ ID NO: 57) | | | | | | | | | | | | | | | | | | | | | | | 3 |
| 2C12 (SEQ ID NO: 58) | | | | | | | | | | | | | | | | | | | | | | | 4 |
| 2D7 (SEQ ID NO: 59) | | | | | | | | | | | | | | | | | | | | | | | 2 |
| 2D12 (SEQ ID NO: 60) | | | | | | | | | | | | | | | | | | | | | | | 3 |
| 2E7 (SEQ ID NO: 61) | | | | | | | | | | | | | | | | | | | | | | | 2 |
| 2G10 (SEQ ID NO: 62) | | | | | | | | | | | | | | | | | | | | | | | 5 |
| 2G11 (SEQ ID NO: 63) | | | | | | | | | | | | | | | | | | | | | | | 6 |
| 2H8 (SEQ ID NO: 64) | | | | | | | | | | | | | | | | | | | | | | | 1 |
| 3H1 (SEQ ID NO: 55) | | | | | | | | | | | | | | | | | | | | | | | 1 |
| 4C5 (SEQ ID NO: 65) | | | | | | | | | | | | | | | | | | | | | | | 4 |
| 4H6 (SEQ ID NO: 66) | | | | | | | | | | | | | | | | | | | | | | | 7 |
| 5A2 (SEQ ID NO: 67) | | | | | | | | | | | | | | | | | | | | | | | 8 |
| 5A4 (SEQ ID NO: 74) | | | | | | | | | | | | | | | | | | | | | | | 3 |
| 5A7 (SEQ ID NO: 68) | | | | | | | | | | | | | | | | | | | | | | | 2 |
| 5B9 (SEQ ID NO: 69) | | | | | | | | | | | | | | | | | | | | | | | 1 |
| 5B12 (SEQ ID NO: 70) | | | | | | | | | | | | | | | | | | | | | | | 1 |
| 5D6 (SEQ ID NO: 71) | | | | | | | | | | | | | | | | | | | | | | | 2 |
| 5E3 (SEQ ID NO: 72) | | | | | | | | | | | | | | | | | | | | | | | 2 |
| 5E7 (SEQ ID NO: 75) | | | | | | | | | | | | | | | | | | | | | | | 2 |
| 5H8 (SEQ ID NO: 73) | | | | | | | | | | | | | | | | | | | | | | | 2 |

The mimotope sequences and the epitopes that are the real antigens that the antibodies were produced against based on the amino acid sequence homology similarity (see below Region of similarity of AA).

TABLE 6A

Description of Stage I-IV clones.
Size range of the Mimotopes ≥5 amino acids

| Stage (I-IV) clones | Description of the genes that are in-frame with T7 10B gene | Peptide sequences of Epitopes, in frame with T7 B gene | Size of the peptide | Unigene # | Region of similarity of AA | Antigen expression in any type of cancer |
|---|---|---|---|---|---|---|
| 1F6 | gi\|18490914\|gb\|BC022506.1\| Homo sapiens, estrogen receptor binding site associated, antigen, 9 RCAS | AAWQAEEVLR-QQKLADREKR-AAEQQ (SEQ ID NO:11) | 25 AA | Hs.9222 | 165-213 | Overexpressed in ovarian, nonsmall cell lung carcinoma, pancreatic ductal cacinoma |
| 2B4 | gi\|22042983\|ref\|XM_032391.3\|, Homo sapiens similar to nuclear autoantigenic sperm protein (histone-binding)(NASP) | EKGGQEKQGEVIVSI-EEKPKEVXEEQPVVT-LEKQGTAVEVEAESL-DPTVKPVDVGGDEPE-EEKVVTSENEAGKAV-LEQLVGQEVPPAEESP-EVTTEAAEASAVEAGS-EVSEKPGQEAPVLPKD-GAVNGPSVVGDQTPIE-PQTSIERLTETKDGSGL-EEKVRAKLVPSQEETK-LSVEESEAAGDGVDTK-VAQGATEKSPEDKVQI-AANEETQER (SEQ ID NO: 12) | 212 AA | Hs.446206 | 258-469 | Expression levels are higher in myelogenous leukemia and lymphoblastic leukemia cells. |
| 2F7 | gi\|22042983\|ref\|XM_032391.3\|, Homo sapiens similar to Nuclear autoantigenic sperm protein (NASP) | EKGGQEKQGEVIVSI (SEQ ID NO: 13) | 15 AA | Hs.446206 | 256-270 | Expression levels are higher in myelogenous leukemia and lymphoblastic leukemia cells. |
| 2G4 | gi\|20987351\|gb\|BC030160.1\|, Homo sapiens, eukaryotic translation initiation factor 5A | MADDLDFETGDAGASA-TFPMQCSALRKNGFVV-LKGRPCKIVEMSTSKTG-KHGHAKVHLVGIDIFTG-KKYEDICPSTHNMDVPN-IKRNDFQLIGIQDGYLSL-LQDSGEVREDLRLPEGD-LGKEIHKFDCGFQILIT-VLSAMTEEALVA (SEQ ID NO: 14) | 148 AA | Hs.310621 | 1-148 | eIF-5A2 sharing 82% identity of amino acid sequence with eIF-5A, is a candidate oncogene related to development of ovarian cancer. |
| 3A9 | gi\|4507212\|ref\|NM_003135.1\|, Homo sapiens signal recognition particle 19 kDa (SRP19) | QKTGGADQSLQQGEGS-KKGKGKKKK (SEQ ID NO: 15) | 25 AA | Hs.2943 | 119-143 | Transcript generated by alternative splicing between exon 14 of the Adenomatous polyposis coli gene and SRP19 is observed and it's expression is higher in Colorectal cancer |
| 3C11 | gi\|16579884\|ref\|NM_000968.2\| Homo sapiens ribosomal protein L4 (RPL4) | ALQAKSDEKAAVAGKK-PVVGKKGKKAAVGVKK-QKKPLVGKKAAATKKPS-PEKKPAENKPTTEDNKP-AA (SEQ ID NO: 16) | 68 AA | Hs.186350 | 360-427 | over-expression of L7a and L37 mRNA is confirmed in prostate-cancer tissue samples. |

TABLE 6A-continued

| | | Size of the peptide | Description of Mimotopes mimic | Unigene # | Region of similarity of AA | Antigen expression in any type of cancer |
|---|---|---|---|---|---|---|
| 4A11 | gi|4557446|ref|NM_001270.1|, *Homo sapiens* chromodomain helicase DNA binding protein 1 (CHD1) | 86 AA | QQQQQQHQASSNSGSE-EDSSSSEDSDDSSSEVKR-KKHKDEDWQMSGSGSP-SQSGSDSESEEEREKSSC-DETESDYEPKNKVKSRK (SEQ ID NO: 17) | Hs.311553 | 107-192 | Not associated with cancer |
| 4H3 | gi|20543465|ref|XM_045343.5|, *Homo sapiens* Nijmegen breakage syndrome 1 (nibrin) (NBS1) | 101 AA | PTKLPSINKSKDRASQQQ-QTNSIRNYFQPSTKKRER-DEENQEMSSCKSARIETS-CSLLEQTQPATPSLWKN-KEQHLSENXPVDTXXSX-NLFTGYXFRXGXE (SEQ ID NO: 18) | Hs.25812 | 433-524 | Three different mutations in NBS1 gene, generating truncated or aberrant NBS1 transcripts were observed in different cancer cell lines. |
| 5C3 | gi|20987351|gb|BC030160.1|, *Homo sapiens*, eukaryotic translation initiation factor 5A | 118 AA | MADDLFETGDAGASA-TFPMQCSALRKNGFVVL-KGRPCKIVEMSTSKTGK-HGHAKVHLVGIDIFTGK-KYEDICPSTHNMDVPNI-KRNDFQLIGIQDGYLSLL-QDSGEVREDLPLPEGD (SEQ ID NO: 19) | Hs.310621 | 1-118 | eIF-5A2 sharing 82% identity of amino acid sequence with eIF-5A, is a candidate oncogene related to development of ovarian cancer. |
| 5C11 | gi|535176|emb|X74818.1| HSAHNAKRS, *H. sapiens* mRNA of AHNAK-related sequence | 121 AA | PKFKMPDVHFKSPQISM-SDIDLNLKGPKIKGDMD-ISVPKLEGDLKGPKVDVK-GPKVGIDTPDIDHGPEGK-LKGPKFKMPDLHLKAPKI-SMPEVDLNLKGPKVKGD-MDISLPKVEGDLKGP (SEQ ID NO: 20) | Hs.378738 | 393-512 | Expression level of AHNAK is higher in melanoma, promyelocytic leukemia HL-60, osteosarcoma. |
| 5F8 | gi|7662105|ref|NM_014711.1|, *Homo sapiens* KIAA0419 gene product | 150 AA | GVCSSKVYVGKNTSEVK-EDVVLGKSNQVCQSSGN-HLENKVTHGLVTVEGQL-TSDERGAHIMNSTCAAM-PKLHEPYASSQCIASPNF-GTVSGLKPASMLEKNCSL-QTELNKSYDVKNPSPLLM-QNQNXRQQMDTPMVSC-GNFQFLDNSFEK (SEQ ID NO: 21) | Hs.279912 | 434-583 | mRNA expression level of another antigen KIAA1416 is up-regulated in colon cancer. |

The above table shows two antigens and not mimotopes, the clones below are the mimotopes.

| Stage (I-IV) clones | Description of the genes that are in Mimotope clones | Peptide sequences of Mimotopes of Mimotopes, in-frame with T7 10 B gene | Size of the peptide | Description of sequences that Mimotopes mimic | Unigene # | Region of similarity of AA | Antigen expression in any type of cancer |
|---|---|---|---|---|---|---|---|
| 2H9 | gi|21619682|gb|BC032762.1|, *Homo sapiens* optineurin, mRNA | ELLRT (SEQ ID NO: 22) | 5 AA | gi|20139301|sp|Q9Y446| PKP3_HUMAN, Plakophilin 3 | Hs.148074 | 407-411 Score = 18.9 bits (37), Expect = 827 Identities = 5/5 (100%), Positives = 5/5 (100%) | Immunohistochemical localization of plakophilins (PKP1, PKP2, PKP3, and p0071) in primary |

| | | | Query[b]: 1 ELLRT 5 ELLRT Sbjct[c]: 407 ELLRT 411 | |
|---|---|---|---|---|
| 3B12 | gi\|21735624\|ref\|NM_145690.1\|, *Homo sapiens* tyrosine 3-monooxygenase/tryptophan 5-monooxygenase activation protein, zeta polypeptide (YWHAZ), transcript variant 2, mRNA. | GQTSM (SEQ ID NO: 23) | Hs.370771 144-147 Score = 16.8 bits (32), Expect = 3595 Identities = 4/4 (100%), Positives = 4/4 (100%) Query: 2 QTSM 5 QTSM Sbjct: 144 QTSM 147 | gi\|729143\|sp\|P38936\| CDN1_HUMAN, Cyclin-dependent kinase inhibitor 1 (p21) (CDK-interacting protein1) (Melanoma differentiation associated protein 6) (MDA-6) | oropharyngeal tumors mda-6(p21) may function as a negative regulator of melanoma growth, progression and metastasis |
| 5D8 | gi\|22024583\|gb\|AC087376.5\|, *Homo sapiens* chromosome 11, clone RP11-230O19, complete sequence | KKGPI (SEQ ID NO: 24) | Hs.153714 102-106 Score = 18.5 bits (36), Expect = 1109 Identities = 5/5 (100%), Positives = 5/5 (100%) Query: 1 KKGPI 5 KKGPI Sbjct: 102 KKGPI 106 | gi\|20177863\|sp\|Q9BXJ2\| CQT7_HUMAN, Complement-c1q and tumor necrosis factor-related protein 7 precursor | TNF-alpha regulates expression of downstream components of complement system and plays a role in energy homeostatis where it is implicated in cachexia, obesity and insulin resistance. |
| 4A4 | gi\|17028354\|gb\|BC017483.1\| BC017483, *Homo sapiens*, clone IMAGE: 3506553, mRNA. | AKVIMR (SEQ ID NO: 25) | Hs.150595 138-142 Score = 20.6 bits (41), Expect = 255 Identities = 5/5 (100%), Positives = 5/5 (100%) Query: 2 KVIMR 6 KVIMR Sbjct: 138 KVIMR 142 | gi\|5921908\|sp\|O43174\| CP26_HUMAN, Cytochrome P450 26 (Retinoic acid-metabolizing cytochrome) (P450RAI) (hP450RAI) (Retinoic acid 4-hydroxylase) | all-trans-Retinoic acid-induced expression and regulation of retinoic acid 4-hydroxylase (CYP26) in human promyelocytic leukemia |
| 5A3 | gi\|15011541\|gb\|AF397158.1\| AF397158, *Homo sapiens* clone 11 pur alpha-associated ribosomal RNA gene, partial sequence | YACLKD (SEQ ID NO: 26) | Hs.433103 351-355 Score = 20.2 bits (40), Expect = 342 Identities = 5/5 (100%), Positives = 5/5 (100%) Query: 1 YACLK 5 YACLK Sbjct: 351 YACLK 355 | gi\|1170473\|sp\|P42575\| ICE2_HUMAN, Caspase-2 precursor (CASP-2) (ICH-1 protease) | CASP-3, CASP-4, CASP-2 heterogeneously coexpress in leukemic cell lines |
| 2A3 | gi\|23271193\|gb\|BC036014.1\|, *Homo sapiens* | QILFMDP (SEQ ID NO: 27) | Hs.222405 242-246 Score = 21.4 bits (43), Expect = 142 | gi\|729597\|sp\|P39086\| GLK1_HUMAN, Glutamate receptor, | Ionotropic and metabotropic glutamate receptor |

TABLE 6A-continued

| | | | | | |
|---|---|---|---|---|---|
| 4C10 | poly (A) polymerase alpha, mRNA gi|24756892|gb|AC008507.10|, *Homo sapiens* chromosome 19 clone CTC-448F2, complete sequence | LNTVNTLI (SEQ ID NO: 28) | ionotropic kainate 1 precursor | Hs.416077 | Identities = 5/5 (100%), Positives = 5/5 (100%) Query: 1 QILFM 5 QILFM Sbjct: 242 QILFM 246 | protein expression in glioneuronal tumours from patients with intractable epilepsy |
| 4D9 | gi|21629397|gb|AC099571.2|, *Homo sapiens* chromosome 1 clone RP11-438H8, complete sequence | GNSILLIA (SEQ ID NO: 29) | gi|13633936|sp|Q9NPR2| SM4B_HUMAN, Semaphorin 4B | Hs.81874 | 440-445 Score = 21.8 bits (44), Expect = 106 Identities = 6/6 (100%), Positives = 6/6 (100%) Query: 1 NTVNTL 6 NTVNTL Sbjct: 440 NTVNTL 445 | Not associated with cancer |
| 2E11 | gi|22004067|dbj|AP005356.2|, *Homo sapiens* genomic DNA, chromosome 8q23, clone: KB1198A4, complete sequence. | WDLKSEYS (SEQ ID NO: 30) | gi|2842764|sp|Q99735| GST2_HUMAN, Microsomal glutathione S-transferase 2 (Microsomal GST-2) | Hs.386726 | 3-10 Score = 21.4 bits (43), Expect = 140 Identities = 7/8 (87%), Positives = 7/8 (87%) Query: 1 GNSILLIA 8 GNSILL A Sbjct: 3 GNSILLAA 10 | GST-pi has significance in the diagnosis of cancers as it is expressed abundantly in tumor cells. |
| 5G9 | gi|20072204|gb|BC026241.1|, *Homo sapiens* ubiquitin-protein isopeptide ligase (E3), mRNA | PGCSTTLS (SEQ ID NO: 31) | gi|17101461|sp|P49798| RGS4_HUMAN, Regulator of G-protein signaling 4 (RGS4) (RGP4) | Hs.255596 | 80-85 Score = 21.8 bits (44), Expect = 106 Identities = 6/6 (100%), Positives = 6/6 (100%) Query: 3 LKSEYS 8 LKSEYS Sbjct: 80 LKSEYS 85 | RGS4 is highly expressed in brain regions implicated in pathophysiology of sizophrenia |
| 4H4 | gi|20072204|gb|BC026241.1|, *Homo sapiens* ubiquitin-protein isopeptide ligase (E3), mRNA | PRCSTTLS (SEQ ID NO: 32) | gi|14423962|gb|O94966| UBPJ_HUMAN, Ubiquitin carboxyl-terminal hydrolase 19 | Hs.128433 | 940-947 Score = 18.9 bits (37), Expect = 827 Identities = 6/8 (75%), Positives = 7/8 (87%) Query: 1 PGCSTTLS 8 PGC+T LS Sbjct: 940 PGCTTLLS 947 | Ubiquitin carboxyl-terminal-hydrolase L1 genes cause autosomal dominant familial Parkinson disease. |
| 2C7 | gi|3152628|gb|AC004744.1|AC004744, | GDRSQLWRK (SEQ ID NO: 33) | gi|6225843|sp|O60760| PGD2_HUMAN, Glutathione-requiring prostaglandin D synthase | | 156-160 Score = 18.9 bits (37), Expect = 827 Identities = 5/5 (100%), Positives = 5/5 (100%) Query: 3 CSTTL 7 CSTTL Sbjct: 156 CSTTL 160 | Lipocalin-type prostaglandin D synthase (L-PGDS) has recently been shown to be expressed in human brain tumors, breast tumors and in ovarian cancer |
| | | | gi|24211441|sp|Q13443| AD09_HUMAN, ADAM 9 precursor (A | Hs.2442 | 720-725 Score = 20.2 bits (40), Expect = 342 | Expression of ADAM-9 mRNA and protein in |

TABLE 6A-continued

| | | | | | | |
|---|---|---|---|---|---|---|
| | Homo sapiens BAC clone GS1-465N13 from 7, complete sequence | KKQSSWYQI (SEQ ID NO: 34) | 9 AA | disintegrin and metalloproteinase domain 7) | Identities = 5/6 (83%), Positives = 5/6 (83%), Query: 3 RSQLWR 8 R QLWR Sbjct: 720 RDQLWR 725 | human breast cancer |
| 2E1 | gi|16160856|ref|XM_007763.5|, Homo sapiens myosin VA (heavy polypeptide 12, myoxin) (MYO5A), mRNA | KKQSSWYQI (SEQ ID NO: 34) | 9 AA | gi|2498310|sp|Q12882| DPYD_HUMAN Dihydropyrimidine dehydrogenase [NADP+] precursor (DPD) (DHPDHase) (Dihydrouracil dehydrogenase) (Dihydrothymine dehydrogenase) | Hs.1602 | 497-502 Score = 21.8 bits (44), Expect = 106 Identities = 5/6 (83%), Positives = 6/6 (100%) Query: 2 KQSSWY 7 KQ+SWY Sbjct: 497 KQASWY 502 | Higher DPD activity in gastric cancer is observed than in colorectal cancer |
| 4A3 | gi|16160856|ref|XM_007763.5|, Homo sapiens myosin VA (heavy polypeptide 12, myoxin) (MYO5A), mRNA | KKQSSWYQI (SEQ ID NO: 35) | 9 AA | gi|2498310|sp|Q12882| DPYD_HUMAN Dihydropyrimidine dehydrogenase [NADP+] precursor (DPD) (DHPDHase) (Dihydrouracil dehydrogenase) (Dihydrothymine dehydrogenase) | Hs.1602 | 497-502 Score = 21.8 bits (44), Expect = 106 Identities = 5/6 (83%), Positives = 6/6 (100%) Query: 2 KQSSWY 7 KQ+SWY Sbjct: 497 KQASWY 502 | Higher DPD activity in gastric cancer is observed than in colorectal cancer |
| 4G8 | gi|15778776|gb|AC012363.6|, Homo sapiens BAC clone RP11-438O12 from 2, complete sequence | PEGGTDASR (SEQ ID NO: 36) | 9 AA | gi|13634077|sp|Q9Y493| ZAN_HUMAN, Zonadhesin | Hs.307004 | 1912-1919 Score = 18.9 bits (37), Expect = 827 Identities = 6/8 (75%), Positives = 7/8 (87%) Query: 2 EGGTDASR 9 EGGT+A R Sbjct: 1912 EGGTEAFR 1919 | zonadhesin functions during fertilization to anchor the acrosomal shroud to the zona pellucida |
| 2E10 | gi|20521965|dbj|AB051476.2|, Homo sapiens mRNA for KIAA1689 protein, partial cds | ASFTLKLQS (SEQ ID NO: 37) | 9 AA | gi|6226869|sp|P34932| HS74_HUMAN, HEAT SHOCK 70 KDA PROTEIN 4 (HEAT SHOCK 70-RELATED PROTEIN APG-2) | Hs.90093 | 647-653 Score = 21.8 bits (44), Expect = 106 Identities = 6/7 (85%), Positives = 7/7 (100%) Query: 2 SFTLKLQ 8 SFTLKL+ Sbjct: 647 SFTLKLE 653 | Expression of HSP70 is observed in human hepatocellular carcinoma |
| 2D1 | gi|4504522|ref|NM_002157.1|, Homo sapiens heat shock 10 kDa protein 1 (chaperonin 10) (HSPE1), mRNA | GGGSNGRTSV (SEQ ID NO: 38) | 10 AA | gi|20137621|sp|O95071| EDD_HUMAN, Ubiquitin–protein ligase EDD (Hyperplastic discs protein homolog)(hHYD) (Progestin induced protein) | Hs.94262 | 140-148 Score = 21.8 bits (44), Expect = 105 Identities = 7/9 (77%), Positives = 9/9 (100%) Query: 1 GGGSNGRTS 9 GGGS+GR+S Sbjct: 140 GGGSSGRSS 148 | EDD, the human orthologue of the hyperplastic discs tumour suppressor gene, is amplified and overexpressed in cancer |

TABLE 6A-continued

| | | | | | |
|---|---|---|---|---|---|
| 5H6 | gi|40849829|gb|AAR95625| NADH dehydrogenase subunit 4 | NSFLMTSSKPR (SEQ ID NO: 39) | 11 AA | Hs.334087 | 694-699 Score = 20.6 bits (41), Expect = 254 Identities = 5/6 (83%), Positives = 6/6 (100%) Query: 1 NSFLMT 6 NS+LMT Sbjct: 694 NSYLMT 699 | |
| | gi|12643618|sp|O60242| BAI3_HUMAN, Brain-specific angiogenesis inhibitor 3 precursor | | | | | BAI1 expression inhibit stromal vascularization in pulmonary adenocarcinoma |
| 2C1 | gi|23958536|gb|BC036216.1|, Homo sapiens cullin 4B, mRNA | ACSSTVSFIWI (SEQ ID NO: 40) | 11 AA | Hs.160871 | 623-629 Score = 21.8 bits (44), Expect = 128 Identities = 6/7 (85%), Positives = 7/7 (100%) Query: 3 SSTVSFI 9 SST+SFI Sbjct: 623 SSTISFI 629 | |
| | gi|33112422|sp|Q16827| PTPO_HUMAN Receptor-type protein-tyrosine phosphatase O precursor (Glomerular epithelial protein 1) (Protein tyrosine phosphatase U2)(PTPase U2) (PTP-U2) | | | | | Functional involvement of PTP-U2L in apoptosis subsequent to terminal differentiation of monoblastoid leukemia cells |
| 2G2 | gi|25988997|gb|AF 541939.1|, His-3 integration vector pJHAM007, complete sequence | KKKKKKKRVGGPLQ (SEQ ID NO: 41) | 14 AA | Hs.363492 | 108-115 Score = 27.4 bits (57), Expect = 2.8 Identities = 8/8 (100%), Positives = 8/8 (100%) Query: 1 KKKKKKKR 8 KKKKKKKR Sbjct: 108 KKKKKKKR 115 | |
| | gi|20532388|sp|Q9NVP1| DD18_HUMAN, ATP-dependent RNA helicase DDX18 (DEAD-box protein 18)(Myc-regulated DEAD-box protein (MrDb) | | | | | The expression of MrDb is induced upon proliferative stimulation of primary human fibroblasts as well as B cells and down-regulated during terminal differentiation of HL60 leukemia cells |
| 4G9 | gi|17136149|ref|NM_014708.2|, Homo sapiens kinetochore associated 1 (KNTC1), mRNA | GPVFICSSNCFKIT (SEQ ID NO: 42) | 14 AA | Hs.75360 | 333-340 Score = 24.4 bits (50), Expect = 18 Identities = 7/8 (87%), Positives = 8/8 (100%) Query: 7 SSNCFKIT 14 SSNCF+IT Sbjct: 333 SSNCFEIT 340 | |
| | gi|115892|sp|P16870| CBPH_HUMAN, Carboxypeptidase H precursor (CPH) (Carboxypeptidase E) (CPE) (Enkephalin convertase) (Prohormone processing carboxypeptidase) | | | | | Expression of the protein product of the PCPH proto-oncogene in human tumor cell lines |
| 2E12 | gi|22062543|ref|XM_170670.1|, Homo sapiens putative transmembrane protein; homolog of yeast Golgi membrane protein Yif1p (Yif1p-interacting factor) (54TM), mRNA. | APFTCWPTVAINTWE (SEQ ID NO: 43) | 15 AA | Hs.307734 | 167-175 Score = 23.5 bits (48), Expect = 32 Identities = 7/10 (70%), Positives = 7/10 (70%), Gaps = 1/10 (10%) Query: 6 WPTVAINTWE 15 WP VAT WE Sbjct: 167 WP-VAITENWE 175 | |
| | gi|128062|sp|P08473| NEP_HUMAN, Neprilysin (Neutral endopeptidase) (NEP)(Enkephalinase) (Common acute lymphocytic leukemia antigen) (CALLA)(Neutral endopeptidase 24.11) (CD10) | | | | | Loss or decrease in expression of NEP has been reported in brain cancer, renal cancer and invasive bladder cancer. |

TABLE 6A-continued

| | | | | | |
|---|---|---|---|---|---|
| 1B5 | gi|12654862|gb|BC001275.1|BC001275, *Homo sapiens* annexin A1, mRNA | TDQSSISPGNRKAPG (SEQ ID NO: 44) | 15 AA | gi|6707734|sp|Q13077|TRA1_HUMAN, TNF receptor associated factor 1 (TRAF1) | Hs.531251 | 64-70 Score = 21.0 bits (42), Expect = 187 Identities = 6/7 (85%), Positives = 7/7 (100%) Query: 5 SISPGNR 11 SISPG+R Sbjct: 64 SISPGSR 70 | Tumor necrosis factor receptor-associated factor 1 gene overexpression in B-cell chronic lymphocytic leukemia |
| 4B2 | gi|23272851|gb|BC035645.1|, *Homo sapiens*, Similar to RIKEN cDNA 3830613O22 gene, clone | RIMGGGIQRETWISS (SEQ ID NO: 45) | 15 AA | gi|20139133|sp|Q9BZF3|ORP6_HUMAN, Oxysterol binding protein-related protein 6 | Hs.318775 | 906-912 Score = 21.8 bits (44), Expect = 104 Identities = 5/7 (71%), Positives = 6/7 (85%) Query: 8 QRETW IS 14 QRE W+S Sbjct: 906 QREAWVS 912 | Oxysterols are potent signalling lipids that directly bind liver X receptors (LXRs). Oxysterol-regulated function of LXRs is to control the expression of genes involved in reverse cholesterol transport, catabolism of cholesterol, and lipogenesis |
| 5C6 | gi|22797897|emb|AL160171.27|, Human DNA sequence from clone RP11-256E16 on chromosome 1, complete sequence | ICGSWGKYNLWQSSSSK (SEQ ID NO: 46) | 17 AA | gi|12644310|sp|P53618|COPB_HUMAN, Coatomer beta subunit (Beta-coat protein) (Beta-COP) | Hs.3059 | 250-257 Score = 22.3 bits (45), Expect = 93 Identities = 7/8 (87%), Positives = 7/8 (87%) Query: 8 YNLWQSSS 15 YNL QSSS Sbjct: 250 YNL LQSSS 257 | A major component of the coat of non-clathrin-coated vesicles, beta-COP, mediate membrane traffic through the Golgi complex |
| 3C8 | gi|24234687|ref|NM_004134.3|, *Homo sapiens* heat shock 70 kDa protein 9B (mortalin-2) (HSPA9B), nuclear gene encoding mitochondrial protein, mRNA. | EILKPEGQHMKLRSEETS (SEQ ID NO: 47) | 18 AA | gi|2493676|sp|Q12889|OGP_HUMAN, Oviduct-specific glycoprotein precursor (Oviductal glycoprotein) | Hs.1154 | 585-599 Score = 24.4 bits (50), Expect = 21 Identities = 10/15 (66%), Positives = 10/15 (66%), Gaps = 1/15 (6%) Query: 5 PEGQHMKLRSEE-TS 18 PEGQ M LR E TS Sbjct: 585 PEGQTM PLRGENLTS 599 | Oviduct specific glycoproteins are involved in variety of roles during fertilization and early embryonic development |
| 1H1 | gi|22024587|gb|AC103702.3|, *Homo sapiens* chromosome 17, clone RP11-357H14, complete sequence | AKARALARRSEPCSTGKLQLR (SEQ ID NO: 48) | 21 AA | gi|12230848|sp|O95049|ZO3_HUMAN, Tight junction protein ZO-3 (Zonula occludens 3 protein) | Hs.25527 | 853-862 Score = 23.5 bits (48), Expect = 38 Identities = 8/10 (80%), Positives = 8/10 (80%) Query: 3 ARALARRSEP 12 A ALAR SEP Sbjct: 853 APALARS SEP 862 | Occludin expression in microvessels of neoplastic and non-neoplastic human brain |

TABLE 6A-continued

| | | | | | | |
|---|---|---|---|---|---|---|
| 2F10 | gi|21166212|gb|AC109584.2|, Homo sapiens chromosome 3 clone RP11-674P14, complete sequence | VQRGIGTIPSETIPVNRKRVNPP (SEQ ID NO: 49) | 23 AA | gi|118206|sp|P14416| D2DR_HUMAN, D(2) dopamine receptor | Hs.73893 | 264-270 Score = 22.7 bits (46), Expect = 56 Identities = 6/7 (85%), Positives = 7/7 (100%) Query: 14 PVNRKRV 20 PVNR+RV Sbjct: 264 PVNRRRV 270 | Expression of dopamine receptors and transporter in neuroendocrine gastrointestinal tumor cells |
| 5C12 | gi|24430032|emb|AL939123.1| SCO939123, Streptomyces coelicolor A3(2) complete genome; segment 20/29 | VSWFPSWARSCGRQTPLGA TYKDTLLPV (SEQ ID NO: 50) | 28 AA | gi|3915660|sp|Q16850| CP51_HUMAN, Cytochrome P450 51A1 (CYPL1) (P450LI) (Sterol 14-alpha demethylase) (Lanosterol 14-alpha demethylase) (LDM) (P450-14DM) | Hs.512872 | 283-292 Score = 24.4 bits (50), Expect = 17 Identities = 8/10 (80%), Positives = 8/10 (80%) Query: 14 QTPLGATYKD 23 QT L ATYKD Sbjct: 283 QT LLDATYKD 292 | CYP2E1 protein is expressed in both tumour and normal breast tissue with an increased expression in breast tumours. |
| 2H5 | gi|18606292|gb|BC022865.1| Homo sapiens ATP synthase, H+ transporting, mitochondrial F1 complex, O subunit (oligomycin sensitivity conferring protein), mRNA | DLQPPGRRWLPQQCPGSPG RCDASVPLWSDHLPSL (SEQ ID NO: 51) | 35 AA | gi|116006|sp|P08575| CD45_HUMAN, Leukocyte common antigen precursor (L-CA) | Hs.444324 | 40-49 Score = 23.5 bits (48), Expect = 41 Identities = 8/10 (80%), Positives = 8/10 (80%) Query: 24 SVPLWSDHLP 33 SVPL SD LP Sbjct: 40 SVPLS SDPLP 49 | Expression of leucocyte-common antigen and large sialoglycoprotein on leukemic cells in B-cell chronic lymphocytic leukemia and non-Hodgkin's |
| 2F12 | gi|10443350|emb|AL133264.10| AL133264, Human DNA sequence from clone RP3-369A17 on chromosome 6p22.1-22.3 Contains ESTs, STSs, GSSs and CpG islands | RGLGPLAAACGRSGGGGG GAGGTGSSNVNKKTPPN (SEQ ID NO: 52) | 36 AA | gi|8928460|sp|O75962| TRIO_HUMAN, Triple functional domain protein (PTPRF interacting protein) | Hs.519209 | 2232-2244 Score = 31.2 bits (66), Expect = 0.22 Identities = 11/13 (84%), Positives = 13/13 (100%) Query: 13 SGGGGGGGAGGTG 25 SGGGGGGG+GG+G Sbjct: 2232 SGGGGGGGSGGSG 2244 | Not associated with cancer |
| 5C9 | gi|15072584|emb|AL442003.8|, Human DNA sequence from clone | PMRCSCTMGEIQMQIHCGAR RRKAVPSSKDNVQSSAH (SEQ ID NO: 53) | 37 AA | gi|34395516|sp|O15085| ARHB_HUMAN, Rho guanine nucleotide exchange factor 11 (PDZ-RhoGEF) | Hs.371602 | 409-417 Score = 23.1 bits (47), Expect = 72 Identities = 7/9 (77%), Positives = 7/9 (77%) | A novel gene at 11q23 named LARG for leukemia-associated Rho guanine nucleotide |

TABLE 6A-continued

| | | | | | |
|---|---|---|---|---|---|
| | RP11-324H6 on chromosome 10, complete sequence | | | Query: 8 MGEIQMQIH 16<br>M EIQ QIH<br>Sbjct: 409 MPEIQEQIH 417 | exchange factor (GEF) has strong sequence homology to several members of the Rho family of GEFs. Further, LARG was found to be fused with MLL in a patient with primary Rho GEF, Bcr, has been implicated in leukemia through a recurrent chromosomal translocation. |
| 5F9 | gi\|18693518\|gbl AC015911.8\|, *Homo sapiens* chromosome 17, clone RP11-1094M14, complete sequence | WRITYISILNLAQFYYSLITVLK TFNWPGTVVHACNPSTLGGQ GRRIT (SEQ ID NO: 54) | 48 AA | gi\|20139105\|sp\|Q99959\| PKP2_HUMAN, Plakophilin 2 | Hs.25051 | 471-492<br>Score = 47.4 bits (111),<br>Expect = 5e-06<br>Identities = 19/22 (86%),<br>Positives = 19/22 (86%)<br>Query: 27<br>WPGTVVHACNPSTLGGQG RRIT 48<br>WPG V<br>HACNPSTLGGQG RIT<br>Sbjct: 471<br>WPGAVAHACNPSTLGGQG GRIT 492 | Immunohistochemical localization of plakophilins (PKP1, PKP2, PKP3, and p0071) in primary oropharyngeal tumors |

TABLE 6B

Description of Stage II-IV clones.
Size range of the Mimotopes ≥5 amino acids

| Stage (II-IV) clones | Description of the genes that are in-frame with T7 10B gene | Peptide sequences of Epitopes in frame with T7 10B gene | Size of the peptide | Unigene # | Serex Y/N mRNA | Region of similarity of AA | Antigen expression in any type of cancer |
|---|---|---|---|---|---|---|---|
| 3H1 | gi|12654010|gb|BC000805.1| *Homo sapiens* nuclear ubiquitous casein kinase and cyclin-dependent kinase substrate, mRNA | DDDSDYGSSKKKNXKMVKKSKPERKEKKMPKPRLKAITV TPSPVKKGKGKVGRPTASKASKEKTPSPKEEDEPESPP EKKTSISPPPEKSGDEGSEDEAPSGED (SEQ ID NO: 55) | 103 AA | Hs.510265 | N | 140-243 | The expressions of casein kinase II (CK2) is higher in neoplastic ovarian surface epithelium. Casein kinase II (CK II) is expressed at a higher level in lung tumours. |
| 2B3 | gi|7023439|dbj|AK001891.1|, *Homo sapiens* cDNA FLJ11029 fis, clone PLACE1004156 | LSTSSFDEQN (SEQ ID NO: 56) | 10 AA | Hs.528654 | N | 350-360 | Not associated with cancer |

The table above are two antigens and not mimotopes, the clones below are the mimotopes.

| Stage (II-IV) clones | Description of the genes that are in Mimotope clones | Peptide sequences of the Mimotopes that are in-frame with T7 10 B gene | Size of the peptide | Description of the sequences that Mimotopes mimic | Unigene # | Region of similarity of | Antigen expression in any type of cancer |
|---|---|---|---|---|---|---|---|
| 2B9 | gi|28837315|gb| BC047588.1| *Homo sapiens* KIAA1363 protein, mRNA | VIVVLIAVISFPQNYTWL (SEQ ID NO: 57) | 18 AA | gi|20141211|sp|P18825| A2AC_HUMAN, Alpha-2C-adrenergic receptor (Alpha-2C adrenoceptor) (Subtype C4) | Hs.123022 | AA 172-185 Score = 24.8 bits (51), Expect = 16 Identities = 10/14 (71%), Positives = 10/14 (71%), Gaps = 3/14 (21%) Query: 2 IVV---LI-AVISFP 12 IV LI AVISFP Sbjct: 172 IVAVWLISAVISFP 185 | Stimulation of alpha2-adrenergic receptor inhibits cholangio-carcinoma growth through modulation of Raf-1 and B-Raf activities. Beta adrenergic receptor is overexpressed in pulmonary adenocarcinoma |
| 2C12 | gi|15072584|emb| AL442003.8|, Human DNA sequence from clone RP11-324H6 on chromosome 10, complete sequence | PMRCSCTMGEIQMQIHC GARRRKAVPSSKDNVQ SSAH (SEQ ID NO: 58) | 37 AA | gi|2851534|sp|Q13724| GCS1_HUMAN Mannosyl-oligosaccharide glucosidase (Processing A-glucosidase I) | Hs.516120 | 4-12 Score = 24.0 bits (49), Expect = 40 Identities = 7/9 (77%), Positives = 8/9 (88%) Query: 18 GARRRKAVP 26 G RRR+AVP Sbjct: 4 GERRRRAVP 12 | Not associated with cancer |

TABLE 6B-continued

| | | | | | | |
|---|---|---|---|---|---|---|
| 2D7 | gi|34882281|ref| XM_236768.2|, *Rattus norvegicus* hypothetical LOC316116 (LOC316116), mRNA | LRGTSGVQPPEIEQ (SEQ ID NO: 59) | 14 AA | gi|32172435|sp|P46934| NED4_HUMAN, Ubiquitin-protein ligase Nedd-4 | Hs.1565 | 514-520 Score = 22.7 bits (46), Expect = 70 Identities = 6/7 (85%), Positives = 6/7 (85%), Query: 8 QPPEIEQ 14 QP EIEQ Sbjct: 514 QPSEIEQ 520 | RING protein Trim32 associated with skin carcinogenesis has E3-ubiquitin ligase properties |
| 2D12 | gi|34783327|gb| BC022049.2|, *Homo sapiens* cDNA clone IMAGE: 4291567, partial cds | ILHLH (SEQ ID NO: 60) | 5 AA | gi|128616|sp|P23975| S6A2_HUMAN, Sodium-dependent noradrenaline transporter (Norepinephrine transporter) (NET) | Hs.78036 | 218-222 Score = 17.6 bits (34), Expect = 2425 Identities = 4/5 (80%), Positives = 5/5 (100%) Query: 1 ILHLH 5 + LHLH Sbjct: 218 VLHLH 222 | NET is involved in neurotransmitter removal from neuronal synapses |
| 2E7 | gi|6330364|dbj| AB033020.1|, *Homo sapiens* mRNA for KIAA1194 protein | VLSALPEKNCNTVPFQPP EDLRYQHCSSRFLE (SEQ ID NO: 61) | 32 AA | gi|34395825|sp|Q9H106| PTL2_HUMAN Protein tyrosine phosphatase non-receptor type substrate 1-like 2 precursor | Hs.339789 | 167-174 Score = 24.4 bits (50), Expect = 21 Identities = 7/8 (87%), Positives = 8/8 (100%) Query: 2 LSALPEKN 9 LSALPE+N Sbjct: 167 LSALPERN 174 | Protein-tyrosine phosphatase (SAP-1) is overexpressed in gastrointestinal cancer |
| 2G10 | gi|16307467|gb| BC010282.1|, *Homo sapiens* leucine-rich PPR-motif containing, mRNA | WGFNERDRLSSILQQRC VTL (SEQ ID NO: 62) | 20 AA | gi|13638201|sp|P41214| LIGA_HUMAN, Ligatin (Hepatocellular carcinoma-associated antigen 56) | Hs.274151 | 523-528 Score = 24.0 bits (49), Expect = 29 Identities = 6/6 (100%), Positives = 6/6 (100%) Query: 12 ILQQRC 17 ILQQRC Sbjct: 523 ILQQRC 528 | CD15 and CD50 antigens are both overexpressed in hepatocarcinoma. |
| 2G11 | gi|7329921|emb| AL117379.14| HSJ563E14, Human DNA sequence from clone RP4-563E14 on chromosome 20 Contains the 5′ end of the DATF1 gene encoding the death associated transcription factor 1, the 5′ end of a novel gene, ESTs, STSs, GSSs and four CpG islands, complete sequence. | VVSGFFSTFSL (SEQ ID NO: 63) | 11 AA | gi|1705762|sp|P13569| CFTR_HUMAN, Cystic fibrosis transmembrane conductance regulator (CFTR) | Hs.521149 | 429-435 Score = 21.8 bits (44), Expect = 128 Identities = 6/7 (85%), Positives = 6/7 (85%) Query: 5 FFSTFSL 11 FFS FSL Sbjct: 429 FFSNFSL 435 | Mutation of CFTR is observed in Cystic Fibrosis |

US 8,614,169 B2

TABLE 6B-continued

| | | | | | | |
|---|---|---|---|---|---|---|
| 2H8 | gi\|5714635\|gb\|AF159295.1\| AF159295, *Homo sapiens* serine/threonine protein kinase Kp78 splice variant CTAK75a mRNA | LTRPGHGQD (SEQ ID NO: 64) | 9 AA | gi\|2499758\|sp\|Q92729\| PTPU_HUMAN, Receptor-type protein-tyrosine phosphatase U precursor (R-PTP-U)(Protein-tyrosine phosphatase J) (PTP-J) (Pancreatic carcinoma phosphatase 2) PCP-2 | Hs.19718 | 355-361 Score = 19.3 bits (38), Expect = 748 Identities = 6/7 (85%), Positives = 6/7 (85%) Query: 1 LTRPGHG 7 LTRPG G Sbjct: 355 LTRPGDG 361 | A potential role of PCP-2 in cell-cell recognition and adhesion is supported by its co-localization with cell adhesion molecules, such as catenin and E-cadherin, at sites of cell-cell contact. |
| 4C5 | gi\|19683998\|gb\|BC025957.1\| *Homo sapiens* coated vesicle membrane protein, mRNA | LYINEMKSKKL (SEQ ID NO: 65) | 11 AA | gi\|4172716\|sp\|P33176\| KINH_HUMAN, Kinesin heavy chain (Ubiquitous kinesin heavy chain) (UKHC) | Hs.512922 | 592-599 Score = 22.3 bits (45), Expect = 95 Identities = 6/8 (75%), Positives = 8/8 (100%) Query: 1 LYINEMKS 8 LYI++ MKS Sbjct: 592 LYISKMKS 599 | Kinesin-1 links neurofibromin and merlin in a common cellular pathway of neurofibromatosis |
| 4H6 | gi\|22773353\|gb\|AC007998.10\|, *Homo sapiens* chromosome 18, clone RP11-322E11, complete sequence | LPQCPSRGSL (SEQ ID NO: 66) | 10 AA | gi\|1352515\|sp\|P48745\| NOV_HUMAN, NOV protein homolog precursor (NovH) (Nephroblastoma overexpressed gene protein homolog) | Hs.235935 | 37-42 Score = 20.2 bits (40), Expect = 414 Identities = 5/6 (83%), Positives = 5/6 (83%) Query: 2 PQCPSR 7 PQCP R Sbjct: 37 PQCPGR 42 | Altered Expression of novH is associated with human adrenocortical tumorigenesis |
| 5A2 | gi\|40788180\|emb\|AJ58382l.2\|, *Homo sapiens* mRNA for ubiquitin specific proteinase 40 (USP40 gene) | PGWDCRLPEAESCRFLL SSRGED (SEQ ID NO: 67) | 23 AA | gi\|21759008\|sp\|Q96CA5\| BIR7_HUMAN, Baculoviral IAP repeat-containing protein 7 (Kidney inhibitor of apoptosis protein) (KIAP) (Melanoma inhibitor of apoptosis protein) (ML-IAP) (Livin) | Hs.256126 | 150-159 Score = 22.7 bits (46), Expect = 68 Identities = 7/10 (70%), Positives = 9/10 (90%) Query: 12 SCRFLLSSRG 21 SC + FLL S + G Sbjct: 150 SCQFLLRSKG 159 | ML-IAP, a novel inhibitor of apoptosis, is preferentially expressed in human melanomas |
| 5A7 | gi\|16508181\|emb\|AL138765.18\|, Human DNA sequence from clone RP11-34F5 on chromosome 10, complete sequence | KKMRTKM (SEQ ID NO: 68) | 7 AA | gi\|30580423\|sp\|Q8IX29\| FX16_HUMAN, F-box only protein 16 | Hs.511876 | 14-19 Score = 20.6 bits (41), Expect = 310 Identities = 5/6 (83%), Positives = 6/6 (100%) Query: 2 KMRTKM 7 KM+TKM Sbjct: 14 KMQTKM 19 | A high expression level of F-box protein, Skp2 is observed in diffuse large cell B lymphoma. |
| 5B9 | gi\|27469381\|gb\|BC042411.1\|, *Mus musculus*, clone IMAGE: 4014861, mRNA | QIDSSFSIPWVVHGRS (SEQ ID NO: 69) | 17 AA | gi\|126885\|sp\|P08235\| MCR_HUMAN, Mineralocorticoid receptor (MR) | Hs.331409 | 420-426 Score = 22.3 bits (45), Expect = 93 Identities = 6/7 (85%), Positives = 7/7 (100%) | Glucocorticoid and mineralocorticoid cross-talk with progesterone |

TABLE 6B-continued

| | | | | | |
|---|---|---|---|---|---|
| 5B12 | gi\|34996477\|tpg\|BK001418.1\|, TPA: Homo sapiens metastasis associated in lung adenocarcinoma transcript 1 long isoform, transcribed non-coding RNA, complete sequence | GGRRSLRKPQISFFLFER (SEQ ID NO: 70) | | | Query: 3 DSSFSIP 9 DSSFS + P Sbjct: 420 DSSFSVP 426 |
| | | | gi\|34223735\|sp\|Q08462\| CYA2_HUMAN, Adenylate cyclase, type II (ATP pyrophosphate-lyase) (Adenylyl cyclase) | Hs.414591 | 136-142 Score = 24.4 bits (50), Expect = 21 Identities = 6/7 (85%), Positives = 7/7 (100%) Query: 10 QISFFLF 16 Q + SFFLF Sbjct: 136 QVSFFLF 142 | In human Y-79 retinoblastoma cells, corticotropin-releasing hormone (CRH) stimulates adenylyl cyclase activity and increases cyclic AMP accumulation |
| 5D6 | gi\|16741726\|gb\|BC016660.1\|, Homo sapiens heat shock 70 kDa protein 8, transcript variant 1, mRNA | GIRVEPPTRTIS (SEQ ID NO: 71) | gi\|6226869\|sp\|P34932\| HS74_HUMAN, HEAT SHOCK 70 KDA PROTEIN 4 (HEAT SHOCK 70-RELATED PROTEIN APG-2)(HSP70RY) | Hs.90093 | 316-328 Score = 21.0 bits (42), Expect = 229 Identities = 6/9 (66%), Positives = 8/9 (88%) Query: 3 RVEPPTRTI 11 RVEPP R++ Sbjct: 316 RVEPPLRSV 324 | Expression of HSP70 is observed in human hepatocellular carcinoma |
| 5E3 | gi\|40849693\|gb\|AY495321.1\|, Homo sapiens isolate V1-16 mitochondrion, complete genome | RNRYSTARER (SEQ ID NO: 72) | gi\|2501463\|sp\|Q93008\| FAFX_HUMAN, Probable ubiquitin carboxyl-terminal hydrolase FAF-X | Hs.77578 | 1356-1361 Score = 21.4 bits (43), Expect = 172 Identities = 6/6 (100%), Positives = 6/6 (100%) Query: 5 STARER 10 STARER Sbjct: 1356 STARER 1361 | Oxidative Modifications and Down-regulation of Ubiquitin Carboxyl-terminal Hydrolase L1 Associated with Idiopathic Parkinson's and Alzheimer's Diseases. |
| 5H8 | gi\|13273214\|gb\|AAK17820\|, cytochrome c oxidase subunit I [Homo sapiens] | GKRHIGGTDY (SEQ ID NO: 73) | gi\|41713338\|sp\|Q8N690\| D119_HUMAN Beta-defensin 119 precursor (Beta-defensin 19) (DEFB-19) | Corresponding Unigene number is not found | 21-25 Score = 19.3 bits (38), Expect = 550 Identities = 5/5 (100%), Positives = 5/5 (100%) Query: 1 GKRHI 5 GKRHI Sbjct: 21 GKRHI 25 | The expression of human beta-defensin genes in oral squamous cell carcinomas (SCCs) was demonstrated by in situ hybridization. |

(First row continuation description: receptor to induce focal adhesion and growth inhibition in breast cancer cells)

TABLE 6B-continued

| | | | | | |
|---|---|---|---|---|---|
| 5A4 | gi|17149463|gb| AC068228.8|, *Homo sapiens* chromosome 8, clone RP11-539E17, complete sequence | VVSQLTAEMRLE (SEQ ID NO: 74) | 12 AA | gi|129825|sp|P05164| PERM_HUMAN, Myeloperoxidase precursor (MPO) | Hs.458272 | 23-29 Score = 22.7 bits (46), Expect = 71 Identities = 6/7 (85%), Positives = 7/7 (100%) Query: 5 LTAEMRL 11 LTAEM+L Sbjct: 23 LTAEMKL 29 | Myeloperoxidase immunoreactivity is observed in adult acute lymphoblastic leukemia |
| 5E7 | gi|4885510|ref| NM_005381.1|, *Homo sapiens* nucleolin (NCL), mRNA | RACQRSTWKTKEGNGQ TESSS (SEQ ID NO: 75) | 21 AA | gi|25453064|sp|Q9UPT6| JIP3_HUMAN, C-jun-amino-terminal kinase interacting protein 3 (JNK-interacting protein 3) (JIP-3) | Hs.514335 | 192-199 Score = 23.1 bits (47), Expect = 51 Identities = 7/8 (87%), Positives = 7/8 (87%) Query: 13 GNGQTESS 20 GN QTESS Sbjct: 192 GNSQTESS 199 | JNK interacting protein (JIP) can inhibit JNK signaling pathway in NPC cell (nasopharyngeal carcinoma) |

TABLE 7A

Selection of most significant clones from Group 1 dataset

26 Clones ordered according to binding with the 16 patients in Group 1. None of the 25 healthy women's sera (belonging to Group 1) contained IgGs that any of these clones. Clones are shown in rows. Patients numbers are shown in the columns. The last column, TP, Total number of patients whose serum IgGs bound to each phage clone.

| | Mec1 | Mec2 | Mec16 | Mec35 Δ | TB01-108Δ | 400162 | 40015 | OVC015 | OVC035 | OVC007 | OVC005 | NW 4679 | NW 4283 | OVC019 | OVC087 | OVC045 | TP |
|---|---|---|---|---|---|---|---|---|---|---|---|---|---|---|---|---|---|
| 2G2 (SEQ ID NO: 41) | | ■ | | ■ | | ■ | ■ | ■ | | ■ | ■ | | | ■ | ■ | | 8 |
| 2G4 (SEQ ID NO: 14) | ■ | | | | ■ | ■ | ■ | ■ | | | ■ | | | ■ | ■ | | 8 |
| 2H9 (SEQ ID NO: 22) | | | ■ | | | | ■ | ■ | ■ | | ■ | | | ■ | ■ | | 7 |
| 2B4 (SEQ ID NO: 12) | | | ■ | | | ■ | | ■ | ■ | | ■ | | | ■ | | | 6 |
| 4A3 (SEQ ID NO: 35) | | | | | ■ | | ■ | ■ | ■ | ■ | | | | | | | 5 |
| 5A3 (SEQ ID NO: 26) | | ■ | | | | ■ | ■ | | | | ■ | | | ■ | | | 5 |
| 3B12 (SEQ ID NO: 23) | ■ | ■ | | | | | | | | | | | | ■ | ■ | | 4 |
| 2H5 (SEQ ID NO: 51) | | ■ | | | | | | ■ | | | ■ | | | ■ | | | 4 |
| 2E12 (SEQ ID NO: 43) | | ■ | ■ | | | | | ■ | | | | | | ■ | | | 4 |
| 2E10 (SEQ ID NO: 37) | | ■ | ■ | | | | | | | | | | ■ | | | | 3 |
| 2C7 (SEQ ID NO: 33) | | | ■ | | | | | | | | | ■ | | ■ | | | 3 |
| 2F12 (SEQ ID NO: 52) | | ■ | | | | | ■ | | | | | | | ■ | | | 3 |
| 2E11 (SEQ ID NO: 30) | ■ | ■ | | | | | | | | | | | | ■ | | | 3 |
| 4H3 (SEQ ID NO: 18) | | | | ■ | | | | | | | | | ■ | | ■ | | 3 |
| 4A11 (SEQ ID NO: 17) | | | | | | | | | | ■ | ■ | | | | ■ | | 3 |
| 2A3 (SEQ ID NO: 27) | | | | | ■ | ■ | | | | | | | | | | | 2 |
| 3C11 (SEQ ID NO: 16) | | | | | | | | | | | | | ■ | ■ | | | 2 |
| 5G9 (SEQ ID NO: 31) | | | | | | | ■ | | | ■ | | | | | | | 2 |
| 4A4 (SEQ ID NO: 25) | | | | | | | | | | ■ | ■ | | | | | | 2 |
| 4B2 (SEQ ID NO: 45) | | | | ■ | | | | ■ | | | | | | | | | 2 |

TABLE 7A-continued

Selection of most significant clones from Group 1 dataset

26 Clones ordered according to binding with the 16 patients in Group 1. None of the 25 healthy women's sera (belonging to Group 1) contained IgGs that any of these clones. Clones are shown in rows. Patients numbers are shown in the columns. The last column, TP, Total number of patients whose serum IgGs bound to each phage clone.

| Clone | 1 | 2 | 3 | 4 | 5 | 6 | 7 | 8 | 9 | 10 | 11 | 12 | 13 | 14 | 15 | 16 | TP |
|---|---|---|---|---|---|---|---|---|---|---|---|---|---|---|---|---|---|
| 5C12 (SEQ ID NO: 50) |  |  |  |  |  | ■ |  |  | ■ |  |  |  |  |  |  |  | 2 |
| 2C1 (SEQ ID NO: 40) |  | ■ |  |  |  |  |  |  |  |  |  |  |  |  |  |  | 1 |
| 5F9 (SEQ ID NO: 54) |  |  |  |  | ■ |  |  |  |  |  |  |  |  |  |  |  | 1 |
| 2F10 (SEQ ID NO: 49) |  |  |  |  | ■ |  |  |  |  |  |  |  |  |  |  |  | 1 |
| 3A9 (SEQ ID NO: 15) |  |  |  |  |  |  |  |  |  |  |  |  | ■ |  |  |  | 1 |
| 3C8 (SEQ ID NO: 47) |  |  |  |  |  |  |  |  |  |  |  |  |  | ■ |  |  | 1 |

Δ: Serum Dilution 1:3000; all others were analyzed at a serum dilution of 1:10000.

TABLE 7B

Binding of 26 clones with 16 Patients on a new dataset (Group 2)

The rows represent the 26 clones and the columns represent the 16 patients. As shown in this table, sera from 16 out of the 16 patients in Group 2 contained IgGs that bound at least one clone. None of IgGs in sera 12 healthy women interacted with any of these 26 clones.

| Clone | Mec20 | Mec23 | Mec37 Δ | TB01-108Δ | 42501 | 40036 | 42780 | B755 ▲ | OVC075 | OVC063 | NW 4387 | NW 4555 | OVC078 | OVC070 | OVC049 | OVC079 | TP |
|---|---|---|---|---|---|---|---|---|---|---|---|---|---|---|---|---|---|
| 2G2 (SEQ ID NO: 41) | ■ |  |  | ■ |  |  | ■ | ■ |  |  |  |  | ■ | ■ |  |  | 5 |
| 2G4 (SEQ ID NO: 14) | ■ |  |  |  |  | ■ |  |  |  |  |  |  | ■ | ■ |  |  | 4 |
| 2H9 (SEQ ID NO: 22) | ■ |  |  | ■ |  |  | ■ | ■ |  |  |  |  | ■ | ■ |  |  | 6 |
| 2B4 (SEQ ID NO: 12) |  | ■ | ■ |  | ■ | ■ | ■ |  |  |  |  |  | ■ |  |  |  | 6 |
| 4A3 (SEQ ID NO: 35) |  |  |  |  |  |  |  |  | ■ |  |  |  | ■ | ■ |  |  | 4 |
| 5A3 (SEQ ID NO: 26) |  | ■ | ■ | ■ |  |  |  |  |  |  |  |  |  |  |  |  | 3 |
| 3B12 (SEQ ID NO: 23) |  | ■ |  |  |  |  | ■ |  | ■ | ■ |  |  | ■ |  |  |  | 5 |
| 2H5 (SEQ ID NO: 51) | ■ |  |  |  |  | ■ |  | ■ |  | ■ |  |  |  |  |  |  | 4 |
| 2E12 (SEQ ID NO: 43) | ■ |  |  |  |  | ■ |  | ■ |  |  |  |  |  |  |  |  | 3 |

TABLE 7B-continued

Binding of 26 clones with 16 Patients on a new dataset (Group 2)
The rows represent the 26 clones and the columns represent the 16 patients. As shown in this table, sera from 16 out of
the 16 patients in Group 2 contained IgGs that bound at least one clone. None of IgGs in sera 12 healthy women
interacted with any of these 26 clones.

| | | | | | | | | | | | | | | | | |
|---|---|---|---|---|---|---|---|---|---|---|---|---|---|---|---|---|
| 2E10 (SEQ ID NO: 37) | ■ | | | | ■ | | | | | ■ | | | | ■ | ■ | 5 |
| 2C7 (SEQ ID NO: 33) | ■ | | | | ■ | | | | | | | | | ■ | | 4 |
| 2F12 (SEQ ID NO: 52) | | | ■ | | ■ | ■ | | | | | | | | | | 4 |
| 2E11 (SEQ ID NO: 30) | | | ■ | | | ■ | | | | | | | | | | 3 |
| 4H3 (SEQ ID NO: 18) | ■ | | | | | | | ■ | | | | | | ■ | | 3 |
| 4A11 (SEQ ID NO: 17) | | | | | | | | | | | ■ | ■ | | | | 2 |
| 2A3 (SEQ ID NO: 27) | | | ■ | | ■ | ■ | | | | | ■ | ■ | | | | 6 |
| 3C11 (SEQ ID NO: 16) | | | | | | | | | | | ■ | ■ | ■ | | | 3 |
| 5G9 (SEQ ID NO: 31) | | | | ■ | | | | | ■ | | ■ | | | | | 3 |
| 4A4 (SEQ ID NO: 25) | | | | | | | | | | | ■ | ■ | | | | 2 |
| 4B2 (SEQ ID NO: 45) | | | | | | | | | ■ | | ■ | | | | | 2 |
| 5C12 (SEQ ID NO: 50) | | | ■ | | | | | | | | | | | ■ | | 2 |
| 2C1 (SEQ ID NO: 40) | | ■ | | | | | ■ | | | | | | | | | 4 |
| 5F9 (SEQ ID NO: 54) | | | | | ■ | | | | | | | | | ■ | | 3 |
| 2F10 (SEQ ID NO: 49) | | | | | | | | | ■ | | | ■ | | | | 2 |
| 3A9 (SEQ ID NO: 15) | | | | | | | | | | | | ■ | ■ | | | 2 |
| 3C8 (SEQ ID NO: 47) | | | | | | | | | | | | ■ | ■ | | | 2 |

Δ: Serum Dilution 1:3000; ▲: Serum Dilution 1:30000; all others were analyzed at a serum dilution of 1:10000.

REFERENCES

1. Alizadeh A A, et al. Distinct types of diffuse large B-cell lymphoma identified by gene expression profiling. Nature 403:503-511, (2000).
2. An, A, et al. A learning system for more accurate classifications. Lecture Notes in Artificial Intelligence, Vancouver. 1418:426-441, (1998).
3. Aunoble B, et al. Major oncogenes and tumor suppressor genes involved in epithelial ovarian cancer. Int J Oncol 16:567-76, (2000).
4. Baron A T, et al. Serum sErbB1 and Epidermal Growth Factor Levels As Tumor Biomarkers in Women with Stage III or IV Epithelial Ovarian Cancer Epidemiology. Biomarkers & Prevention 8:129-137, 1999.
5. Bauer R, et al. Cloning and characterization of the *Drosophila* homologue of the AP-2 transcription factor. Oncogene 17:1911-1922 (1998).
6. Bast R C, et al. Reactivity of a monoclonal antibody with human ovarian carcinoma. J. Clin Invest 68:1331-1337 (1981).
7. Bast R C et al. A radioimmunoassay using a monoclonal antibody to monitor the course of epithelial ovarian cancer. N Engl J Med 309: 883-887 (1983).
8. Berek, J S et al. Serum interleukins-6 levels correlate with disease status in patients with epithelial ovarian cancer. Am J Obstet Gynecol 164: 1038-1043 (1991).
9. Biftner, M et al. Molecular Classification of Cutaneous Malignant Melanoma by Gene Expression Profiling. Nature 406:536-540 (2000).
10. Blake C, et al. UCI respitory of machine learning databases (1998).
11. Boyd J, et al. Molecular genetic and clinical implications [Review]. Gynecol Oncol 64:196-206 (1997).
12. Breiman L, et al. Classification and regression trees, Wadsworth and Brooks (1984).
13. Buettner R, et al. An alternatively spliced form of AP-2 encodes a negative regulator of transcriptional activation by AP-2. Mol. Cell Biol 13:4174-4185 (1993).
14. Chiao P J, et al. Elevated expression of the human ribosomal S2 gene in human tumors. Molecular Carcinogenesis 5:219-231 (1992).
15. Clark P, et al. The CN2 induction algorithm. Machine Learning 3:261-283 (1989).
16. Coleman M P, et al. Trends in cancer incidence and mortality. Lyon, France: IARC Scientific Publications 121: 477-498 (1993).
17. Deyo J, et al. A novel protein expressed at high cell density but not during growth arrest. DNA and Cell Biol 17:437-447 (1998).
18. Draghici S. The Constraint Based Decomposition, accepted for publication in Neural Networks, to appear (2001).
19. Einhorn, N. et al. Prospective evaluation of serum CA 125 levels for early detection of ovarian cancer. Obstet Gynecol 80:14-18 (1992).
20. Golub T R, et al. Molecular classification of cancer: class discovery and class prediction by gene expression monitoring. Science 286:531-537 (1999).
21. Gotlieb W H, et al. Presence of interleukins in the ascites of patients with ovarian and other intrabdominal cancers. Cytokine 4:385-390 (1992).
22. Greenlee R T, et al. Cancer Statistics. CA Cancer J Clin 50:7-33 (2000).
23. Heath, S. et al. Induction of oblique decision tree. In IJCAI-93. Washington, D.C. (1993).
24. Hogdall E V, et al. Predictive values of serum tumour markers tetranectin, OVX1, CASA and CA125 in patients with a pelvic mass. Int J serum tumour markers tectranectin, OVX1, CASA and CA125 in patients with a pelvic mass. Int J Cancer 89:519-523 (2000).
25. Holschneider C H, et al. Ovarian cancer: epidemiology, biology, and prognostic factors. Semin Surg Oncol 1:3-10 (2000).
26. Houts T M: Improved 2-Color Normalization For Microarray Analyses Employing Cyanine Dyes, CAMDA (2000). Critical Assessment of Techniques for Microarray Data Mining. Duke University Medical Center, December 18-19 (2000).
27. Jacobs IJ, et al. Potential screening tests for ovarian cancer, in Sharp F, Mason W P, Leake R E (eds). Ovarian Cancer. London, Chapman and Hall Medical, 197-205 (1997).
28. Jacobs, I. Et al. Multimodal approach to screening for ovarian cancer. Lancet 1268-271 (1988).
29. Jacobs I, et al. The CA 125 tumor-associated antigen: a review of the literature. Hum Reprod 4:1-12 (1989).
30. Kacinski B M et al. Macrophage colony-stimulating factor is produced by human ovarian and endometrial adenocarcinoma-derived cell lines and is present at abnormally high levels in the plasma of ovarian carcinoma patients with active disease. Cancer Cells 7:333-337 (1989).
31. Kerr, Martin, Churchill. Analysis of variance for gene expression microarray data. Journal of Computational Biology (2000).
32. Kim, S Y et al. Coordinate Control of Growth and Cytokeratin 13 Expression by Retinoic Acid. Molecular Carcinogenesis 16:6-11 (1996).
33. Kohonen T. Learning vector quantization. Neural Networks, 1 (suppl.1):303 (1988).
34. Kohonen T. Learning vector quantization. In the handbook of brain theory and neural networks pp. 537-540. Cambridge Mass.: MIT press (1995).
35. MacBeath G. et al. Printing proteins as microarrays for high-throughput function determination. Science 289:1760-3 (2000).
36. Murthy K. On growing better decision trees from data. Unpublished doctoral dissertation. John Hopkins University (1995).
37. Musavi M. et al. On the training of radial basis functions classifiers. Neural Networks 5:595-603 (1992).
38. Patsner B. et al. Comparison of serum CA 125 and lipid associated sialic acid (LASA-P) in monitoring patients with invasive ovarian adenocarcinoma. Gynecol Oncol 30(1): 98-103 (1988).
39. Peng Y S, et al. ARHI is the center of allelic deletion on chromosome Ip31 in ovarian and breast cancers. Int J Cancer 86:690-4 (2000).
40. Precup D, et al. Classification using $/Phi$-machines and constructive function approximation. In Proc. 15th International Conf. On Machine Learning, pages 439-444. Morgan Kaufmann, San Francisco, Calif. (1998),
41. Poggio T, et al. Networks for approximation and learning. Proceedings of IEEE 78(9):1481-149 (1990).
42. Quinlan J R: C4.5: Programs for machine learning, Morgan-Kaufmann (1993).
43. Rumelhart, D E, et al. Learning internal representations by error backpropagation. Parallel Distributed Processing: Explorations in the Microstructures of Cognition, MIT Press/ Bradford Books (1986).
44. Schwartz P E, et al. Circulating tumor markers in the monitoring of gynecologic malignancies. Cancer 60:353-361 (1987).

45. Schmittgen T D et al. Quantitative reverse transcription-polymerase chain reaction to study mRNA decay: comparison of endpoint and real-time methods. Anal Biochem, 285:194-204 (2000).

46. Sonoda K, Nakashima M, Kaku T, Kamura T, Nakano H, Watanabe T. A novel tumor-associated antigen expressed in human uterine and ovarian carcinomas. Cancer 1996 77:1501-9, 47. Nakashima M, Sonoda K, Watanabe T. Inhibition of cell growth and induction of apoptotic cell death by the human tumor-associated antigen RCAS1. Nat. Med. 1999 5:938-42.

48. Lindstrom M S, Klangby U, Wiman K G. p14ARF homozygous deletion or MDM2 overexpression in Burkitt lymphoma lines carrying wild type p53. Oncogene. 20(17): 2171-7, 2001.

What is claimed is:

1. A diagnostic tool for detecting the presence of Stage II-IV ovarian cancer, said tool comprising: detection means for detecting a presence of at least one marker, wherein the at least one marker is at least one T7 phage display antigen clone displaying a peptide selected from the group of peptides consisting of SEQ ID NOS: 55-75, wherein the peptide sequence is in-frame with the T7 10B gene product, indicative of the presence of Stage II-IV ovarian cancer; and analyzing means operatively connected to said detection means, said analyzing means for determining fluctuations in amount of the at least one marker present in said detection means, whereby fluctuations correlate to the presence of Stage II-IV ovarian cancer.

* * * * *

SEQUENCE LISTING

```
<160> NUMBER OF SEQ ID NOS: 197

<210> SEQ ID NO 1
<211> LENGTH: 20
<212> TYPE: DNA
<213> ORGANISM: Artificial Sequence
<220> FEATURE:
<223> OTHER INFORMATION: T7 coat protein forward primer

<400> SEQUENCE: 1
tcttcgccca gaagctgcag                                                   20

<210> SEQ ID NO 2
<211> LENGTH: 22
<212> TYPE: DNA
<213> ORGANISM: Artificial Sequence
<220> FEATURE:
<223> OTHER INFORMATION: T7 coat protein reverse primer

<400> SEQUENCE: 2
cctcctttca gcaaaaaacc cc                                                22

<210> SEQ ID NO 3
<211> LENGTH: 14
<212> TYPE: DNA
<213> ORGANISM: Artificial Sequence
<220> FEATURE:
<223> OTHER INFORMATION: EcoRI/HindIII Directional Linker

<400> SEQUENCE: 3
gcttgaattc aagc                                                         14

<210> SEQ ID NO 4
<211> LENGTH: 6
<212> TYPE: DNA
<213> ORGANISM: Artificial Sequence
<220> FEATURE:
<223> OTHER INFORMATION: HindIII site

<400> SEQUENCE: 4 aagctt                                                                   6

<210> SEQ ID NO 5
<211> LENGTH: 8
<212> TYPE: DNA
<213> ORGANISM: Artificial Sequence
<220> FEATURE:
<223> OTHER INFORMATION: HindIII random primer
<220> FEATURE:
<221> NAME/KEY: misc_feature
<222> LOCATION: (3)..(8)
<223> OTHER INFORMATION: n is a, c, g, or t

<400> SEQUENCE: 5 ttnnnnnn                                                                 8
```

-continued

```
<210> SEQ ID NO 6
<211> LENGTH: 17
<212> TYPE: DNA
<213> ORGANISM: Artificial Sequence
<220> FEATURE:
<223> OTHER INFORMATION: T7 forward primer

<400> SEQUENCE: 6
tcttcgccca gaagcag                                              17

<210> SEQ ID NO 7
<211> LENGTH: 20
<212> TYPE: DNA
<213> ORGANISM: Artificial Sequence
<220> FEATURE:
<223> OTHER INFORMATION: T7 reverse primer

<400> SEQUENCE: 7
cctccttcag caaaaacccc                                           20

<210> SEQ ID NO 8
<211> LENGTH: 21
<212> TYPE: DNA
<213> ORGANISM: Artificial Sequence
<220> FEATURE:
<223> OTHER INFORMATION: forward PCR primer

<400> SEQUENCE: 8
gttctatccg caacgttatg g                                         21

<210> SEQ ID NO 9
<211> LENGTH: 22
<212> TYPE: DNA
<213> ORGANISM: Artificial Sequence
<220> FEATURE:
<223> OTHER INFORMATION: reverse PCR primer

<400> SEQUENCE: 9
ggaggaaagt cgttttttgg gg                                        22

<210> SEQ ID NO 10
<211> LENGTH: 20
<212> TYPE: DNA
<213> ORGANISM: Artificial Sequence
<220> FEATURE:
<223> OTHER INFORMATION: forward Sequencing primer

<400> SEQUENCE: 10
tgctaaggac aacgttatcg                                           20

<210> SEQ ID NO 11
<211> LENGTH: 25
<212> TYPE: PRT
<213> ORGANISM: Homo sapiens

<400> SEQUENCE: 11

Ala Ala Trp Gln Ala Glu Glu Val Leu Arg Gln Gln Lys Leu Ala Asp
1               5                   10                  15

Arg Glu Lys Arg Ala Ala Glu Gln Gln
            20                  25

<210> SEQ ID NO 12
<211> LENGTH: 212
<212> TYPE: PRT
<213> ORGANISM: Homo sapiens
```

```
<220> FEATURE:
<221> NAME/KEY: MISC_FEATURE
<222> LOCATION: (23)..(23)
<223> OTHER INFORMATION: Xaa can be any naturally occurring amino acid

<400> SEQUENCE: 12

Glu Lys Gly Gly Gln Glu Lys Gln Gly Glu Val Ile Val Ser Ile Glu
1               5                   10                  15

Glu Lys Pro Lys Glu Val Xaa Glu Glu Gln Pro Val Val Thr Leu Glu
            20                  25                  30

Lys Gln Gly Thr Ala Val Glu Val Ala Glu Ser Leu Asp Pro Thr
        35                  40                  45

Val Lys Pro Val Asp Val Gly Gly Asp Glu Pro Glu Glu Lys Val Val
    50                  55                  60

Thr Ser Glu Asn Glu Ala Gly Lys Ala Val Leu Glu Gln Leu Val Gly
65                  70                  75                  80

Gln Glu Val Pro Pro Ala Glu Glu Ser Pro Glu Val Thr Thr Glu Ala
                85                  90                  95

Ala Glu Ala Ser Ala Val Glu Ala Gly Ser Glu Val Ser Glu Lys Pro
            100                 105                 110

Gly Gln Glu Ala Pro Val Leu Pro Lys Asp Gly Ala Val Asn Gly Pro
        115                 120                 125

Ser Val Val Gly Asp Gln Thr Pro Ile Glu Pro Gln Thr Ser Ile Glu
    130                 135                 140

Arg Leu Thr Glu Thr Lys Asp Gly Ser Gly Leu Glu Glu Lys Val Arg
145                 150                 155                 160

Ala Lys Leu Val Pro Ser Gln Glu Glu Thr Lys Leu Ser Val Glu Glu
                165                 170                 175

Ser Glu Ala Ala Gly Asp Gly Val Asp Thr Lys Val Ala Gln Gly Ala
            180                 185                 190

Thr Glu Lys Ser Pro Glu Asp Lys Val Gln Ile Ala Ala Asn Glu Glu
        195                 200                 205

Thr Gln Glu Arg
    210

<210> SEQ ID NO 13
<211> LENGTH: 15
<212> TYPE: PRT
<213> ORGANISM: Homo sapiens

<400> SEQUENCE: 13

Glu Lys Gly Gly Gln Glu Lys Gln Gly Glu Val Ile Val Ser Ile
1               5                   10                  15

<210> SEQ ID NO 14
<211> LENGTH: 148
<212> TYPE: PRT
<213> ORGANISM: Homo sapiens

<400> SEQUENCE: 14

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60
```

```
Thr Gly Lys Lys Tyr Glu Asp Ile Cys Pro Ser Thr His Asn Met Asp
 65                  70                  75                  80

Val Pro Asn Ile Lys Arg Asn Asp Phe Gln Leu Ile Gly Ile Gln Asp
                 85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu His Lys Phe Asp
            115                 120                 125

Cys Gly Glu Gln Ile Leu Ile Thr Val Leu Ser Ala Met Thr Glu Glu
            130                 135                 140

Ala Leu Val Ala
145

<210> SEQ ID NO 15
<211> LENGTH: 25
<212> TYPE: PRT
<213> ORGANISM: Homo sapiens

<400> SEQUENCE: 15

Gln Lys Thr Gly Gly Ala Asp Gln Ser Leu Gln Gln Gly Glu Gly Ser
 1               5                  10                  15

Lys Lys Gly Lys Gly Lys Lys Lys
            20                  25

<210> SEQ ID NO 16
<211> LENGTH: 68
<212> TYPE: PRT
<213> ORGANISM: Homo sapiens

<400> SEQUENCE: 16

Ala Leu Gln Ala Lys Ser Asp Glu Lys Ala Ala Val Ala Gly Lys Lys
 1               5                  10                  15

Pro Val Val Gly Lys Lys Gly Lys Lys Ala Ala Val Gly Val Lys Lys
            20                  25                  30

Gln Lys Lys Pro Leu Val Gly Lys Lys Ala Ala Ala Thr Lys Lys Pro
            35                  40                  45

Ser Pro Glu Lys Lys Pro Ala Glu Asn Lys Pro Thr Thr Glu Asp Asn
 50                  55                  60

Lys Pro Ala Ala
 65

<210> SEQ ID NO 17
<211> LENGTH: 86
<212> TYPE: PRT
<213> ORGANISM: Homo sapiens

<400> SEQUENCE: 17

Gln Gln Gln Gln Gln Gln His Gln Ala Ser Ser Asn Ser Gly Ser
 1               5                  10                  15

Glu Glu Asp Ser Ser Ser Glu Asp Ser Asp Ser Ser Glu
            20                  25                  30

Val Lys Arg Lys Lys His Lys Asp Glu Trp Gln Met Ser Gly Ser
            35                  40                  45

Gly Ser Pro Ser Gln Ser Gly Asp Ser Glu Ser Glu Glu Glu Arg
 50                  55                  60

Glu Lys Ser Ser Cys Asp Glu Thr Glu Ser Asp Tyr Glu Pro Lys Asn
 65                  70                  75                  80

Lys Val Lys Ser Arg Lys
            85
```

```
<210> SEQ ID NO 18
<211> LENGTH: 101
<212> TYPE: PRT
<213> ORGANISM: Homo sapiens
<220> FEATURE:
<221> NAME/KEY: MISC_FEATURE
<222> LOCATION: (80)..(100)
<223> OTHER INFORMATION: Xaa can be any naturally occurring amino acid

<400> SEQUENCE: 18

Pro Thr Lys Leu Pro Ser Ile Asn Lys Ser Lys Asp Arg Ala Ser Gln
 1               5                  10                  15

Gln Gln Gln Thr Asn Ser Ile Arg Asn Tyr Phe Gln Pro Ser Thr Lys
            20                  25                  30

Lys Arg Glu Arg Asp Glu Glu Asn Gln Glu Met Ser Cys Lys Ser
        35                  40                  45

Ala Arg Ile Glu Thr Ser Cys Ser Leu Leu Glu Gln Thr Gln Pro Ala
    50                  55                  60

Thr Pro Ser Leu Trp Lys Asn Lys Glu Gln His Leu Ser Glu Asn Xaa
65                  70                  75                  80

Pro Val Asp Thr Xaa Ser Xaa Xaa Asn Leu Phe Thr Gly Tyr Xaa Phe
                85                  90                  95

Arg Xaa Gly Xaa Glu
            100

<210> SEQ ID NO 19
<211> LENGTH: 118
<212> TYPE: PRT
<213> ORGANISM: Homo sapiens

<400> SEQUENCE: 19

Met Ala Asp Asp Leu Asp Phe Glu Thr Gly Asp Ala Gly Ala Ser Ala
 1               5                  10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Pro Leu Pro Glu Gly Asp
        115

<210> SEQ ID NO 20
<211> LENGTH: 121
<212> TYPE: PRT
<213> ORGANISM: Homo sapiens

<400> SEQUENCE: 20

Pro Lys Phe Lys Met Pro Asp Val His Phe Lys Ser Pro Gln Ile Ser
 1               5                  10                  15

Met Ser Asp Ile Asp Leu Asn Leu Lys Gly Pro Lys Ile Lys Gly Asp
            20                  25                  30
```

```
Met Asp Ile Ser Val Pro Lys Leu Glu Gly Asp Leu Lys Gly Pro Lys
         35                  40                  45

Val Asp Val Lys Gly Pro Lys Val Gly Ile Asp Thr Pro Asp Ile Asp
     50                  55                  60

Ile His Gly Pro Glu Gly Lys Leu Lys Gly Pro Lys Phe Lys Met Pro
65                  70                  75                  80

Asp Leu His Leu Lys Ala Pro Lys Ile Ser Met Pro Glu Val Asp Leu
                 85                  90                  95

Asn Leu Lys Gly Pro Lys Val Lys Gly Asp Met Asp Ile Ser Leu Pro
             100                 105                 110

Lys Val Glu Gly Asp Leu Lys Gly Pro
         115                 120

<210> SEQ ID NO 21
<211> LENGTH: 173
<212> TYPE: PRT
<213> ORGANISM: Homo sapiens
<220> FEATURE:
<221> NAME/KEY: misc_feature
<222> LOCATION: (127)..(173)
<223> OTHER INFORMATION: Xaa can be any naturally occurring amino acid

<400> SEQUENCE: 21

Gly Val Cys Ser Ser Lys Val Tyr Val Gly Lys Asn Thr Ser Glu Val
1               5                   10                  15

Lys Glu Asp Val Val Leu Gly Lys Ser Asn Gln Val Cys Gln Ser Ser
             20                  25                  30

Gly Asn His Leu Glu Asn Lys Val Thr His Gly Leu Val Thr Val Glu
         35                  40                  45

Gly Gln Leu Thr Ser Asp Glu Arg Gly Ala His Ile Met Asn Ser Thr
     50                  55                  60

Cys Ala Ala Met Pro Lys Leu His Glu Pro Tyr Ala Ser Ser Gln Cys
65                  70                  75                  80

Ile Ala Ser Pro Asn Phe Gly Thr Val Ser Gly Leu Lys Pro Ala Ser
                 85                  90                  95

Met Leu Glu Lys Asn Cys Ser Gln Thr Glu Leu Asn Lys Ser Tyr
             100                 105                 110

Asp Val Lys Asn Pro Ser Pro Leu Leu Met Gln Asn Gln Asn Xaa Arg
         115                 120                 125

Gln Gln Met Asp Thr Pro Met Val Ser Cys Gly Asn Glu Gln Phe Leu
     130                 135                 140

Asp Asn Ser Phe Glu Lys Xaa Lys Arg Xaa Leu Asp Leu Xaa Ile Asp
145                 150                 155                 160

Gly Xaa Gln Lys Xaa Xaa Cys Pro Xaa Val Xaa Xaa Xaa
                 165                 170

<210> SEQ ID NO 22
<211> LENGTH: 5
<212> TYPE: PRT
<213> ORGANISM: Homo sapiens

<400> SEQUENCE: 22

Glu Leu Leu Arg Thr
1               5

<210> SEQ ID NO 23
<211> LENGTH: 5
<212> TYPE: PRT
<213> ORGANISM: Homo sapiens
```

```
<400> SEQUENCE: 23

Gly Gln Thr Ser Met
1               5

<210> SEQ ID NO 24
<211> LENGTH: 5
<212> TYPE: PRT
<213> ORGANISM: Homo sapiens

<400> SEQUENCE: 24

Lys Lys Gly Pro Ile
1               5

<210> SEQ ID NO 25
<211> LENGTH: 6
<212> TYPE: PRT
<213> ORGANISM: Homo sapiens

<400> SEQUENCE: 25

Ala Lys Val Ile Met Arg
1               5

<210> SEQ ID NO 26
<211> LENGTH: 6
<212> TYPE: PRT
<213> ORGANISM: Homo sapiens

<400> SEQUENCE: 26

Tyr Ala Cys Leu Lys Asp
1               5

<210> SEQ ID NO 27
<211> LENGTH: 7
<212> TYPE: PRT
<213> ORGANISM: Homo sapiens

<400> SEQUENCE: 27

Gln Ile Leu Phe Met Asp Pro
1               5

<210> SEQ ID NO 28
<211> LENGTH: 8
<212> TYPE: PRT
<213> ORGANISM: Homo sapiens

<400> SEQUENCE: 28

Leu Asn Thr Val Asn Thr Leu Ile
1               5

<210> SEQ ID NO 29
<211> LENGTH: 8
<212> TYPE: PRT
<213> ORGANISM: Homo sapiens

<400> SEQUENCE: 29

Gly Asn Ser Ile Leu Leu Ile Ala
1               5

<210> SEQ ID NO 30
<211> LENGTH: 8
<212> TYPE: PRT
<213> ORGANISM: Homo sapiens

<400> SEQUENCE: 30

Trp Asp Leu Lys Ser Glu Tyr Ser
```

```
<210> SEQ ID NO 31
<211> LENGTH: 8
<212> TYPE: PRT
<213> ORGANISM: Homo sapiens

<400> SEQUENCE: 31

Pro Gly Cys Ser Thr Thr Leu Ser
1               5

<210> SEQ ID NO 32
<211> LENGTH: 8
<212> TYPE: PRT
<213> ORGANISM: Homo sapiens

<400> SEQUENCE: 32

Pro Arg Cys Ser Thr Thr Leu Ser
1               5

<210> SEQ ID NO 33
<211> LENGTH: 9
<212> TYPE: PRT
<213> ORGANISM: Homo sapiens

<400> SEQUENCE: 33

Gly Asp Arg Ser Gln Leu Trp Arg Lys
1               5

<210> SEQ ID NO 34
<211> LENGTH: 9
<212> TYPE: PRT
<213> ORGANISM: Homo sapiens

<400> SEQUENCE: 34

Lys Lys Gln Ser Ser Trp Tyr Gln Ile
1               5

<210> SEQ ID NO 35
<211> LENGTH: 9
<212> TYPE: PRT
<213> ORGANISM: Homo sapiens

<400> SEQUENCE: 35

Lys Lys Gln Ser Ser Trp Tyr Gln Ile
1               5

<210> SEQ ID NO 36
<211> LENGTH: 9
<212> TYPE: PRT
<213> ORGANISM: Homo sapiens

<400> SEQUENCE: 36

Pro Glu Gly Gly Thr Asp Ala Ser Arg
1               5

<210> SEQ ID NO 37
<211> LENGTH: 9
<212> TYPE: PRT
<213> ORGANISM: Homo sapiens

<400> SEQUENCE: 37

Ala Ser Phe Thr Leu Lys Leu Gln Ser
1               5
```

```
<210> SEQ ID NO 38
<211> LENGTH: 10
<212> TYPE: PRT
<213> ORGANISM: Homo sapiens

<400> SEQUENCE: 38

Gly Gly Gly Ser Asn Gly Arg Thr Ser Val
1               5                   10

<210> SEQ ID NO 39
<211> LENGTH: 11
<212> TYPE: PRT
<213> ORGANISM: Homo sapiens

<400> SEQUENCE: 39

Asn Ser Phe Leu Met Thr Ser Ser Lys Pro Arg
1               5                   10

<210> SEQ ID NO 40
<211> LENGTH: 11
<212> TYPE: PRT
<213> ORGANISM: Homo sapiens

<400> SEQUENCE: 40

Ala Cys Ser Ser Thr Val Ser Phe Ile Trp Ile
1               5                   10

<210> SEQ ID NO 41
<211> LENGTH: 14
<212> TYPE: PRT
<213> ORGANISM: Homo sapiens

<400> SEQUENCE: 41

Lys Lys Lys Lys Lys Lys Lys Arg Val Gly Gly Pro Leu Gln
1               5                   10

<210> SEQ ID NO 42
<211> LENGTH: 14
<212> TYPE: PRT
<213> ORGANISM: Homo sapiens

<400> SEQUENCE: 42

Gly Pro Val Phe Ile Cys Ser Ser Asn Cys Phe Lys Ile Thr
1               5                   10

<210> SEQ ID NO 43
<211> LENGTH: 15
<212> TYPE: PRT
<213> ORGANISM: Homo sapiens

<400> SEQUENCE: 43

Ala Pro Phe Thr Cys Trp Pro Thr Val Ala Thr Asn Thr Trp Glu
1               5                   10                  15

<210> SEQ ID NO 44
<211> LENGTH: 15
<212> TYPE: PRT
<213> ORGANISM: Homo sapiens

<400> SEQUENCE: 44

Thr Asp Gln Ser Ser Ile Ser Pro Gly Asn Arg Lys Ala Pro Gly
1               5                   10                  15

<210> SEQ ID NO 45
<211> LENGTH: 15
<212> TYPE: PRT
```

<213> ORGANISM: Homo sapiens

<400> SEQUENCE: 45

Arg Ile Met Gly Gly Gly Ile Gln Arg Glu Thr Trp Ile Ser Ser
1               5                   10                  15

<210> SEQ ID NO 46
<211> LENGTH: 16
<212> TYPE: PRT
<213> ORGANISM: Homo sapiens

<400> SEQUENCE: 46

Cys Gly Ser Trp Gly Lys Tyr Asn Leu Trp Gln Ser Ser Ser Ser Lys
1               5                   10                  15

<210> SEQ ID NO 47
<211> LENGTH: 18
<212> TYPE: PRT
<213> ORGANISM: Homo sapiens

<400> SEQUENCE: 47

Glu Ile Leu Lys Pro Glu Gly Gln His Met Lys Leu Arg Ser Glu Glu
1               5                   10                  15

Thr Ser

<210> SEQ ID NO 48
<211> LENGTH: 21
<212> TYPE: PRT
<213> ORGANISM: Homo sapiens

<400> SEQUENCE: 48

Ala Lys Ala Arg Ala Leu Ala Arg Arg Ser Glu Pro Cys Ser Thr Gly
1               5                   10                  15

Lys Leu Gln Leu Arg
            20

<210> SEQ ID NO 49
<211> LENGTH: 23
<212> TYPE: PRT
<213> ORGANISM: Homo sapiens

<400> SEQUENCE: 49

Val Gln Arg Gly Ile Gly Thr Ile Pro Ser Glu Thr Ile Pro Val Asn
1               5                   10                  15

Arg Lys Arg Val Asn Pro Pro
            20

<210> SEQ ID NO 50
<211> LENGTH: 28
<212> TYPE: PRT
<213> ORGANISM: Homo sapiens

<400> SEQUENCE: 50

Val Ser Trp Phe Pro Ser Trp Ala Arg Ser Cys Gly Arg Gln Thr Pro
1               5                   10                  15

Leu Gly Ala Thr Tyr Lys Asp Thr Leu Leu Pro Val
            20                  25

<210> SEQ ID NO 51
<211> LENGTH: 35
<212> TYPE: PRT
<213> ORGANISM: Homo sapiens

<400> SEQUENCE: 51

```
Asp Leu Gln Pro Pro Gly Arg Arg Trp Leu Pro Gln Gln Cys Pro Gly
1               5                  10                  15

Ser Pro Gly Arg Cys Asp Ala Ser Val Pro Leu Trp Ser Asp His Leu
            20                  25                  30

Pro Ser Leu
        35

<210> SEQ ID NO 52
<211> LENGTH: 36
<212> TYPE: PRT
<213> ORGANISM: Homo sapiens

<400> SEQUENCE: 52

Arg Gly Leu Gly Pro Leu Ala Ala Cys Gly Arg Ser Gly Gly Gly
1               5                  10                  15

Gly Gly Gly Gly Ala Gly Gly Thr Gly Ser Ser Asn Val Asn Lys Lys
            20                  25                  30

Thr Pro Pro Asn
        35

<210> SEQ ID NO 53
<211> LENGTH: 37
<212> TYPE: PRT
<213> ORGANISM: Homo sapiens

<400> SEQUENCE: 53

Pro Met Arg Cys Ser Cys Thr Met Gly Glu Ile Gln Met Gln Ile His
1               5                  10                  15

Cys Gly Ala Arg Arg Arg Lys Ala Val Pro Ser Ser Lys Asp Asn Val
            20                  25                  30

Gln Ser Ser Ala His
        35

<210> SEQ ID NO 54
<211> LENGTH: 48
<212> TYPE: PRT
<213> ORGANISM: Homo sapiens

<400> SEQUENCE: 54

Trp Arg Thr Thr Tyr Ile Ser Ile Leu Asn Leu Ala Gln Phe Tyr Tyr
1               5                  10                  15

Ser Leu Ile Thr Val Leu Lys Thr Phe Asn Trp Pro Gly Thr Val Val
            20                  25                  30

His Ala Cys Asn Pro Ser Thr Leu Gly Gly Gln Gly Arg Arg Ile Thr
        35                  40                  45

<210> SEQ ID NO 55
<211> LENGTH: 103
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid

<400> SEQUENCE: 55

Asp Asp Asp Ser Asp Tyr Gly Ser Ser Lys Lys Lys Asn Xaa Lys Met
1               5                  10                  15

Val Lys Lys Ser Lys Pro Glu Arg Lys Glu Lys Met Pro Lys Pro
            20                  25                  30

Arg Leu Lys Ala Thr Val Thr Pro Ser Pro Val Lys Gly Lys Gly Lys
```

```
                35                  40                  45
Val Gly Arg Pro Thr Ala Ser Lys Ala Ser Lys Glu Lys Thr Pro Ser
 50                  55                  60

Pro Lys Glu Glu Asp Glu Pro Glu Ser Pro Pro Glu Lys Lys Thr
 65                  70                  75                  80

Ser Ile Ser Pro Pro Pro Glu Lys Ser Gly Asp Glu Gly Ser Glu Asp
                 85                  90                  95

Glu Ala Pro Ser Gly Glu Asp
            100

<210> SEQ ID NO 56
<211> LENGTH: 10
<212> TYPE: PRT
<213> ORGANISM: Homo sapiens

<400> SEQUENCE: 56

Leu Ser Thr Ser Ser Phe Asp Glu Gln Asn
 1               5                  10

<210> SEQ ID NO 57
<211> LENGTH: 18
<212> TYPE: PRT
<213> ORGANISM: Homo sapiens

<400> SEQUENCE: 57

Val Ile Val Val Leu Ile Ala Val Ile Ser Phe Pro Gln Asn Tyr Thr
 1               5                  10                  15

Trp Leu

<210> SEQ ID NO 58
<211> LENGTH: 37
<212> TYPE: PRT
<213> ORGANISM: Homo sapiens

<400> SEQUENCE: 58

Pro Met Arg Cys Ser Cys Thr Met Gly Glu Ile Gln Met Gln Ile His
 1               5                  10                  15

Cys Gly Ala Arg Arg Lys Ala Val Pro Ser Ser Lys Asp Asn Val
            20                  25                  30

Gln Ser Ser Ala His
         35

<210> SEQ ID NO 59
<211> LENGTH: 14
<212> TYPE: PRT
<213> ORGANISM: Homo sapiens

<400> SEQUENCE: 59

Leu Arg Gly Thr Ser Gly Val Gln Pro Pro Glu Ile Glu Gln
 1               5                  10

<210> SEQ ID NO 60
<211> LENGTH: 5
<212> TYPE: PRT
<213> ORGANISM: Homo sapiens

<400> SEQUENCE: 60

Ile Leu His Leu His
 1               5

<210> SEQ ID NO 61
<211> LENGTH: 32
```

```
<212> TYPE: PRT
<213> ORGANISM: Homo sapiens

<400> SEQUENCE: 61

Val Leu Ser Ala Leu Pro Glu Lys Asn Cys Asn Thr Val Pro Phe Gln
1               5                   10                  15

Pro Pro Glu Asp Leu Arg Tyr Gln His Cys Ser Ser Arg Phe Leu Glu
            20                  25                  30

<210> SEQ ID NO 62
<211> LENGTH: 20
<212> TYPE: PRT
<213> ORGANISM: Homo sapiens

<400> SEQUENCE: 62

Trp Gly Phe Asn Glu Arg Asp Arg Leu Ser Ser Ile Leu Gln Gln Arg
1               5                   10                  15

Cys Val Thr Leu
            20

<210> SEQ ID NO 63
<211> LENGTH: 11
<212> TYPE: PRT
<213> ORGANISM: Homo sapiens

<400> SEQUENCE: 63

Val Val Ser Gly Phe Phe Ser Thr Phe Ser Leu
1               5                   10

<210> SEQ ID NO 64
<211> LENGTH: 9
<212> TYPE: PRT
<213> ORGANISM: Homo sapiens

<400> SEQUENCE: 64

Leu Thr Arg Pro Gly His Gly Gln Asp
1               5

<210> SEQ ID NO 65
<211> LENGTH: 11
<212> TYPE: PRT
<213> ORGANISM: Homo sapiens

<400> SEQUENCE: 65

Leu Tyr Ile Asn Glu Met Lys Ser Lys Lys Leu
1               5                   10

<210> SEQ ID NO 66
<211> LENGTH: 10
<212> TYPE: PRT
<213> ORGANISM: Homo sapiens

<400> SEQUENCE: 66

Leu Pro Gln Cys Pro Ser Arg Gly Ser Leu
1               5                   10

<210> SEQ ID NO 67
<211> LENGTH: 23
<212> TYPE: PRT
<213> ORGANISM: Homo sapiens

<400> SEQUENCE: 67

Pro Gly Trp Asp Cys Arg Leu Pro Glu Ala Glu Ser Cys Arg Phe Leu
1               5                   10                  15
```

```
Leu Ser Ser Arg Gly Glu Asp
        20
```

<210> SEQ ID NO 68
<211> LENGTH: 7
<212> TYPE: PRT
<213> ORGANISM: Homo sapiens

<400> SEQUENCE: 68

```
Lys Lys Met Arg Thr Lys Met
1               5
```

<210> SEQ ID NO 69
<211> LENGTH: 17
<212> TYPE: PRT
<213> ORGANISM: Homo sapiens

<400> SEQUENCE: 69

```
Gln Ile Asp Ser Ser Phe Ser Ile Pro Trp Val Val Val His Gly Arg
1               5                   10                  15

Ser
```

<210> SEQ ID NO 70
<211> LENGTH: 18
<212> TYPE: PRT
<213> ORGANISM: Homo sapiens

<400> SEQUENCE: 70

```
Gly Gly Arg Arg Ser Leu Arg Lys Pro Gln Ile Ser Phe Phe Leu Phe
1               5                   10                  15

Glu Arg
```

<210> SEQ ID NO 71
<211> LENGTH: 12
<212> TYPE: PRT
<213> ORGANISM: Homo sapiens

<400> SEQUENCE: 71

```
Gly Ile Arg Val Glu Pro Pro Thr Arg Thr Ile Ser
1               5                   10
```

<210> SEQ ID NO 72
<211> LENGTH: 10
<212> TYPE: PRT
<213> ORGANISM: Homo sapiens

<400> SEQUENCE: 72

```
Arg Asn Arg Tyr Ser Thr Ala Arg Glu Arg
1               5                   10
```

<210> SEQ ID NO 73
<211> LENGTH: 10
<212> TYPE: PRT
<213> ORGANISM: Homo sapiens

<400> SEQUENCE: 73

```
Gly Lys Arg His Ile Gly Gly Thr Asp Tyr
1               5                   10
```

<210> SEQ ID NO 74
<211> LENGTH: 12
<212> TYPE: PRT
<213> ORGANISM: Homo sapiens

<400> SEQUENCE: 74

```
Val Val Ser Gln Leu Thr Ala Glu Met Arg Leu Glu
1               5                   10

<210> SEQ ID NO 75
<211> LENGTH: 21
<212> TYPE: PRT
<213> ORGANISM: Homo sapiens

<400> SEQUENCE: 75

Arg Ala Cys Gln Arg Ser Thr Trp Lys Thr Lys Glu Gly Asn Gly Gln
1               5                   10                  15

Thr Glu Ser Ser Ser
            20

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000
```

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

```
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<400> SEQUENCE: 101
000

<210> SEQ ID NO 102
<400> SEQUENCE: 102
000

<210> SEQ ID NO 103
<400> SEQUENCE: 103
000

<210> SEQ ID NO 104
<400> SEQUENCE: 104
000

<210> SEQ ID NO 105
<400> SEQUENCE: 105
000

<210> SEQ ID NO 106
<400> SEQUENCE: 106
000

<210> SEQ ID NO 107
<400> SEQUENCE: 107
```

000

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
000

<210> SEQ ID NO 125
<400> SEQUENCE: 125
000

<210> SEQ ID NO 126
<400> SEQUENCE: 126
000

<210> SEQ ID NO 127
<400> SEQUENCE: 127
000

<210> SEQ ID NO 128
<400> SEQUENCE: 128
000

<210> SEQ ID NO 129
<400> SEQUENCE: 129
000

<210> SEQ ID NO 130
<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

```
<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
<400> SEQUENCE: 147
000

<210> SEQ ID NO 148
<400> SEQUENCE: 148
000

<210> SEQ ID NO 149
<400> SEQUENCE: 149
000

<210> SEQ ID NO 150
<400> SEQUENCE: 150
000

<210> SEQ ID NO 151
<400> SEQUENCE: 151
000

<210> SEQ ID NO 152
<400> SEQUENCE: 152
000

<210> SEQ ID NO 153
```

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

```
<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000
```

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189
<211> LENGTH: 3203
<212> TYPE: DNA
<213> ORGANISM: Homo sapiens

<400> SEQUENCE: 189

| | | | | | |
|---|---|---|---|---|---|
| gagaggcaga | gatcggggcg | agacaatggg | gatgtgggcg | cgggagcccc | gttccggctt | 60 |
| agcagcacct | cccagccccg | cagaataaaa | ccgatcgcgc | ccctccgcg | cgcgccctcc | 120 |
| cccgagtgcg | gagcgggagg | aggcggcggc | ggccgaggag | gaggaggagg | aggccccgga | 180 |
| ggaggaggcg | ttggaggtcg | aggcggaggc | ggaggaggag | gaggccgagg | cgccggagga | 240 |
| ggccgaggcg | ccggagcagg | aggaggccgg | ccggaggcgg | catgagacga | gcgtggcggc | 300 |
| cgcggctgct | cggggccgcg | ctggttgccc | attgacagcg | gcgtctgcag | ctcgcttcaa | 360 |
| gatggccgct | tggctcgcat | tcattttctg | ctgaacgact | tttaactttc | attgtctttt | 420 |
| ccgcccgctt | cgatcgcctc | gcgccggctg | ctctttccgg | gattttttat | caagcagaaa | 480 |
| tgcatcgaac | aacgagaatc | aagatcactg | agctaaatcc | ccacctgatg | tgtgtgcttt | 540 |
| gtggagggta | cttcattgat | gccacaacca | taatagaatg | tctacattcc | ttctgtaaaa | 600 |
| cttgtattgt | tcgttacctg | gagaccagca | agtattgtcc | tatttgtgat | gtccaagttc | 660 |
| acaagaccag | accactactg | aatataaggt | cagataaaac | tctccaagat | attgtataca | 720 |
| aattagttcc | agggcttttc | aaaaatgaaa | tgaagagaag | aagggatttt | tatgcagctc | 780 |
| atccttctgc | tgatgctgcc | aatggctcta | atgaagatag | aggagaggtt | gcagatgaag | 840 |
| ataagagaat | tataactgat | gatgagataa | taagcttatc | cattgaattc | tttgaccaga | 900 |
| acagattgga | tcggaaagta | acaaagaca | agagaaatc | taaggaggag | gtgaatgata | 960 |
| aaagatactt | acgatgccca | gcagcaatga | ctgtgatgca | cttaagaaag | tttctcagaa | 1020 |
| gtaaaatgga | catacctaat | actttccaga | ttgatgtcat | gtatgaggag | gaacctttaa | 1080 |
| aggattatta | tacactaatg | gatattgcct | acatttatac | ctggagaagg | aatggtccac | 1140 |
| ttccattgaa | atacagagtt | cgacctactt | gtaaaagaat | gaagatcagt | caccagagag | 1200 |
| atggactgac | aaatgctgga | gaactggaaa | gtgactctgg | gagtgacaag | gccaacagcc | 1260 |
| cagcaggagg | agttccctcc | acctcttctt | gtttgcctag | ccccagtact | ccagtgcagt | 1320 |
| ctcctcatcc | acagtttcct | cacatttcca | gtactatgaa | tggaaccagc | aacagcccca | 1380 |
| gcggtaacca | ccaatcttct | tttgccaata | gacctcgaaa | atcatcagta | aatgggtcat | 1440 |
| cagcaacttc | ttctgttga | tacctgagac | tgttaaggaa | aaaaatttta | aaccctgat | 1500 |
| ttatatagat | atcttcagcc | attacgactt | tctagagcta | atacatgtga | ctatcgtcca | 1560 |
| atttgctttc | ttttgtagtg | acattaaatt | tggctataaa | agatggacta | catgtgatac | 1620 |
| tcctgtccgt | cttggttcaa | aagaaagatt | gttgttataa | agaattggtt | tcttggaaag | 1680 |
| caggcaagac | ttttctctg | tgttaggaaa | gatgggaaat | ggtttctgta | accattgttt | 1740 |

```
ggatttggaa gtactctgca gtggacataa gcattgggcc atagtttgtt aatctcaact    1800
aacgcctaca ttacattctc cttgatcgtt cttgttatta cgctgttttg tgaacctgta    1860
gaaaaacaag tgcttttat cttgaaattc aaccaacgga agaatatgc atagaataat     1920 gcattctatg atgccatgtc actgtgaata acgatttctt gcagctattt agccattttg    1980
attgctgttt gatttatact tctctgttgc tacgcaaaac cgatcaaaga aaagtgaact    2040
tcagttttac aatctgtatg cctaaaagcg ggtactaccg tttattttac tgacttgttt    2100
aaatgattcg cttttgtaag aatcagatgg cattatgctt gttgtacaat gccatattgg    2160
tatatgacat aacaggaaac agtattgtat gatatatcta taaatgctat aaagaaatat    2220
tgtgtttcat gcattcagaa atgattgtta aaattctccc aactggttcg acctttgcag    2280
atacccataa cctatgttga gccttgctta ccagcaaaga atattttaa tgtggatatc     2340 taattctaaa gtctgttcca ttagaagcaa ttggcacatc tttctatact ttatatactt    2400
ttctccagta atacatgttt actttaaaaa ttgttgcagt gaagaaaaac ctttaactga    2460
gaaatatgga aaccgtctta attttccatt ggctatgatg gaattaatat tgtattttaa    2520
aaatgcatat tgatcactat aattctaaaa caattttta aataaaccag caggttgcta     2580
aaagaaggca ttttatctaa agttatttta ataggtggta tagcagtaat tttaaattta    2640
agagttgctt ttacagttaa caatggaata tgccttctct gctatgtctg aaaatagaag    2700
ctatttatta tgagcttcta caggtatttt taaatagagc aagcatgttg aatttaaaat    2760
atgaataacc ccacccaaca attttcagtt tatttttgc tttggtcgaa cttggtgtgt     2820
gttcatcagt tatttgtgag ggtgtttatt ctatatgaat attgtttcat gtttgtaggg    2880
aaattgtagc taaacatttc attgtcccca gtctgcaaaa gaagcacaat tctattgctt    2940
tgtcttgctt atagtcatta aatcattact tttacatata ttgctgttac ttctgctttc    3000
tttaaaaata tagtaaagga tgttttatga agtcacaaga tacatatatt tttattttga    3060
cctaaatttg tacagtccca ttgtaagtgt tgtttctaat tatagatgta aaatgaaatt    3120
tcatttgtaa ttggaaaaaa tccaataaaa aggatattca tttagaaaat agctaagatc    3180
tttaataaaa atttgatatg aaa                                            3203
```

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

```
<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000
```